US012617820B2

(12) United States Patent
McLellan et al.

(10) Patent No.: US 12,617,820 B2
(45) Date of Patent: May 5, 2026

(54) ENGINEERED CORONAVIRUS SPIKE (S) PROTEIN AND METHODS OF USE THEREOF

(71) Applicants: BOARD OF REGENTS, THE UNIVERSITY OF TEXAS SYSTEM, Austin, TX (US); THE TRUSTEES OF DARTMOUTH COLLEGE, Hanover, NH (US)

(72) Inventors: Jason McLellan, Austin, TX (US); Jennifer Maynard, Austin, TX (US); Andrea Chasse, Austin, TX (US); Ilya Finkelstein, Austin, TX (US); Mohammad Javanmardi, Austin, TX (US); Jeffrey Schaub, Austin, TX (US); Hung-Che Kuo, Austin, TX (US); Chia-Wei Chou, Austin, TX (US); Jory Goldsmith, Austin, TX (US); Christy Hjorth, Diana, TX (US); Ching-Lin Hsieh, Austin, TX (US); Patrick Byrne, Austin, TX (US); Nicole Johnson, Austin, TX (US); Nianshuang Wang, Austin, TX (US); Daniel Wrapp, Chandler, AZ (US)

(73) Assignees: BOARD OF REGENTS, THE UNIVERSITY OF TEXAS SYSTEM, Austin, TX (US); THE TRUSTEES OF DARTMOUTH COLLEGE, Hanover, NH (US)

( * ) Notice: Subject to any disclaimer, the term of this patent is extended or adjusted under 35 U.S.C. 154(b) by 577 days.

(21) Appl. No.: 18/000,112

(22) PCT Filed: May 28, 2021

(86) PCT No.: PCT/US2021/034713
§ 371 (c)(1),
(2) Date: Nov. 28, 2022

(87) PCT Pub. No.: WO2021/243122
PCT Pub. Date: Dec. 2, 2021

(65) Prior Publication Data
US 2023/0242594 A1  Aug. 3, 2023

Related U.S. Application Data

(60) Provisional application No. 63/032,502, filed on May 29, 2020.

(51) Int. Cl.
A61K 39/215 (2006.01)
A61P 31/14 (2006.01)
C07K 14/005 (2006.01)

(52) U.S. Cl.
CPC .......... *C07K 14/005* (2013.01); *A61K 39/215* (2013.01); *A61P 31/14* (2018.01); *C07K*

*2319/03* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 9,738,689 B2 | 8/2017 | Kwong et al. | |
| 10,960,070 B2 | 3/2021 | Graham et al. | |
| 11,684,669 B2 | 6/2023 | Meinke et al. | |
| 11,964,010 B2 | 4/2024 | Graham et al. | |
| 2017/0182151 A1 | 6/2017 | Che et al. | |
| 2021/0388032 A1* | 12/2021 | Langedijk | A61K 39/215 |
| 2023/0226171 A1 | 7/2023 | Lozano-Dubernard et al. | |
| 2023/0277653 A1 | 9/2023 | McLellan et al. | |
| 2023/0310583 A1 | 10/2023 | Sun et al. | |
| 2024/0210415 A1 | 6/2024 | Krammer et al. | |

FOREIGN PATENT DOCUMENTS

| | | |
|---|---|---|
| CN | 111088283 A | 5/2020 |
| EP | 2970398 | 1/2016 |
| EP | 3532095 | 9/2019 |
| WO | WO 2014/160463 | 10/2014 |
| WO | WO 2016/037154 | 3/2016 |
| WO | WO 2017/037196 | 3/2017 |
| WO | WO 2018/081318 | 5/2018 |
| WO | WO 2020/028902 | 2/2020 |
| WO | WO 2021/163365 | 8/2021 |
| WO | WO 2021/194826 | 9/2021 |
| WO | WO 2021/226348 | 11/2021 |
| WO | WO 2021/229270 | 11/2021 |
| WO | WO 2021/229311 | 11/2021 |
| WO | WO 2021/243122 | 12/2021 |

(Continued)

OTHER PUBLICATIONS

Extended European Search Report issued in European Application No. 2811955.0, dated Aug. 8, 2024.

Battles, M. B et al. Structure and immunogenicity of pre-fusion-stabilized human metapneumovirus F glycoprotein. *Nat. Commun.* 8, 1528 (2017).

Buchholz, U. J. et al. Contributions of the structural proteins of severe respiratory syndrome coronavirus to protective immunity. *Proc. Natl. Acad. Sci. U. S. A.* 101, 9804-9809 (2004).

Chen, Yu, Qianyun Liu, and Deyin Guo. "Emerging coronaviruses: genome structure, replication, and pathogenesis." *Journal of medical virology* 92.4 (2020): 418-423.

(Continued)

*Primary Examiner* — Agnieszka Boesen
(74) *Attorney, Agent, or Firm* — pH IP Law

(57) ABSTRACT

Provided herein are engineered Coronavirus S proteins, such as engineered SARS-CoV-2 S proteins. In some aspects, the engineered S proteins exhibit enhanced conformational stability and/or antigenicity. Methods are also provided for use of engineered proteins as diagnostics, in screening platforms and/or in vaccine compositions.

20 Claims, 13 Drawing Sheets

Specification includes a Sequence Listing.

(56)                References Cited

FOREIGN PATENT DOCUMENTS

WO        WO 2022/241229        11/2022

OTHER PUBLICATIONS

Henderson, Rory, et al. "Controlling the SARS-CoV-2 spike glycoprotein conformation." *Nature structural & molecular biology* 27.10 (2020): 925-933.

Hofmann, H. et al. S Protein of Severe Acute Respiratory Syndrome-Associated Coronavirus Mediates Entry into Hepatoma Cell Lines and Is Targeted by Neutralizing Antibodies in Infected Patients. *J. Virol.* 78, 6134-6142 (2004).

Impagliazzo, A. et al. A stable trimeric influenza hemagglutinin stem as a broadly protective immunogen. *Science* 349, 1301-1306 (2015).

Joyce, M. G. et al. Iterative structure-based improvement of a fusion-glycoprotein vaccine against RSV. *Nat. Struct. Mol. Biol.* 23, 811-820 (2016).

Krarup, Anders, et al. "A highly stable prefusion RSV F vaccine derived from structural analysis of the fusion mechanism." *Nature communications* 6.1 (2015): 8143.

Li, Z. et al. The human coronavirus HCoV-229E S-protein structure and receptor binding. *Elife* 8, 1-22 (2019).

MacGowan, Stuart A., and Geoffrey J. Barton. "Missense variants in ACE2 are predicted to encourage and inhibit interaction with SARS-CoV-2 Spike and contribute to genetic risk in COVID-19." *BioRxiv* (2020): 2020-05.

McLellan, J. S et al. Structure-Based Design of a Fusion Glycoprotein Vaccine for Respiratory Syncytial Virus. *Science* (80-. ). 342, 592-598 (2013).

Pallesen, J. et al. Immunogenicity and structures of a rationally designed prefusion MERS-CoV spike antigen. *Proc. Natl. Acad. Sci. U. S. A.* 114, E7348-E7357 (2017).

Park, Y. J. et al. Structures of MERS-CoV spike glycoprotein in complex with sialoside attachment receptors. *Nat. Struct. Mol. Biol.* 26, 1151-1157 (2019).

PCT/US2021/034713 International Search Report and Written Opinion, dated Dec. 13, 2021.

PCT/US2021/034713 Invitation to Pay Additional Fees, dated Sep. 28, 2021.

PCT/US2021/034713 Third Party Observations, dated Sep. 30, 2022.

Rutten, L. et al. A Universal Approach to Optimize the Folding and Stability of Prefusion- Closed HIV-1 Envelope Trimers. *Cell Rep.* 23, 584-595 (2018).

Rutten, L. et al. Structure-Based Design of Prefusion-Stabilized Filovirus Glycoprotein Trimers. *Cell Rep.* 30, 4540-4550.e3 (2020).

Sanders, R. W. et al. A next-generation cleaved, soluble HIV-1 Env trimer, BG505 SOSIP.664 gp140, expresses multiple epitopes for broadly neutralizing but not non-neutralizing antibodies. *PLoS Pathog.* 9, e1003618 (2013).

UniProtKB Accession No. P0DTC2, "SPIKE_SARS2", version last modified Jun. 2, 2021.

UniProtKB Accession No. P11225, "SPIKE_CVMJH", version last modified Jun. 2, 2021.

UniProtKB Accession No. P25192, "SPIKE_CVBLY", version last modified Jun. 2, 2021.

Walls, A. C. et al. Structure, Function, and Antigenicity of the SARS-CoV-2 Spike Glycoprotein. *Cell* 181, 281-292.e6 (2020).

Walls, A. C. et al. Tectonic conformational changes of a coronavirus spike glycoprotein promote membrane fusion. *Proc. Natl. Acad. Sci. U. S. A.* 114, 11157-11162 (2017).

Wang, C. et al. A human monoclonal antibody blocking SARS-CoV-2 infection. *Nat. Commun.* 11, 1-6 (2020).

Wang, N. et al. Structural Definition of a Neutralization-Sensitive Epitope on the MERS-CoV S1-NTD. *Cell Rep.* 28, 3395-3405.e6 (2019).

Wrapp, D. et al. Cryo-EM structure of the 2019-nCOV spike in the prefusion conformation. *Science* (80-. ). 367, 1260-1263 (2020).

Yang, L. et al. Structure-Guided Redesign Improves NFL HIV Env Trimer Integrity and Identifies an Inter-Protomer Disulfide Permitting Post-Expression Cleavage. *Front. Immunol.* 9, 1631 (2018).

GenBank Accession No. MN908947, dated Mar. 18, 2020, retrieved from <https://www.ncbi.nlm.nih.gov/nuccore/MN908947> on Jun. 2, 2025.

Office Communication issued in Japanese Application No. 2022-573585, mailed Jul. 7, 2025.

Baden, Lindsey R., et al. "Efficacy and safety of the mRNA-1273 SARS-CoV-2 Vaccine." *New England journal of medicine* 384.5 (2021): 403-416.

Bosch, Berend Jan, et al. "The coronavirus spike protein is a class I virus fusion protein: structural and functional characterization of the fusion core complex." *Journal of virology* 77.16 (2003): 8801-8811.

Boyoglu-Barnum, Seyhan, et al. "Glycan repositioning of influenza hemagglutinin stem facilitates the elicitation of protective cross-group antibody responses." *Nature communications* 11.1 (2020): 791.

Chan, Woan-Eng, et al. "Functional characterization of heptad repeat 1 and 2 mutants of the spike protein of severe acute respiratory syndrome coronavirus." *Journal of virology* 80.7 (2006): 3225-3237.

Chi, Xiangyang, et al. "A neutralizing human antibody binds to the N-terminal domain of the Spike protein of SARS-CoV-2." *Science* 369.6504 (2020): 650-655.

Choi, Bina, et al. "Persistence and evolution of SARS-CoV-2 in an immunocompromised host." *New England Journal of Medicine* 383.23 (2020): 2291-2293.

Cockrell, Adam S., et al. "A mouse model for MERS coronavirus-induced acute respiratory distress syndrome." *Nature microbiology* 2.2 (2016): 1-11.

Corbett, Kizzmekia S., et al. "Design of nanoparticulate group 2 influenza virus hemagglutinin stem antigens that activate unmutated ancestor B cell receptors of broadly neutralizing antibody lineages." *MBio* 10.1 (2019): 10-1128.

Corbett, Kizzmekia S., et al. "Evaluation of the mRNA-1273 vaccine against SARS-CoV-2 in nonhuman primates." *New England Journal of Medicine* 383.16 (2020): 1544-1555.

Corbett, Kizzmekia S., et al. "SARS-CoV-2 mRNA vaccine design enabled by prototype pathogen preparedness." *Nature* 586.7830 (2020): 567-571.

De la Pena, Alba Torrents, et al. "Improving the immunogenicity of native-like HIV-1 envelope trimers by hyperstabilization." *Cell reports* 20.8 (2017): 1805-1817.

Douglas, Madeline G., et al. "Adaptive evolution influences the infectious dose of MERS-CoV necessary to achieve severe respiratory disease." *Virology* 517 (2018): 98-107.

Escriou, Nicolas, et al. "Protection from SARS coronavirus conferred by live measles vaccine expressing the spike glycoprotein." *Virology* 452 (2014): 32-41.

Feige, Matthias J., ed. *Oxidative folding of proteins: Basic principles, cellular regulation and engineering.* vol. 9. Royal Society of Chemistry, 2018, Chapter 1.1: Disulfide Bonds in Protein Folding and Stability, pp. 1-33.

Gu, Hongjing, et al. "Adaptation of SARS-CoV-2 in BALB/c mice for testing vaccine efficacy." *Science* 369.6511 (2020): 1603-1607.

Hsieh et al., "Prefusion-stabilized SARS-CoV-2 S2-only antigen provides protection against SARS-CoV-2 challenge," *Nature Communications* 15:1553, pp. 1-14, 2024.

Hsieh, Ching-Lin, et al. "Structure-based design of prefusion-stabilized SARS-CoV-2 spikes." *Science* 369.6510 (2020): 1501-1505.

Huang, Yimin, et al. "Identification of a conserved neutralizing epitope present on spike proteins from all highly pathogenic coronaviruses." *BioRxiv* (2021): 2021-01.

Jackson, Lisa A., et al. "An mRNA vaccine against SARS-CoV-2-preliminary report." *New England journal of medicine* 383.20 (2020): 1920-1931.

Ke, Zunlong, et al. "Structures and distributions of SARS-CoV-2 spike proteins on intact virions." *Nature* 588.7838 (2020): 498-502.

Kirchdoerfer, Robert N., et al. "Pre-fusion structure of a human coronavirus spike protein." *Nature* 531.7592 (2016): 118-121.

(56)        References Cited

OTHER PUBLICATIONS

Kirchdoerfer, Robert N., et al. "Stabilized coronavirus spikes are resistant to conformational changes induced by receptor recognition or proteolysis." *Scientific reports* 8.1 (2018): 15701.

Ku, Zhiqiang, et al. "Molecular determinants and mechanism for antibody cocktail preventing SARS-CoV-2 escape." *Nature communications* 12.1 (2021): 469.

Kupferschmidt, Kai. "Fast-spreading UK virus variant raises alarms." (2021): 9-10.

Li, Fang. "Structure, function, and evolution of coronavirus spike proteins." *Annual review of virology* 3.1 (2016): 237-261.

Liu, Lihong, et al. "Potent neutralizing antibodies against multiple epitopes on SARS-CoV-2 spike." *Nature* 584.7821 (2020): 450-456.

Lucchese, Guglielmo, Animesh Amart Sinha, and Darja Kanduc. "How a single amino acid change may alter the immunological information of a peptide." *Frontiers in Bioscience-Elite* 4.5 (2012): 1843-1852.

Ma, Cuiqing, et al. "Searching for an ideal vaccine candidate among different MERS coronavirus receptor-binding fragments-the importance of immunofocusing in subunit vaccine design." *Vaccine* 32.46 (2014): 6170-6176.

Menachery, Vineet D., et al. "SARS-like WIV1-CoV poised for human emergence." *Proceedings of the National Academy of Sciences* 113.11 (2016): 3048-3053.

Ng, Kevin W., et al. "Preexisting and de novo humoral immunity to SARS-CoV-2 in humans." *Science* 370.6522 (2020): 1339-1343.

Polack, Fernando P., et al. "Safety and efficacy of the BNT162b2 mRNA Covid-19 vaccine." *New England journal of medicine* 383.27 (2020): 2603-2615.

Qian, Zhaohui, et al. "Identification of the receptor-binding domain of the spike glycoprotein of human betacoronavirus HKU1." *Journal of Virology* 89.17 (2015): 8816-8827.

Qiao, Hui, et al. "Specific single or double proline substitutions in the "spring-loaded" coiled-coil region of the influenza hemagglutinin impair or abolish membrane fusion activity." *The Journal of cell biology* 141.6 (1998): 1335-1347.

Sanders, Rogier W., et al. "Stabilization of the soluble, cleaved, trimeric form of the envelope glycoprotein complex of human immunodeficiency virus type 1." *Journal of virology* 76.17 (2002): 8875-8889.

Starr, Tyler N., et al. "Deep mutational scanning of SARS-CoV-2 receptor binding domain reveals constraints on folding and ACE2 binding." *cell* 182.5 (2020): 1295-1310.

Stewart-Jones, Guillaume BE, et al. "Structure-based design of a quadrivalent fusion glycoprotein vaccine for human parainfluenza virus types 1-4." *Proceedings of the National Academy of Sciences* 115.48 (2018): 12265-12270.

Tang, Julian W., et al. "Introduction of the South African SARS-CoV-2 variant 501Y. V2 into the UK." *The Journal of infection* 82.4 (2021): e8.

Turoňová, Beata, et al. "In situ structural analysis of SARS-CoV-2 spike reveals flexibility mediated by three hinges." *Science* 370. 6513 (2020): 203-208.

Wang, Lingshu, et al. "Evaluation of candidate vaccine approaches for MERS-CoV." *Nature communications* 6.1 (2015): 7712.

Wang, Lingshu, et al. "Importance of neutralizing monoclonal antibodies targeting multiple antigenic sites on the Middle East respiratory syndrome coronavirus spike glycoprotein to avoid neutralization escape." *Journal of virology* 92.10 (2018): 10-1128.

Wang, Zijun, et al. "mRNA vaccine-elicited antibodies to SARS-CoV-2 and circulating variants." *Nature* 592.7855 (2021): 616-622.

Weisblum, Yiska, et al. "Escape from neutralizing antibodies by SARS-CoV-2 spike protein variants." *elife* 9 (2020): e61312.

Widjaja, Ivy, et al. "Towards a solution to MERS: protective human monoclonal antibodies targeting different domains and functions of the MERS-coronavirus spike glycoprotein." *Emerging microbes & infections* 8.1 (2019): 516-530.

Woo, Patrick CY, et al. "Characterization and complete genome sequence of a novel coronavirus, coronavirus HKU1, from patients with pneumonia." *Journal of virology* 79.2 (2005): 884-895.

Wu, Kai, et al. "mRNA-1273 vaccine induces neutralizing antibodies against spike mutants from global SARS-CoV-2 variants." *BioRxiv* (2021): 2021-01.

Yassine, Hadi M., et al. "Hemagglutinin-stem nanoparticles generate heterosubtypic influenza protection." *Nature medicine* 21.9 (2015): 1065-1070.

Zhang, Jian, et al. "Spike-specific circulating T follicular helper cell and cross-neutralizing antibody responses in COVID-19-convalescent individuals." *Nature microbiology* 6.1 (2021): 51-58.

Zhao, S., et al. "Quantifying the transmission advantage associated with N501Y substitution of SARS-CoV-2 in the United Kingdom: An early data-driven analysis." *J. Travel Med* 28.2 (2021).

Henderson, Rory, et al. "Controlling the SARS-COV-2 Spike Glycoprotein Conformation." *bioRxiv* (2020): May 2020.

Office Communication issued in corresponding Korean Patent Application No. 10-2022-7042842, dated Mar. 10, 2026, with English Translation.

* cited by examiner

1

ENGINEERED CORONAVIRUS SPIKE (S) PROTEIN AND METHODS OF USE THEREOF

REFERENCE TO RELATED APPLICATIONS

The present application is a national phase application under 35 U.S.C. § 371 of International Application No. PCT/US2021/034713, filed May 28, 2021, which claims the priority benefit of U.S. provisional application No. 63/032,502, filed May 29, 2020, the entire contents of each of which is incorporated herein by reference.

STATEMENT REGARDING FEDERALLY SPONSORED RESEARCH

This invention was made with government support under Grant no. R01 AI127521 awarded by the National Institutes of Health. The government has certain rights in the invention.

REFERENCE TO A SEQUENCE LISTING

The instant application contains a Sequence Listing, which has been submitted in ASCII format and is hereby incorporated by reference in its entirety. Said ASCII copy, created on Nov. 28, 2022, is named UTSBP1251US_ST25.txt and is 41,774 bytes in size.

BACKGROUND

1. Field

The present disclosure relates generally to the fields of medicine, virology, immunology and protein engineering. More particular, the disclosure relates to engineered Coronavirus S proteins and the use thereof in drug design and vaccine formulation.

2. Description of Related Art

An outbreak of COVID-19, the disease caused by infection of the coronavirus SARS-CoV-2, began in December 2019 in China has resulted in millions of infections and more than 100 thousand deaths. Like the virus that caused the SARS outbreak several years prior, SARS-CoV, the SARS-CoV-2 virus use their spike proteins to bind host cellular receptor angiotensin-converting enzyme 2 (ACE2). The interaction between the receptor binding domain (RBD) of the spike glycoprotein and the full-length human ACE2 protein. Although the sequence and structure of the SARS-CoV-2 spike protein is a known (see, e.g., Wrapp et al. 2020) there remains a need for stabilized S proteins that could be used for identifying drug candidates and for stimulating an effective immune response to the S protein.

SUMMARY

In some embodiments, the present disclosure provides engineered proteins, comprising an engineered coronavirus S protein ectodomain having at least 90% identity to: (a) positions 14-1208 of SEQ ID NO: 1 or 2; (b) positions 14-1160 of SEQ ID NO: 1 or 2; or (c) positions 319-1208 of SEQ ID NO: 1 or 2, said engineered protein comprising at least one mutation relative to the sequence of SEQ ID NO: 1 or 2, said at least one mutation comprising:

(1) an engineered disulfide bond;
(2) a cavity filling substitution;
(3) a substitution that provides an electrostatic or polar interaction; and/or
(4) a proline substitution.

In further aspects, an engineering protein comprises at least one engineered disulfide bond and at least one cavity filling substitution. In still further aspects, an engineering protein comprises at least one engineered disulfide bond and at least one substitution that provides an electrostatic or polar interaction. In still further aspects, an engineering protein comprises at least one engineered disulfide bond and at least one proline substitution. In additional aspects, an engineering protein comprises at least one cavity filling substitution and at least one substitution that provides an electrostatic or polar interaction. In still further aspects, an engineering protein comprises at least one cavity filling substitution and at least one proline substitution. In still further aspects, an engineering protein comprises at least one substitution that provides an electrostatic or polar interaction and at least one proline substitution.

In some embodiments, the present disclosure provides engineered proteins comprising an engineered coronavirus S protein ectodomain that comprises a sequence at least 90% identical to: (a) positions 14-1208 of SEQ ID NO: 1 or 2; (b) positions 14-1160 of SEQ ID NO: 1 or 2; or (c) positions 319-1208 of SEQ ID NO: 1 or 2; wherein the engineered protein comprises the following substitutions relative to the sequence of SEQ ID NO: 1 or 2: F817P, A892P, A899P, A942P, K986P, and V987P. In further aspects, the engineered coronavirus S protein has at least about 91%, 92%, 93%, 94%, 95%, 96%, 97% or 98% identity to: (a) positions 14-1208 of SEQ ID NO: 1 or 2; (b) positions 14-1160 of SEQ ID NO: 1 or 2; or (c) positions 319-1208 of SEQ ID NO: 1 or 2.

In further embodiments, the present disclosure provides engineered proteins, comprising an engineered coronavirus S protein ectodomain having at least 90% identity to: (a) positions 14-1208 of SEQ ID NO: 1 or 2; (b) positions 14-1160 of SEQ ID NO: 1 or 2; or (c) positions 319-1208 of SEQ ID NO: 1 or 2, said at least one mutation comprising:

(i) a substitution at a position corresponding to: T724, T752, T778, T961, I1013, H1058, S735, T859, I770, A1015, L727, S1021, Q901, S875, T912, H1088, L1141, V1040, L966, A766, T778, L938, V963, V911, N1108, V705, A893, N703, A672, A694, A1080, I1132, P862, T547, N978, S758, Q762, D1118, S659, S698, R1039, V722, A930, A903, Q913, S974, D979, P728, V951, V736, L858, S884, P807, T791, A879, G799, A924, V826, A899, Q779, F817, L865, T866, A892, A899, A570, T874, S1055, V729, A1022, L894, A713, L828, L822, A1056, Q965, S1003, A972, Q992, I980, A1078, V1133, T1120, I870, T1117, D1139, T1116, Y1138, I896, G885, F1103, P1112, G889, L1034, E819, A972, I980, I1081, N1135, E819, Q1054, Q957, I1130, V1040, V1104, R1000, A944, T724, A944, S730, G769, Q895, K921, L922, A942, G946, S975, A890; and
(ii) a deletion corresponding to positions 829-851, 675-686, 673-684, 1161-1208, or 1142-1208; and
(iii) a substitution of two amino acids for amino acid positions 673-686.

In further aspects, the engineered coronavirus S protein has at least about 91%, 92%, 93%, 94%, 95%, 96%, 97% or 98% identity to: (a) positions 14-1208 of SEQ ID NO: 1 or 2; (b) positions 14-1160 of SEQ ID NO: 1 or 2; or (c) positions 319-1208 of SEQ ID NO: 1 or 2.

In some aspects, the engineered proteins comprise an engineered disulfide bond comprising paired cysteine substitutions at positions corresponding to: S735C and T859C; I770C and A1015C; L727C and 51021C; V911C and N1108C; A672C and A694C; A1080C and I1132C; S659C and S698C; V722C and A930C; A903C and Q913C; S974C and D979C; P728C and V951C; V736C and L858C; S884C and A893C; P807C and S875C; T791C and A879C; G799C and A924C; A570C and V963C; T874C and S1055C; V729C and A1022C; L822C and A1056C; Q965C and 51003C; A972C and Q992C; I980C and Q992C; A1078C and V1133C; H1088C and T1120C; I870C and S1055C; T1117C and D1139C; T1116C and Y1138C; I896C and Q901C; G885C and Q901C; F1103C and P1112C; G889C and L1034C; E819C and S1055C; A972C and I980C; I1081C and N1135C; or E819C and Q1054C.

In some aspects, the engineered proteins comprise an engineered disulfide bond comprising paired cysteine substitutions at positions corresponding to: A903C and Q913C; S884C and A893C; T791C and A879C; Q965C and S1003C; or T1117C and D1139C. In other aspects, the engineered proteins comprise an engineered disulfide bond comprising paired cysteine substitutions at positions corresponding to S884C and A893C. In further aspects, the engineered proteins further comprise at least one additional engineered disulfide bond. In further aspects, the engineered proteins further comprise an engineered disulfide bond comprising paired cysteine substitutions at positions corresponding to T791C and A879C; or G799C and A924C.

In other aspects, the engineered proteins comprise an engineered disulfide bond comprising paired cysteine substitutions at positions corresponding to A903C and Q913C. In further aspects, the engineered proteins further comprise at least one additional engineered disulfide bond. In further aspects, the engineered proteins further comprise an engineered disulfide bond comprising paired cysteine substitutions at positions corresponding to Q965C and S1003C; S884C and A893C; T791C and A879C; or G799C and A924C. In further aspects, the engineered proteins further comprise an engineered disulfide bond comprising paired cysteine substitutions at positions corresponding to A903C and Q913C; and/or Q965C and S1003C.

In some aspects, the engineered proteins comprise a cavity filling substitution at a position corresponding to: T724, I1013, H1058, Q901, S875, H1088, L1141, V1040, T778, L938, V963, R1039, V826, A899, Q779, L894, V1040, V1104, R1000, A944, S730, A890, D1118, or 51003. In further aspects, the engineered proteins comprise a cavity filling substitution at a position corresponding to: T778, L938, V963, or H1088. In other aspects, the engineered proteins comprise a cavity filling substitution selected from: T724M, I1013F, H1058W, Q901M, S875F, H1088W, L1141F, V1040F, T778L, L938F, V963L, R1039F, V826L, A899F, Q779M, L894F, H1058F, H1058Y, V1040Y, H1088Y, V1104I, R1000Y, R1000W, A944F, T724I, A944Y, S730L, A890V, D1118F, or S1003V. In further aspects, the engineered proteins comprise a cavity filling substitution selected from: T778L, L938F, V963L, or H1088Y. In other aspects, the engineered proteins comprise a cavity filling substitution at a position corresponding to L938. In further aspects, the engineered proteins comprise a L938F substitution. In further aspects, the engineered proteins further comprise a cavity filling substitution at a position corresponding to V963. In further aspects, the engineered proteins comprise a V963L substitution.

In some aspects, the engineered proteins comprise a proline substitution selected from: F817P, L865P, T866P, A892P, A899P, T912P, A893P, Q895P, K921P, L922P, N978P, A942P, G946P, or S975P. In further aspects, the engineered proteins comprise a proline substitution selected from: F817P, A892P, A899P, or A942P. In other aspects, the engineered proteins comprise a proline substitution F817P. In further aspects, the engineered proteins further comprise an engineered disulfide bond. In further aspects, the engineered proteins further comprise an engineered disulfide bond comprising paired cysteine substitutions at positions corresponding to S884C and A893C; or T791C and A879C. In further aspects, the engineered proteins further comprise an engineered disulfide bond comprising paired cysteine substitutions at positions corresponding to S884C and A893C. In some aspects, the engineered proteins further comprise an additional proline substitution at V987P and/or K986P. In some aspects, the engineered proteins comprise a proline substitution A892P. In further aspects, the engineered proteins further comprise an additional proline substitution at A942P; A899P; and/or F817P. In some aspects, the engineered proteins comprise at least two proline substations selected from A892P; A942P; A899P; and/or F817P. In further aspects, the engineered proteins comprise at least three proline substations selected from A892P; A942P; A899P; and/or F817P. In further aspects, the engineered proteins comprise proline substations at A892P; A942P; A899P; and F817P. In other aspects, the engineered proteins comprise a proline substitution A899P or T912P. In still other aspects, the engineered proteins comprise a proline substitution A892P and T912P.

In some aspects, the engineered proteins comprise a substitution that provides an electrostatic interaction substitution at a position corresponding T752, T912, L966, L828, S730, T961, A766, P862, T859, Q957, or G769. In further aspects, the engineered proteins comprise an electrostatic interaction substitution at a position corresponding to: T961, L966, T859, or G769. In still further aspects, the engineered proteins comprise an electrostatic interaction substitution of T961D or T961E. In yet further aspects, the engineered proteins comprise a substitution of T961D. In some aspects, the engineered proteins further comprise L966D or L966E substitution, preferably a L966E substitution. In other aspects, the engineered proteins comprise an electrostatic interaction substitution selected from: T752K, T912R, L966D, L828K, L828R, S730R, T961D, A766E, P862E, T859K, Q957E, or G769E. In further aspects, the engineered proteins comprise an electrostatic interaction substitution selected from: T961D, L966D, T859K, or G769K. In yet further aspects, the electrostatic interaction substitution selected from: T961D, T859K, or G769K. In some aspects, the engineered proteins comprise a substitution that provides an electrostatic or polar interaction substitution at a position corresponding T778, A713, or I1130. In some aspects, the engineered proteins comprise an electrostatic interaction substitution selected from: T778Q, A713S, or I1130Y. In some aspects, the engineered proteins comprise a substitution that provides an electrostatic interaction substitution at a position and a F817P.

In some aspects, the engineered proteins further comprise a substitution at a position corresponding to L984, D985, K986, and/or V987. In further aspects, the engineered proteins comprise a substitution at a position corresponding to L984, D985, K986, and/or V987 to glycine or proline. In some aspects, the engineered proteins comprise K986P and V987P substitutions. In further aspects, the engineered proteins further comprise a substitution a position corresponding to A570, T572, F855, and/or N856. In further aspects, the engineered proteins further comprise a cavity-filling substitution at a position corresponding to A570, T572, F855, and/or N856. In some aspects, the engineered protein comprises a combination of at least one engineered disulfide bond and at least one proline substitution. In further aspects, the engineered protein comprises a combination of at least one cavity filling substitution and at least one proline substitution. In still further aspects, the engineered protein comprises a combination of at least one proline substitution and at least one electrostatic interaction substitution. In some aspects, the engineered protein comprises a combination of at least one engineered disulfide bond, at least one cavity filling substitution, at least one proline substitution and at least one electrostatic interaction substitution. In some aspects, the engineered proteins have at least 95% identity to positions 319-1208 of SEQ ID NO: 1 or 2. In some aspects, the engineered proteins comprise an engineered coronavirus S protein ectodomain having 95% identity to positions 16-1208 of SEQ ID NO: 1 or 2. In some aspects, the engineered proteins comprise the engineered coronavirus S protein ectodomain comprises a mutation that eliminates the furin cleavage site. In further aspects, the engineered proteins the mutation that eliminates the furin cleavage site comprises a GSAS substitution at positions 682-685.

Any of the substitutions described herein may engineered into any known coronavirus S protein variant, including, but not limited to, a coronavirus S protein having any one or more of the following modifications (see SEQ ID NO: 2): L5F, S131, L18F, T19R, T20N, P26S, Q52R, A67V, H69del, V70del, V70I, D80A, T95I, D138Y, Y144del, Y144V, W152C, E154K, R1905, D215G, L242del, A243del, L244del, D253G, W258L, K417N, K417T, L452R, S477N, T478K, E484K, E484Q, E484K, N501Y, A570D, D614G, H655Y, Q677H, P681R, P681H, A701V, T716I, F888L, D950N, S982A, T1027I, D1118H, and V1176F. Exemplary combinations of such modifications are provided in Table 5.

In some aspects, the engineered proteins are fused or conjugated to a trimerization domain. In further aspects, the protein is fused to a trimerization domain. In some aspects, the a trimerization domain is positioned C-terminally relative to S protein ectodomain. In some aspects, the a trimerization domain comprises a T4 fibritin trimerization domain. In some aspects, the protein is fused or conjugated to a transmembrane domain. In some aspects, the protein is fused to a transmembrane domain. In some aspects, the transmembrane domain comprises a coronavirus spike protein transmembrane domain. In some aspects, the transmembrane domain comprises a SARS-CoV or a SARS-CoV-2 transmembrane domain.

In still other embodiments, the present disclosure provides engineered coronavirus trimers comprising at least one subunit of the present disclosure. In some aspects, the trimer is stabilized in a prefusion conformation relative to a trimer of wildtype S protein subunits. In some aspects, the trimer comprises at least one engineered disulfide bond between subunits. In further aspects, the at least one engineered disulfide bond between subunits is selected: V705C and A983C; T547C and N968C; T961C and S758C; and/or T961C and Q762C.

In yet other embodiments, the present disclosure provides pharmaceutical compositions comprising a pharmaceutically acceptable carrier; and (i) an engineered protein of the present disclosure, or (ii) an engineered trimer of the present disclosure. In some aspects, the compositions further comprise an adjuvant.

In other embodiments, the present disclosure provides nucleic acid molecules comprising a nucleotide sequence that encodes an amino acid sequence of an engineered protein of the present disclosure. In some aspects, the nucleic acid comprises a DNA expression vector. In other aspects, the nucleic acid comprises a mRNA.

In yet other embodiments, the present disclosure provides compositions comprising an engineered protein of the present disclosure bound to an antibody.

In yet other embodiments, the present disclosure provides methods of treating or preventing a Coronavirus infection in a subject, the method comprising administering to the subject a therapeutically effective amount of an engineered S protein of the embodiments to the subject. In some aspects, the method stimulates a humoral and/or cellular immune response in the subject. In some aspects, the method reduces inflammation in the lungs of a subject who becomes infected with coronavirus. In some aspects, the subject is infected with SARS-CoV or SARs-Cov-2. In some aspects, the subject an uninfected subject, at risk for infection with SARS-CoV or SARs-Cov-2. In some aspects, the subject has an increased risk for pneumonia. In some aspects, the methods further comprise administering to the subject a further anti-viral therapy.

In other embodiments, the present disclosure provides methods of detecting coronavirus, coronavirus S protein-binding antibodies and/or coronavirus-infected cells in a sample or subject comprising: (a) contacting a subject or a sample from the subject with the an engineered S protein of the present disclosure; and (b) detecting binding of said antibody or cell to the engineered S protein. In some aspects, the sample is a body fluid or biopsy. In some aspects, the sample is blood, bone marrow, sputum, tears, saliva, mucous, serum, urine, feces or a nasal swab. In some aspects, detection comprises immunohistochemistry, flow cytometry, FACS, ELISA, RIA or Western blot. In some aspects, the methods further comprise performing steps (a) and (b) a second time and determining a change in detection levels as compared to the first time. In some aspects, the engineered S protein further comprises a label or a is immobilized on a surface. In further aspects, said label is a peptide tag, an enzyme, a magnetic particle, a chromophore, a fluorescent molecule, a chemo-luminescent molecule, or a dye. In some aspects, engineered S protein is conjugated to a liposome or nanoparticle.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

6VSB). The 51 domains are shown as a transparent surface. The S2 domain for each protomer is shown as a ribbon diagram. Each inset corresponds to one of four types of spike variants (proline, salt bridge, disulfide, cavity filling). Side chains in each inset are as follows: top left (proline), bottom left (disulfide), top right (salt bridge), and bottom right (cavity filling).

Figures 2A, 2B, 2C, 2D:
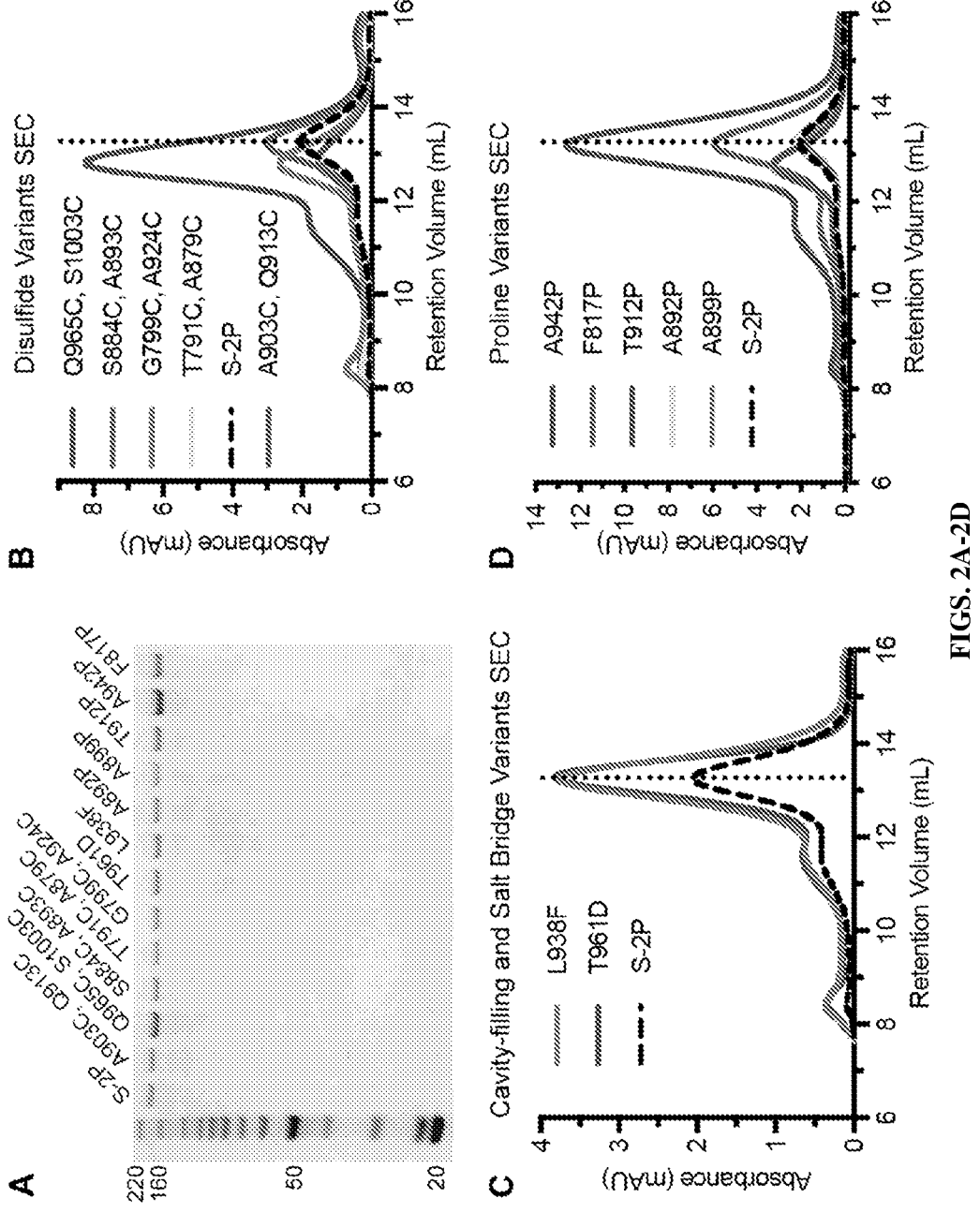

FIGS. 2A-2G show characterization of single-substitution spike variants. (FIG. 2A) SDS-PAGE of SARS-CoV-2 S-2P and single-substitution spike variants. Molecular weight standards are indicated at the left in kDa. (FIGS. 2B-2D) Size exclusion chromatography of purified spike variants, grouped by type (FIG. 2B, disulfide variants; FIG. 2C, cavity-filling and salt bridge; FIG. 2D, proline). Representative data for S-2P is shown on each graph as a dashed black line. A vertical dotted line indicates the characteristic peak retention volume for S-2P. The top line on FIG. 2B is Q965C, 51003C. The top line on FIG. 2D is A942P, and the second from the top line on FIG. 2D is F817P. (FIG. 2E) Representative negative stain electron micrographs for four variants. (FIG. 2F) Differential scanning fluorimetry (DSF) analysis of spike variant thermostability. The vertical dotted line indicates the first apparent melting temperature for S-2P. The line with a valley at about 47° C. is A942P. The line with a valley at about 67° C. is A892P. (FIG. 2G) Concentrations of individual variants in culture medium, determined by quantitative biolayer interferometry. Variants are sorted by type. The dotted line indicates the calculated concentration of S-2P, which was used as a control for comparison.

FIGS. 3A-3D show characterization of multi-substitution spike variants. (FIG. 3A) SDS-PAGE of SARS-CoV-2 Combo variants. Molecular weight standards are indicated at the left in kDa. (FIG. 3B) SEC traces for S-2P, A892P and four Combo variants. The vertical dotted line indicates the peak retention volume for S-2P. (FIG. 3C) DSF analysis of Combo variant thermostability. The left vertical dotted line indicates the first apparent melting temperature for S-2P, the right vertical dotted line shows the first apparent melting temperature for Combo47 (HexaPro). (FIG. 3D) Negative stain electron micrograph of purified Combo47.

FIGS. 4A-4H show that HexaPro exhibits enhanced expression and stability compared to S-2P. (FIG. 4A) SEC trace of HexaPro after purification from a 2 L culture of FreeStyle 293 cells. (FIG. 4B) Negative stain electron micrograph of HexaPro purified from FreeStyle 293 cells. (FIG. 4C) SEC trace of HexaPro after purification from a 2 L culture of ExpiCHO cells. (FIG. 4B) Negative stain electron micrograph of HexaPro purified a 2 L culture of ExpiCHO cells. (FIGS. 4E & 4F) Binding of S-2P (FIG. 4E) and HexaPro (FIG. 4F) to ACE2 assessed by surface plasmon resonance. Binding data are shown as black lines and the best fit to a 1:1 binding model is shown as red lines. (FIGS. 4G & 4H) Assessment of protein stability by negative stain electron microscopy. The top row of micrographs in (FIG. 4G) and (FIG. 4H) corresponds to S-2P, the bottom row corresponds to HexaPro.

Figures 5A, 5B:
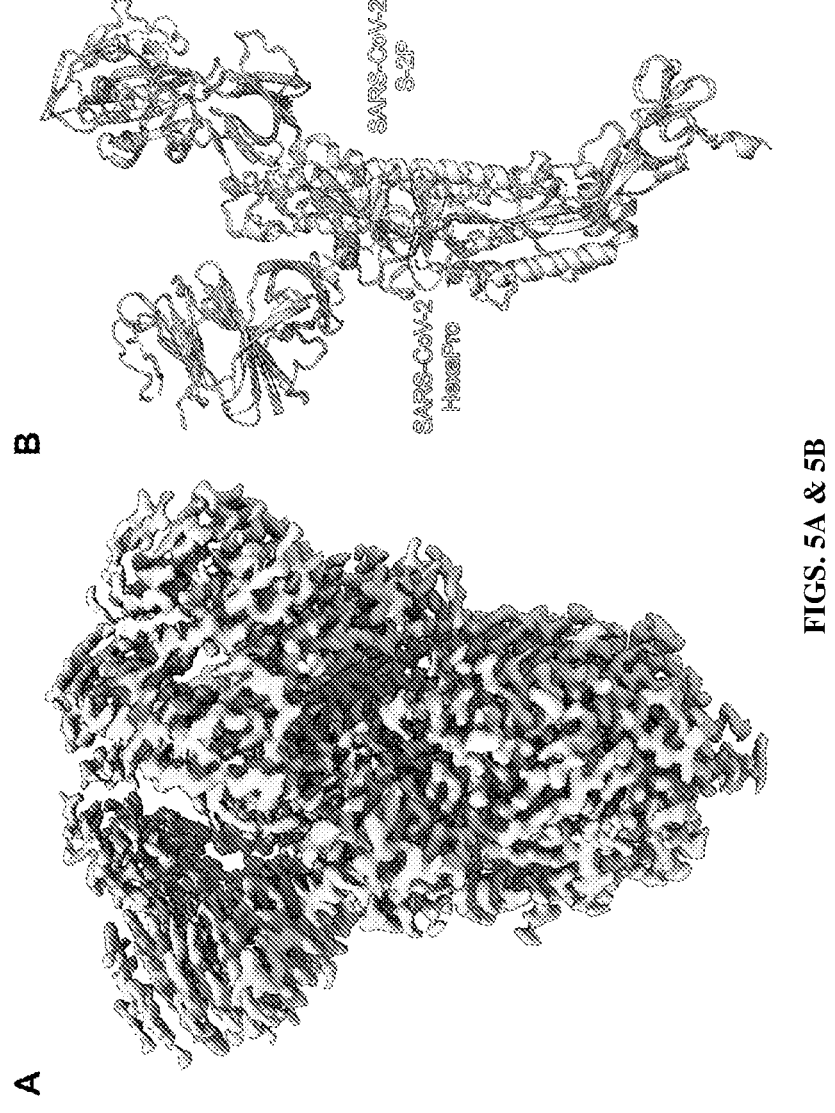
Figure 5C:
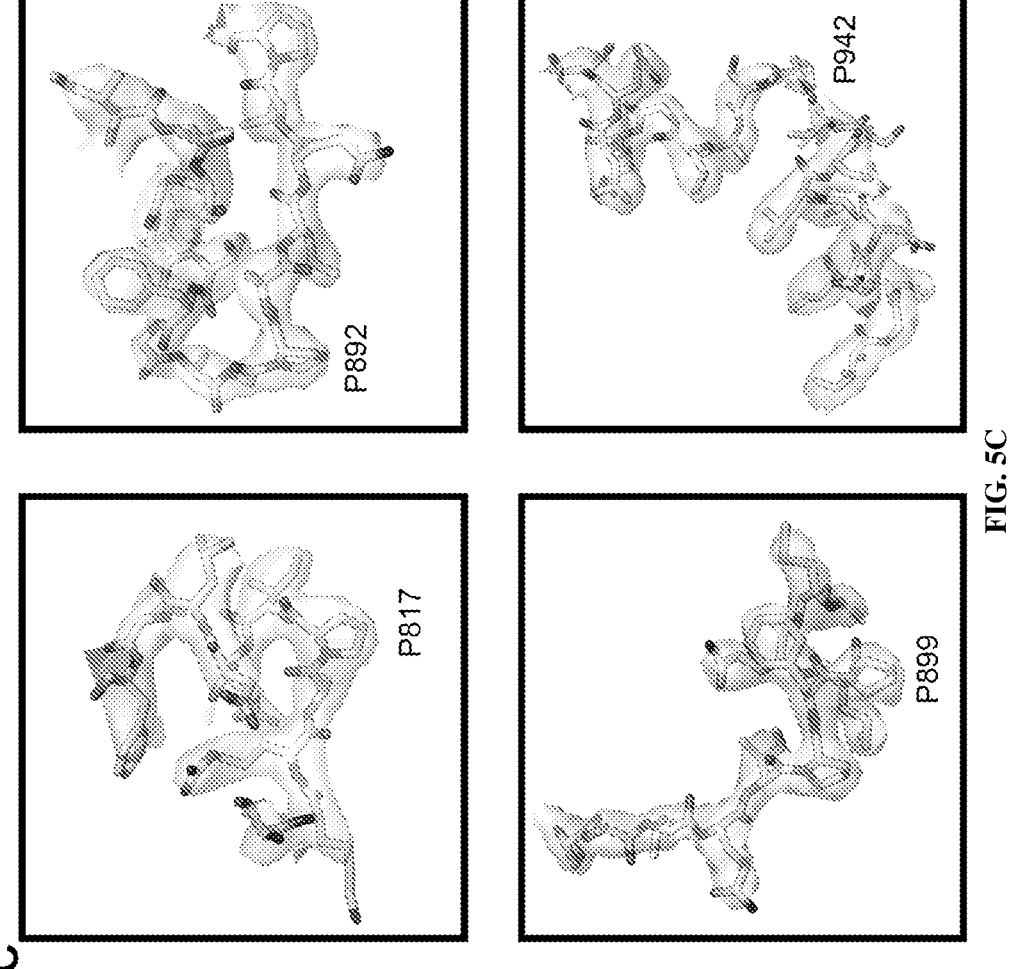

FIGS. 5A-5C show high resolution cryo-EM structure of HexaPro. (FIG. 5A) EM density map of trimeric HexaPro. (FIG. 5B) Alignment of HexaPro (green ribbon) with S-2P (white ribbon, PDB ID: 6VSB). The lone protomer adopting the one-RBD-up conformation is shown. (FIG. 5C) Zoomed view of the four proline substitutions unique to HexaPro. The EM density map is shown as a transparent surface, individual atoms are shown as sticks.

Figure 6:
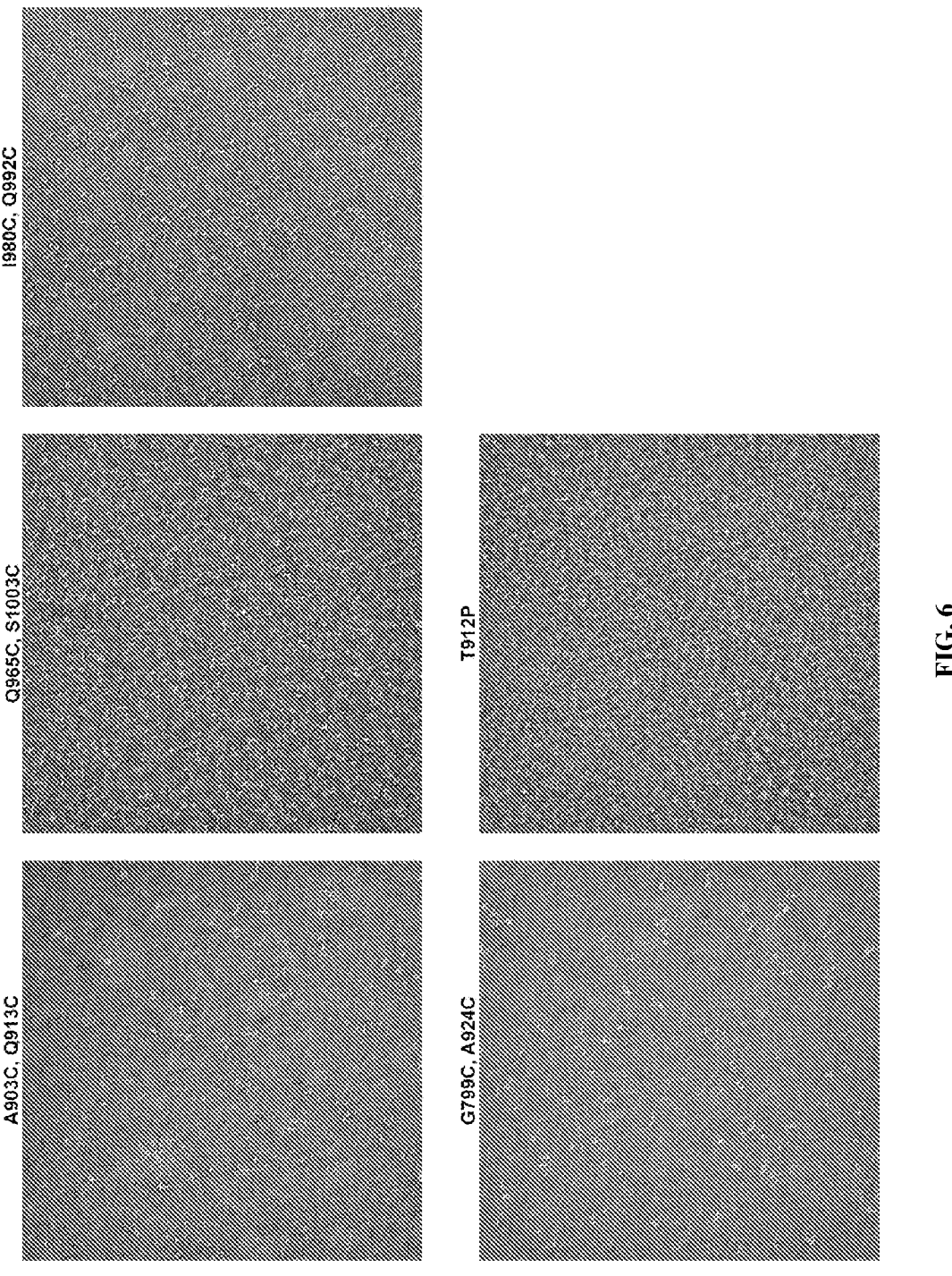

FIG. 6 shows negative-stain EM images of variants with left-shifted SEC peaks.

Figure 7:
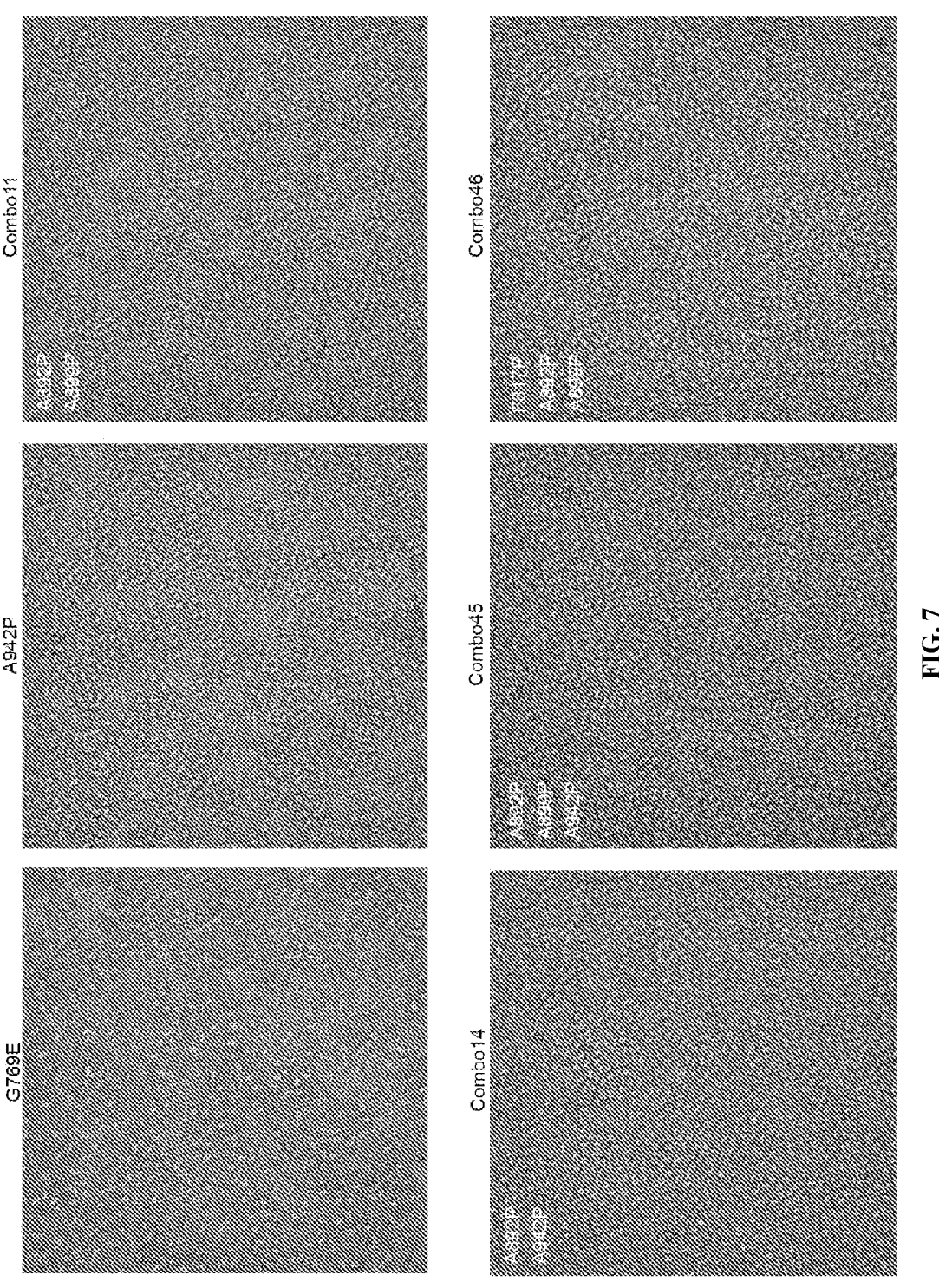

FIG. 7 shows negative-stain EM images of well-folded particles.

Figures 8A, 8B:
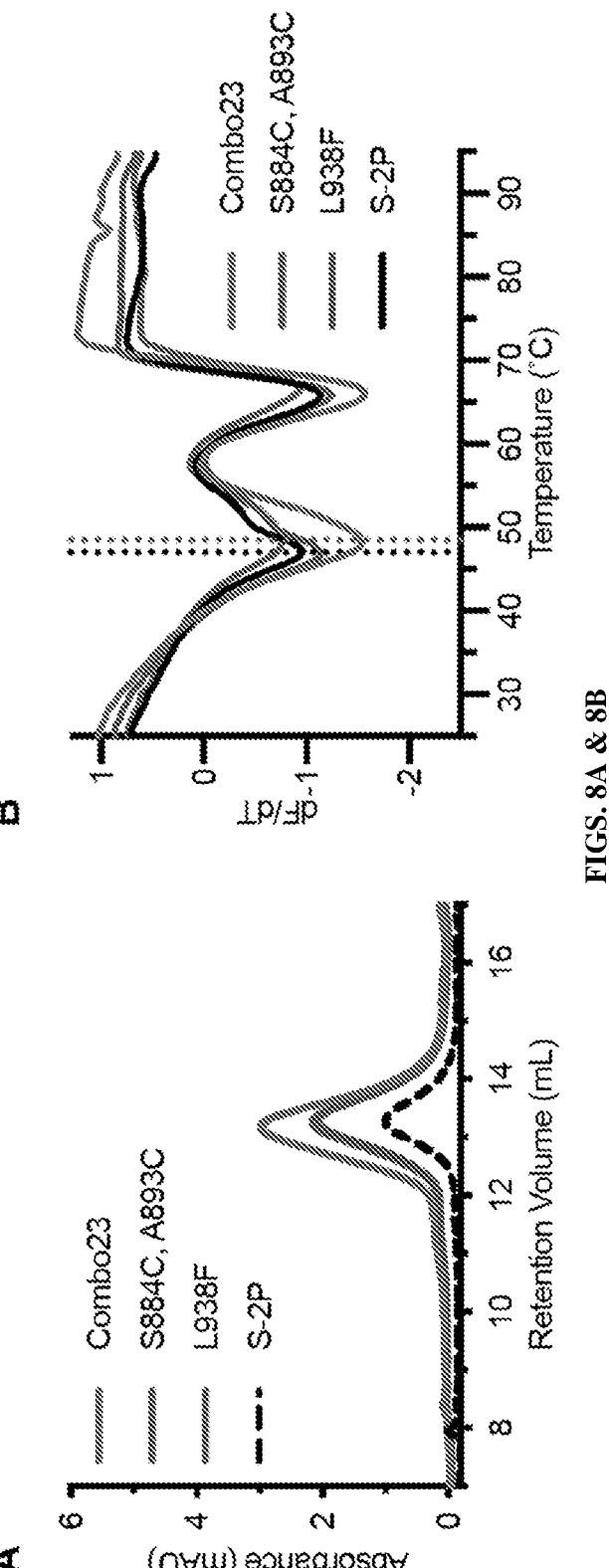

FIGS. 8A-8B show characterization of a disulfide and cavity-filling combination variant (Combo23). (FIG. 8A) SEC traces of S-2P, Combo23, and the parental variants S884C/A893C (disulfide bond) and L938F (cavity filling). The top line is Combo23. (FIG. 8B) DSF melting temperature analysis of S-2P, Combo23, and its parental variants. The left vertical dashed line represents the Tm of S-2P, and the right vertical dashed line represents the Tm of S884C/A893C.

Figure 9:
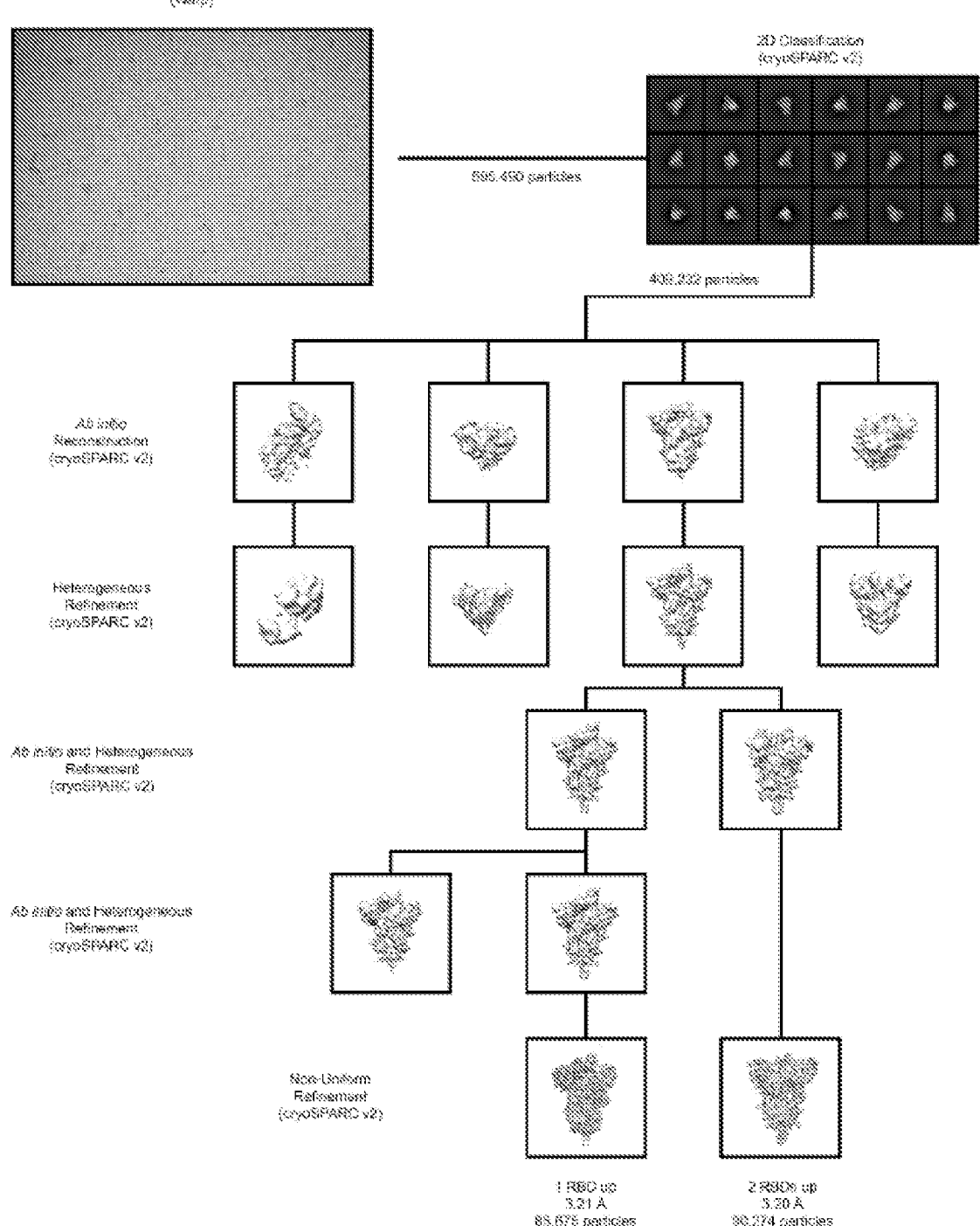

FIG. 9 shows cryo-EM data processing workflow.

Figure 10:
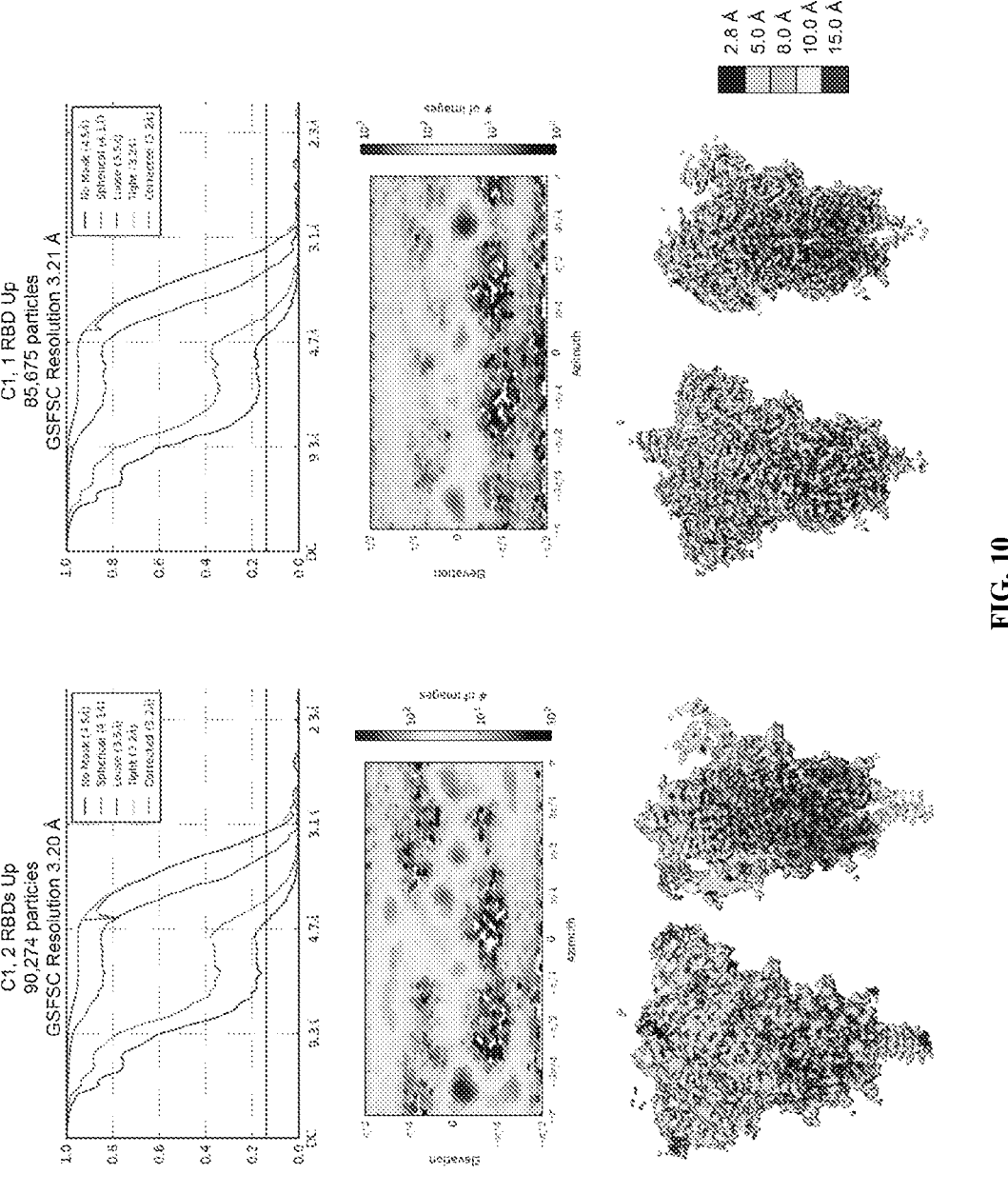

FIG. 10 shows cryo-EM structure validation. FSC curves and viewing distribution plots, generated in cryoSPARC v2.15, are shown for both the two-RBD-up (left) and the one-RBD-up (right) reconstruction. Cryo-EM density of each reconstruction is shown according to local resolution, with a central slice through the density shown to the right.

DESCRIPTION OF ILLUSTRATIVE EMBODIMENTS

Provided herein are engineered coronavirus spike proteins. In some aspects proteins of the embodiments are stabilized in a conformation present before membrane fusions. Such engineered proteins can be used, for example, to stimulate anti-coronavirus S protein specific immune response. In further aspects, engineered S proteins can be used to detect S protein binding antibodies in a sample. Thus, the engineered proteins provided herein allow for more effective method for vaccination against coronavirus as well as enabling new assay method for detecting anti-coronavirus antibodies, e.g., biological samples.

I. Definitions

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise. As used herein the specification, "a" or "an" may mean one or more. As used herein in the claim(s), when used in conjunction with the word "comprising," the words "a" or "an" may mean one or more than one.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CHL CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. As used herein, antigens also include immunogens and haptens.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the Coronavirus S protein specific antibodies of the present invention are specific to Coronavirus S protein. In some embodiments, the antibody that binds to Coronavirus S protein has a dissociation constant (Kd) of $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M).

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., Coronavirus S protein or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences.

Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally occurring amino acid and polymers. The terms "polypeptide" and "protein" specifically encompass Coronavirus S protein binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a Coronavirus S protein-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, PA, 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat viral infection.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

II. The Coronavirus Spike Protein

The spike protein of SARS-CoV-2 plays an essential role in virus entry into host cells and thus a primary target by neutralizing antibodies. The spike protein comprises an N-terminal S1 subunit and a C-terminal S2 subunit, which are responsible for receptor binding and membrane fusion. The S1 subunit is further divided into the N-terminal domain, the receptor-binding domain (RBD), the subdomain 1 (SD1) and subdomain 2 (SD2), and the S2 subunit is further divided into the fusion peptide (FP), the heptad repeat 1 (HR1) and heptad repeat 2 (HR2). The spike binds to a cellular receptor through its RBD, which triggers a conformational change of the spike. The activated spike is cleaved by a protease (such as TMPRSS2 for SARS-CoV and SARS-CoV-2) at S1/S2 site to release the S1 subunit and expose the FP on S2 subunit. The HR1 and HR2 refold to the post-fusion conformation to drive membrane fusion 35. Due to the functionality and a higher immunogenicity of the S1, most neutralizing antibodies characterized for coronavirus to date target the S1 subunit. A major challenge is that the S2 conformation is highly dynamic during membrane fusion, making it difficult to prepare the spike protein antigen and generate effective immune responses against spike (e.g., produce neutralizing antibodies). Spike protein stabilizing strategies have been demonstrated herein by mutation of the spike protein coding sequence. Mutations analyzed and provided herein are detailed in Table 1-3, below. Mutant proteins were expressed as detailed in the Examples and the amount produced protein and trimer complex was determined.

TABLE 1

Spike protein substitutions and mutations.

| Designation | Mutations | Strategy | Expressed (yield, % WT AUC) | Fraction trimeric | EM (% trimer) |
|---|---|---|---|---|---|
| CL-1 | T724M | Cav | 1.3 X (AUC) | 99% | |
| CL-2 | T752K | salt bridge | <0.5X (SDS) | | |
| CL-3 | T778Q | H bond | 2.6X (AUC) | 99% | <10% |
| CL-4 | T961D | salt bridge (inter-prot) | 1.8X (AUC) | 99% | >99% |
| CL-5 | I1013F | Cav | 0.8X (AUC) | 99% | >99% |
| CL-6 | H1058W | Cav | <0.5X (SDS) | N.D. | |
| CL-7 | S735C, T859C | DS | <0.5X (SDS) | N.D. | |
| CL-8 | I770C, A1015C | DS | <0.5X (SDS) | N.D. | |
| CL-9 | L727C, S1021C | DS | <0.5X (SDS) | N.D. | |
| CL-10 | Q901M | Cav (at the expense of H bond) | 0.9X (AUC) | 99% | |
| CL-11 | S875F | Cav | <0.5X (SDS) | N.D. | |
| CL-12 | T912R | salt bridge | <0.5X (SDS) | N.D. | |
| CL-13 | H1088W | Cav | 0.6X (AUC) | less than 33% | |
| CL-14 | L1141F | Cav | 0.8X (AUC) | 99% | |
| CL-15 | V1040F | Cav | <0.5X (SDS) | N.D. | |
| CL-16 | L966D | salt bridge | <0.5X (SEC) | N.D. | |

TABLE 1-continued

Spike protein substitutions and mutations.

| Designation | Mutations | Strategy | Expressed (yield, % WT AUC) | Fraction trimeric | EM (% trimer) |
|---|---|---|---|---|---|
| CL-17 | A766E | salt bridge (inter-prot) | <0.5X (SDS) | N.D. | |
| CL-18 | del(829-851) | remove flexible region | <0.5X (SDS) | N.D. | |
| CL-19 | T778L | Cav | 1.5X (AUC) | 99% | |
| CL-20 | L938F | Cav | 2.5X (AUC) | 99% | |
| CL-21 | V963L | Cav | 1.9X(AUC) | 99% | |
| CL-22 | V911C, N1108C | DS | 0X (SDS) | N.D. | |
| CL-23 | V705C-A893C | DS (inter-prot), introduce N-glycan | <0.5X (SDS) | N.D. | |
| CL-24 | N703Q/V705C-A893C | DS (inter-prot) | <0.5X (SDS) | N.D. | |
| CL-25 | replace (673-686) with GS | remove flexible region | 0X (SDS) | N.D. | |
| CL-26 | replace (673-686) with GS + A672C-A694C | remove flexible region, DS (S1-S2) | <0.5X (SDS) | N.D. | |
| CL-48 | A1080C/I1132C | DS | <0.5X (SDS) | N.D. | |
| CL-58 | P862E | salt bridge (inter-Sl/S2) | <0.5X (SDS) | N.D | |
| CL-59 | T859K | salt bridge (inter-Sl/S2) | 2.1X (AUC) | >95% | |
| CL-60 | T547C/N978C | DS (inter-Sl/S2) | 0X (SDS) | N.D. | |
| CL-61 | T961C/S758C | DS (inter-prot) | 0X (SDS) | N.D. | |
| CL-62 | T961C/Q762C | DS (inter-prot) | 0X (SDS) | N.D. | |
| CL-63 | D1118F | Charge removal, pi-pi stacking | 0.5X (SDS) | N.D. | |
| CL-64 | S659C-S698C | DS (inter-Sl/S2) | 0.4X (AUC) | | |
| CL-65 | delHR2 | Remove flexible HR2 (1161-1208) | 2.5X (AUC) | >99% | |
| CL-66 | delStalk | Remove flexible stalk region (1142-1208) | 2.6X (AUC) | >99% | |
| DW-1 | R1039F | Charge removal, pi-pi stacking | 0.5X (SDS) | NA | |
| JM-1 | V722C, A930C | Disulfide | 0.1X (SDS) | N.D. | |
| JM-3 | A903C, Q913C | Disulfide | 2.3X (SDS) | >90% | |
| JM-6 | S974C,D979C | Disulfide | 0.3X (SDS) | N.D. | |
| JM-11 | P728C, V951C | Disulfide | 0X (SDS) | N/A | |
| JM-14 | V736C, L858C | Disulfide | 0X (SDS) | N.D. | |
| JM-15 | S884C, A893C | Disulfide | 2X (AUC) | >99% | >99% |
| JM-18 | P807C, S875C | Disulfide | 1.1X (AUC) | >99% | |
| JM-19 | T791C, A879C | Disulfide | 1.0X (SDS) | >99% | >99% |
| JM-25 | G799C, A924C | Disulfide | 1.2X (SDS) | >90% | |
| CL-49 | V826L | Cav | 1.0X (SDS) | >90% | |
| CL-50 | A899F | Cav (inter-prot) | 0.3X (SDS) | N.D | |
| CL-51 | F817P | Proline | 2.3X (SDS) | >95% | >99% |
| CL-52 | L865P/Q779M | Proline/Cav | 0.1X(SDS) | N.D | |
| CL-35 | T866P | Proline | <0.5X (SDS) | | |
| CL-36 | A892P | Proline, Cav | 1.5X (AUC) | >99% | |
| CL-37 | A899P | Proline, Cav | 1.5X (AUC) | >99% | |
| CL-38 | T912P | Proline, Cav | 2.5X | 51% | |
| JG-1 | A570C/V963C | Disulfide | 0X (SDS) | N.D. | |
| CL-27 | T874C, S1055C | DS | 0.6X (BCA) | N.D. | |
| CL-28 | L894F | Cav (inter-prot) | 0.9X (BCA, AUC) | N.D. | |
| CL-29 | A713S | H bond | 1X (BCA, AUC) | N.D. | |
| CL-30 | V729C, A1022C | DS | 0.4X (BCA), 0.1X (AUC) | N.D. | |
| CL-31 | L828K | salt bridge | 0.8X (AUC) | >99% | |
| CL-32 | L828R | salt bridge | 0.8X (BCA), 0.4X (AUC) | nd | |
| CL-33 | H1058F | Cav | 0X (SDS) | >99% | |
| CL-34 | H1058Y | Cav, maybe H bond | 0.3X (AUC) | nd | |
| JM-2 | L822C, A1056C | Disulfide | | | |
| JM-4 | Q965C, S1003C | Disulfide | 2X (AUC), 2x (BCA) | 100% | |
| JM-5 | A972C, Q992C | Disulfide | ~1X (AUC, % trimer), 1.2x (BCA) | 97.80% | |
| JM-7 | I980C, Q992C | Disulfide | 1.3X (BCA), 2X (AUC) | | |
| JM-8 | A1078C, V1133C | Disulfide | −0.5X (BCA), <1% (AUC) | nd | |
| JM-9 | H1088C,T1120C | Disulfide | | | |
| JM-10 | I870C, S1055C | Disulfide | −0.37X (BCA), −1% AUC | nd | |
| JM-12 | T1117C, D1139C | Disulfide | 1.9X (BCA), 1X (trimer AUC) | 75% | |
| JM-13 | T1116C, Y1138C | Disulfide | 0X (SDS) | N.D. | |
| JM-16 | I896C, Q901C | Disulfide | | | |
| JM-17 | G885C, Q901C | Disulfide | 1.2X (BCA), 1.1x (AUC), | 96% | |
| JM-20 | F1103C, P1112C | Disulfide | 0.45X (BCA), 15% (AUC) | nd | |
| JM-21 | G889C, L1034C | Disulfide | 0.3X (BCA), 5% (AUC) | nd | |
| JM-22 | E819C, S1055C | Disulfide | | | |
| JM-23 | A972C, I980C | Disulfide | 1.3X | 54% | |
| JM-24 | I1081C, N1135C | Disulfide | 0.5X (BCA), 0.3 X (AUC) | nd | |
| JM-26 | E819C, Q1054C | Disulfide | 0X (SDS) | nd | |
| JM-27 | Q957E | salt bridge (inter-prot) | 1.5X (SDS, BCA) | 76% | |
| CL-44 | V1040Y | Cav | 0.5X (BCA), 0.3X (AUC) | high | |
| CL-45 | H1088Y | Cav | 1.0X (BCA), 1.6X (AUC) | high | |

TABLE 1-continued

Spike protein substitutions and mutations.

| Designation | Mutations | Strategy | Expressed (yield, % WT AUC) | Fraction trimeric | EM (% trimer) |
|---|---|---|---|---|---|
| CL-46 | VI1041 | Cav | 0.7X (AUC) | >99% | |
| CL-47 | I1130Y | H bond (inter-pro) | 0X (SDS) | >99% | |
| JM-28 | R1000Y | Cavity-filling plus H-bond to HR1 | 1X (BCA), 0.3X (AUC) | nd | |
| JM-29 | R1000W | Cavity-filling | 0.7x (BCA), 1X (AUC) | nd | |
| JM-30 | A944F | Cavity-filling | 1X (BCA), 0.4x (AUC) | nd | |
| JM-31 | A944F, T724I | Cavity-filling | 0.9X (BCA), | nd | |
| JM-32 | A944Y | Cavity-filling | | | |
| JM-33 | S730L | Cavity-filling | 0X (SDS) | >99% | |
| JM-34 | S730R | Salt bridge | 0.15X (AUC) | nd | |
| JM-35 | G769E | Salt bridge | 3X (AUC) | high | |
| CL-53 | A893P | Proline | 1.5 (SDS) | >95% | |
| CL-54 | Q895P | Proline | 2.1 (SDS) | >95% | |
| CL-55 | K921P | Proline | 1.1 (SDS) | N.D | |
| CL-56 | L922P | Proline | 0.8 (SDS) | N.D | |
| CL-57 | N978P | Proline | 0.9 (SDS) | N.D | |
| CL-39 | A942P | Proline | 4.0X (AUC) | >99% | >99% |
| CL-40 | G946P | Proline | 1.0X (SDS) | | |
| CL-41 | S975P | Proline | | | |
| CL-42 | A890V | Cav | 1.0X (SDS) | | |
| CL-43 | S1003V | Cav | | | |

TABLE 2

Additional mutations.

| | Mutations | Strategy | Expressed (yield, % WT AUC) | Fraction trimeric | EM (% trimer) |
|---|---|---|---|---|---|
| CL-1 | T724M | Cav | 1.3 X (AUC) | 99% | |
| CL-2 | T752K | salt bridge | <0.5X (SDS) | | |
| CL-3 | T778Q | H bond | 2.6X (AUC) | 99% | <10% |
| CL-4 | T961D | salt bridge (inter-prot) | 1.8X (AUC) | 99% | >99% |
| CL-5 | I1013F | Cav | 0.8X (AUC) | 99% | >99% |
| CL-6 | H1058W | Cav | <0.5X (SDS) | N.D. | |
| CL-7 | S735C, T859C | DS | <0.5X (SDS) | N.D. | |
| CL-8 | I770C, A1015C | DS | <0.5X (SDS) | N.D. | |
| CL-9 | L727C, S1021C | DS | <0.5X (SDS) | N.D. | |
| CL-10 | Q901M | Cav (at the expense of H bond) | 0.9X (AUC) | 99% | |
| CL-11 | S875F | Cav | <0.5X (SDS) | N.D. | |
| CL-12 | T912R | salt bridge | <0.5X (SDS) | N.D. | |
| CL-13 | H1088W | Cav | 0.6X (AUC) | less than 33% | |
| CL-14 | L1141F | Cav | 0.8X (AUC) | 99% | |
| CL-15 | V1040F | Cav | <0.5X (SDS) | N.D. | |
| CL-16 | L966D | salt bridge | 1.5X (AUC) | 99% | |
| CL-17 | A766E | salt bridge (inter-prot) | <0.5X (SDS) | N.D. | |
| CL-18 | del(829-851) | remove flexible region | <0.5X (SDS) | N.D. | |
| CL-19 | T778L | Cav | 1.5X (AUC) | 99% | |
| CL-20 | L938F | Cav | 2.5X (AUC) | 99% | |
| CL-21 | V963L | Cav | 1.9X(AUC) | 99% | |
| CL-22 | V911C, N1108C | DS | 0X (SDS) | N.D. | |
| CL-23 | V705C-A893C | DS (inter-prot), introduce N-glycan | <0.5X (SDS) | N.D. | |
| CL-24 | N703Q/V705C-A893C | DS (inter-prot) | <0.5X (SDS) | N.D. | |
| CL-25 | replace (673-686) with GS | remove flexible region | 0X (SDS) | N.D. | |
| CL-26 | replace (673-686) with GS + A672C-A694C | remove flexible region, DS (S1-S2) | <0.5X (SDS) | N.D. | |
| CL-48 | A1080C/I1132C | DS | <0.5X (SDS) | N.D. | |
| CL-58 | P862E | salt bridge (inter-Sl/S2) | <0.5X (SDS) | N.D | |
| CL-59 | T859K | salt bridge (inter-Sl/S2) | 2.1X (AUC) | >95% | |
| CL-60 | T547C/N978C | DS (inter-Sl/S2) | 0X (SDS) | N.D. | |
| CL-61 | T961C/S758C | DS (inter-prot) | 0X (SDS) | N.D. | |
| CL-62 | T961C/Q762C | DS (inter-prot) | 0X (SDS) | N.D. | |
| CL-63 | D1118F | Charge removal, pi-pi stacking | 0.5X (SDS) | N.D. | |
| CL-64 | S659C-S698C | DS (inter-Sl/S2) | 0.4X (AUC) | | |
| CL-65 | delHR2 | remove flappy HR2 | 2.5X (AUC) | | |
| DW-1 | R1039F | Charge removal, pi-pi stacking | 0.5X (SDS) | NA | |
| JM-1 | V722C, A930C | Disulfide | 0.1X(SDS) | N.D. | |
| JM-3 | A903C, Q913C | Disulfide | 2.3X (SDS) | >90% | |

TABLE 2-continued

|  |  |  | Additional mutations. |  |  |
| --- | --- | --- | --- | --- | --- |
|  | Mutations | Strategy | Expressed (yield, % WT AUC) | Fraction trimeric | EM (% trimer) |
| JM-6 | S974C,D979C | Disulfide | 0.3X (SDS) | N.D. |  |
| JM-11 | P728C, V951C | Disulfide | 0X (SDS) | N/A |  |
| JM-14 | V736C, L858C | Disulfide | 0X (SDS) | N.D. |  |
| JM-15 | S884C, A893C | Disulfide | 2X (AUC) | >99% | >99% |
| JM-18 | P807C, S875C | Disulfide | 1.1X (AUC) | >99% |  |
| JM-19 | T791C, A879C | Disulfide | 1.0X (SDS) | >99% | >99% |
| JM-25 | G799C, A924C | Disulfide | 1.2X (SDS) | >90% |  |
| CL-49 | V826L | Cav | 1.0X (SDS) | >90% |  |
| CL-50 | A899F | Cav (inter-prot) | 0.3X (SDS) | N.D |  |
| CL-51 | F817P | Proline | 2.3X (SDS) | >95% | >99% |
| CL-52 | L865P/Q779M | Proline/Cav | 0.1X(SDS) | N.D |  |
| CL-35 | T866P | Proline | <0.5X (SDS) |  |  |
| CL-36 | A892P | Proline, Cav | 1.5X (AUC) | >99% |  |
| CL-37 | A899P | Proline, Cav | 1.5X (AUC) | >99% |  |
| CL-38 | T912P | Proline, Cav | 2.5X | 51% |  |
| JG-1 | A570C/V963C | Disulfide | 0X (SDS) | N.D. |  |
| CL-27 | T874C, S1055C | DS | 0.6X (BCA) | N.D. |  |
| CL-28 | L894F | Cav (inter-prot) | 0.9X (BCA, AUC) | N.D. |  |
| CL-29 | A713S | H bond | 1X (BCA, AUC) | N.D. |  |
| CL-30 | V729C, A1022C | DS | 0.4X (BCA), 0.1X (AUC) | N.D. |  |
| CL-31 | L828K | salt bridge | 0.8X (AUC) | >99% |  |
| CL-32 | L828R | salt bridge | 0.8X (BCA), 0.4X (AUC) | nd |  |
| CL-33 | H1058F | Cav | 0X (SDS) | >99% |  |
| CL-34 | H1058Y | Cav, maybe H bond | 0.3X (AUC) | nd |  |
| JM-2 | L822C, A1056C | Disulfide |  |  |  |
| JM-4 | Q965C, S1003C | Disulfide | 2X (AUC), 2x (BCA) | 100% |  |
| JM-5 | A972C, Q992C | Disulfide | ~1X (AUC, % trimer), 1.2x (BCA) | 97.80% |  |
| JM-7 | I980C, Q992C | Disulfide | 1.3X (BCA), 2X (AUC) |  |  |
| JM-8 | A1078C, V1133C | Disulfide | −0.5X (BCA), <1% (AUC) | nd |  |
| JM-9 | H1088C,T1120C | Disulfide |  |  |  |
| JM-10 | I870C, S1055C | Disulfide | −0.37X (BCA), −1% AUC | nd |  |
| JM-12 | T1117C, D1139C | Disulfide | 1.9X (BCA), 1X (trimer AUC) | 75% |  |
| JM-13 | T1116C, Y1138C | Disulfide | 0X (SDS) | N.D. |  |
| JM-16 | I896C, Q901C | Disulfide |  |  |  |
| JM-17 | G885C, Q901C | Disulfide | 1.2X(BCA), 1.1x (AUC), | 96% |  |
| JM-20 | F1103C, P1112C | Disulfide | 0.45X (BCA), 15% (AUC) | nd |  |
| JM-21 | G889C, L1034C | Disulfide | 0.3X (BCA), 5% (AUC) | nd |  |
| JM-22 | E819C, S1055C | Disulfide |  |  |  |
| JM-23 | A972C, I980C | Disulfide | 1.3X | 54% |  |
| JM-24 | I1081C, N1135C | Disulfide | 0.5X (BCA), 0.3 X (AUC) | nd |  |
| JM-26 | E819C, Q1054C | Disulfide | 0X (SDS) | nd |  |
| JM-27 | Q957E | salt bridge (inter-prot) | 1.5X (SDS, BCA) | 76% |  |
| CL-44 | V1040Y | Cav | 0.5X (BCA), 0.3X (AUC) | high |  |
| CL-45 | H1088Y | Cav | 1.0X (BCA), 1.6X (AUC) | high |  |
| CL-46 | VI1041 | Cav | 0.7X (AUC) | >99% |  |
| CL-47 | I1130Y | H bond (inter-pro) | 0X (SDS) | >99% |  |
| JM-28 | R1000Y | Cavity-filling plus H-bond to HR1 | 1X (BCA), 0.3X (AUC) | nd |  |
| JM-29 | R1000W | Cavity-filling | 0.7x (BCA), 1X (AUC) | nd |  |
| JM-30 | A944F | Cavity-filling | 1X (BCA), 0.4x (AUC) | nd |  |
| JM-31 | A944F, T724I | Cavity-filling | 0.9X (BCA), | nd |  |
| JM-32 | A944Y | Cavity-filling |  |  |  |
| JM-33 | S730L | Cavity-filling | 0X (SDS) | >99% |  |
| JM-34 | S730R | Salt bridge | 0.15X (AUC) | nd |  |
| JM-35 | G769E | Salt bridge | 3X (AUC) | high |  |
| CL-53 | A893P | Proline | 1.5 (SDS) | >95% |  |
| CL-54 | Q895P | Proline | 2.1 (SDS) | >95% |  |
| CL-55 | K921P | Proline | 1.1 (SDS) | N.D |  |
| CL-56 | L922P | Proline | 0.8 (SDS) | N.D |  |
| CL-57 | N978P | Proline | 0.9 (SDS) | N.D |  |
| CL-39 | A942P | Proline | 4.0X (AUC) | >99% | >99% |
| CL-40 | G946P | Proline | 1.0X (SDS) |  |  |
| CL-41 | S975P | Proline |  |  |  |
| CL-42 | A890V | Cav | 1.0X (SDS) |  |  |
| CL-43 | S1003V | Cav |  |  |  |

TABLE 3

Further spike protein mutations.

| | Mutations | Strategy | Expressed (yield, % WT AUC) | Fraction trimeric |
|---|---|---|---|---|
| NW-1 | R983P | proline | | |
| NW-2 | L984P | proline | 0.4X (SDS) | NA |
| NW-3 | D985P | proline | 0.2X (SDS) | NA |
| NW-4 | 986P | proline | 2.1X(SDS) | >90% |
| NW-5 | 987P | proline | 1.5X (SDS) | |
| delta Strep | Remove one Strep tag | | 1.2X (SDS) | |
| delta TwinStrep | Remove both Strep tags | | 1X(AUC) | |
| JM-36 | T1027I | Cav | 0.9X(AUC) | |
| delta RBD | replace 333-525 with GGSG | remove RBD | 0.9X(AUC) | |
| delta MPER | end at 1161 | delete C-terminal | | |
| NW-6 | 984P,985P | proline | 3X(SDS) | |
| NW-7 | 984P,985G,986P | proline/glycine | 0.5 | |
| NW-8 | 984P,985G,986G | proline/glycine | 0.5 | |
| NW-9 | 984G,985P,986G | proline/glycine | 0.8 | |
| NW-10 | 984G,985P,986P | proline/glycine | 1.2 | Yes |
| NW-11 | 984G,985G,986P | proline/glycine | 0.5 | |
| NW-12 | 984P,985P,986G | proline/glycine | 0.5 | |

TABLE 4

(part 1).Oligos.

| | Mutations | Strategy | Expressed (yield, % WT AUC) | Fraction trimeric |
|---|---|---|---|---|
| NW-1 | R983P | proline | | |
| NW-2 | L984P | proline | 0.4X (SDS) | NA |
| NW-3 | D985P | proline | 0.2X (SDS) | NA |
| NW-4 | 986P | proline | 2.1X(SDS) | >90% |
| NW-5 | 987P | proline | 1.5X (SDS) | |
| delta Strep | Remove one Strep tag | | 1.2X (SDS) | |
| delta TwinStrep | Remove both Strep tags | | 1X(AUC) | |
| JM-36 | T1027I | Cav | 0.9X(AUC) | |
| delta RBD | replace 333-525 with GGSG | remove RBD | 0.9X(AUC) | |
| delta MPER | end at 1161 | delete C-terminal | | |
| NW-6 | 984P,985P | proline | 3X(SDS) | |
| NW-7 | 984P,985G,986P | proline/glycine | 0.5 | |
| NW-8 | 984P,985G,986G | proline/glycine | 0.5 | |
| NW-9 | 984G,985P,986G | proline/glycine | 0.8 | |
| NW-10 | 984G,985P,986P | proline/glycine | 1.2 | Yes |
| NW-11 | 984G,985G,986P | proline/glycine | 0.5 | |
| NW-12 | 984P,985P,986G | proline/glycine | 0.5 | |

TABLE 4

(part 2). Oligos.

| Unique # | Sequence (5'-3') |
|---|---|
| 0 | GGTACCAGA (SEQ ID NO: 3) |
| P0001 | CCGTCTCAGGCCGAGTTCGGTACC (SEQ ID NO: 4) |
| P0002 | GGAAACAAGGCAACTTCAAGAACCTGAGAGAATTC (SEQ ID NO: 5) |
| P0003 | GCCGTCGATGTTCTTGAACACGAATTC (SEQ ID NO: 6) |
| P0004 | GGGTCTGCTTCCTCTGTAGCTAGC (SEQ ID NO: 7) |
| P0005 | GGTGTAGGCGATGATGCTCTGGCTAGC (SEQ ID NO: 8) |
| P0006 | CAGCTCTGTGCTGAACGATATCCTGTCTAGA (SEQ ID NO: 9) |
| P0007 | GGCTTCTGGAGGGTCCAGTCTAGA (SEQ ID NO: 10) |
| P0008 | GGCCTCGGGGATGTATCCGGATC (SEQ ID NO: 11) |
| P0009 | GGGCAGGATCTCTGTTGTGCAGCTAATTGTAAAG (SEQ ID NO: 12) |

TABLE 4-continued

| (part 2). Oligos. | |
| --- | --- |
| Unique # | Sequence (5'-3') |
| P0010 | CTTTACAATTAGCTGCACAACAGAGATCCTGCCC (SEQ ID NO: 13) |
| p0011 | GGATCTTGCCGATGCAAGAATTGAACTGG (SEQ ID NO: 14) |
| P0012 | CCAGTTCAATTCTTGCATCGGCAAGATCC (SEQ ID NO: 15) |
| P0013 | GCCATGCAGATGTGCTATAGATTCAACGGAATCGGCGTGACCTGCAACGTGCTGTATG (SEQ ID NO: 16) |
| P0014 | CATACAGCACGTTGCAGGTCACGCCGATTCCGTTGAATCTATAGCACATCTGCATGGC (SEQ ID NO: 17) |
| P0015 | CTTCTGGAGGGTCCAGTCTAGACAGGATACAGTTCAGCACAGAGCAGATGGCGCCAAAAT (SEQ ID NO: 18) |
| P0016 | CAGAGATCCTGTGCGTGAGCATGACC (SEQ ID NO: 19) |
| P0017 | GGTCATGCTCACGCACAGGATCTCTG (SEQ ID NO: 20) |
| P0018 | CAAACTGCAGGACTGCGTGAATCAGAACGC (SEQ ID NO: 21) |
| P0019 | GCGTTCTGATTCACGCAGTCCTGCAGTTTG (SEQ ID NO: 22) |
| P0020 | gaccaagaccagctgtgactgtacaatgt (SEQ ID NO: 23) |
| P0021 | acattgtacagtcacagctggtcttggtc (SEQ ID NO: 24) |
| P0022 | ttcaacggctgcacagttctcccac (SEQ ID NO: 25) |
| P0023 | gtgggagaactgtgcagccgttgaa (SEQ ID NO: 26) |
| P0024 | tcacatgtgggtggacatttggcgccggcgcctgcctgca (SEQ ID NO: 27) |
| P0025 | tgcaggcaggcgccggcgccaaatgtccacccacatgtga (SEQ ID NO: 28) |
| P0026 | aggcttagaaggatcacagagaatctggct (SEQ ID NO: 29) |
| P0027 | agccagattctctgtgatccttctaagcct (SEQ ID NO: 30) |
| P0028 | tcagtacacctgtgccctgctggct (SEQ ID NO: 31) |
| P0029 | agccagcagggcacaggtgtactga (SEQ ID NO: 32) |
| P0030 | aagcagatctacaagtgcccacctatcaag (SEQ ID NO: 33) |
| P0031 | cttgataggtgggcacttgtagatctgctt (SEQ ID NO: 34) |
| P0032 | tctgccctgctgtgtggcaccatca (SEQ ID NO: 35) |
| P0033 | tgatggtgccacacagcagggcaga (SEQ ID NO: 36) |
| P0034 | ctggctaaagttaaagcagccgaagtcctt (SEQ ID NO: 37) |
| P0035 | aaggacttcggctgctttaactttagccag (SEQ ID NO: 38) |
| P0036 | aaccagaagctgatctgtaaccagttcaattct (SEQ ID NO: 39) |
| P0037 | agaattgaactggttacagatcagcttctggtt (SEQ ID NO: 40) |
| P0038 | cggccagggtgagcttgttgaac (SEQ ID NO: 41) |
| P0039 | gttcaacaagctcaccctggccg (SEQ ID NO: 42) |
| P0040 | aggccatctgcatgaaaaaggggatctg (SEQ ID NO: 43) |
| P0041 | cagatcccctttttcatgcagatggcct (SEQ ID NO: 44) |
| P0042 | gatcctcgatagggctccgcttgc (SEQ ID NO: 45) |
| P0043 | gcaagcggagccctatcgaggatc (SEQ ID NO: 46) |
| P0044 | gacaaaaataccatggaggtgttcgccc (SEQ ID NO: 47) |
| P0045 | gggcgaacacctccatggtattttttgtc (SEQ ID NO: 48) |
| P0046 | tcgtcggtcggcagaggtgg (SEQ ID NO: 49) |
| P0047 | ccacctctgccgaccgacga (SEQ ID NO: 50) |

TABLE 4-continued

| (part 2). Oligos. |  |
| --- | --- |
| Unique # | Sequence (5'-3') |

| P0048 | gccgcagaagtcaacgaatttagactgtcccagc (SEQ ID NO: 51) |
| P0049 | gctgggacagtctaaattcgttgacttctgcggc (SEQ ID NO: 52) |
| P0050 | ggcttctggagggtccagtggagacaggatatcgttc (SEQ ID NO: 53) |
| P0051 | gaacgatatcctgtctccactggaccctccagaagcc (SEQ ID NO: 54) |
| P0052 | cttcggcttctggagggtccggtctagacaggatatcg (SEQ ID NO: 55) |
| P0053 | cgatatcctgtctagaccggaccctccagaagccgaag (SEQ ID NO: 56) |
| P0054 | ggacttcggcttctggagggggcagtctagacagg (SEQ ID NO: 57) |
| P0055 | cctgtctagactgcccctccagaagccgaagtcc (SEQ ID NO: 58) |
| P0056 | ggtcttggtcatgctcacgcacaggatctctgttgtg (SEQ ID NO: 59) |
| P0057 | cacaacagagatcctgtgcgtgagcatgaccaagacc (SEQ ID NO: 60) |
| P0058 | gggcgttctgattcacgcagtcctgcagtttgccc (SEQ ID NO: 61) |
| P0059 | gggcaaactgcaggactgcgtgaatcagaacgccc (SEQ ID NO: 62) |
| P0060 | cagttacgagtgcgacatccctatcggc (SEQ ID NO: 63) |
| P0061 | ccctgaacaccctggtgaagcagc (SEQ ID NO: 64) |
| P0062 | ccctgatcagctgttgggtcacg (SEQ ID NO: 65) |
| P0063 | cagcacctccagggatctgccc (SEQ ID NO: 66) |
| P0064 | ctggttttcatacagcacgttgcaggtcacgccgattccgttgaatctatagcacatctgcatggcaaaggggatc (SEQ ID NO: 67) |
| P0065 | gatcccctttgccatgcagatgtgctatagattcaacggaatcggcgtgacctgcaacgtgctgtatgaaaaccag (SEQ ID NO: 68) |
| P0066 | gcaggagctcggcaaatacgagcagggatc (SEQ ID NO: 69) |
| P0067 | gccagaagtcagatgctcaaggggc (SEQ ID NO: 70) |
| P0068 | cttctcgaactgggggtgggaccaggcgctatgatggtggtgatg (SEQ ID NO: 71) |
| P0069 | tgataatgactcgagcgataattcactcctcaggtgcaggctgcc (SEQ ID NO: 72) |
| P0070 | atgatggtggtgatggtggtgatggcctgggc (SEQ ID NO: 73) |
| P0071 | cacaggaaacagctatgaccatgattacgccaagct (SEQ ID NO: 74) |
| P0072 | gatccgcccctccactacctcatcacttctcgaactgggggtggg (SEQ ID NO: 75) |
| P0073 | cccaccccagttcgagaagtgatgaggtagtggaggggcggatc (SEQ ID NO: 76) |
| P0074 | ctcgaactgggggtgggaccatcatcaatgatggtggtgatggtggtg (SEQ ID NO: 77) |
| P0075 | caccaccatcaccaccatcattgatgatggtcccaccccagttcgag (SEQ ID NO: 78) |
| P0076 | cagggcgctGGGggtagaggagagggagtcctggatcttg (SEQ ID NO: 79) |
| P0077 | tcctctaccCCCagcgccctgggcaaac (SEQ ID NO: 80) |

TABLE 5

| SARS-CoV-2 Variant Classification and Definitions. |  |
| --- | --- |
| Variant Name (Pango lineage) | Spike Protein Substitutions (see SEQ ID NO: 2) |
| B.1.525 | Q52R, A67V, V70I, Y144V, E484K, D614G, Q677H, F888L |
| B.1.526 | L5F, T95I, D253G, S477N, E484K, D614G, A701V |
| B.1.617.1 | T95I, E154K, L452R, E484Q, D614G, P681R |

TABLE 5-continued

SARS-CoV-2 Variant Classification and Definitions.

| Variant Name (Pango lineage) | Spike Protein Substitutions (see SEQ ID NO: 2) |
|---|---|
| B.1.617.2 | T19R, L452R, T478K, D614G, P681R, D950N |
| P.2 | E484K, D614G, V1176F |
| B.1.1.7 | H69del, V70del, Y144del, N501Y, A570D, D614G, P681H, T716I, S982A, D1118H |
| B.1.351 | D80A, D215G, L242del, A243del, L244del, K417N, E484K, N501Y, D614G, A701V |
| B.1.427 | S131, W152C, W258L, L452R, D614G |
| B.1.429 | S131, P26S, W152C, L452R, D614G |
| P.1 | L18F, T20N, P26S, D138Y, R190S, K417T, E484K, N501Y, D614G, H655Y, T1027I, V1176F |

III. Pharmaceutical Formulations

The present disclosure provides pharmaceutical compositions comprising an engineered Coronavirus S protein, a nucleic acid molecule encoding an engineered Coronavirus S protein, and viral vector comprising an engineered Coronavirus S protein and/or encoding the engineered Coronavirus S protein in its genomic material. Such compositions can be used for stimulating an immune response, such as part of a vaccine formulation.

In the case that a nucleic acid molecule encoding an engineered Coronavirus S protein is used in a pharmaceutical composition, the nucleic acid molecule may comprise or consist of deoxyribonucleotides and/or ribonucleotides, or analogs thereof, covalently linked together. A nucleic acid molecule as described herein generally contains phosphodiester bonds, although in some cases, nucleic acid analogs are included that may have at least one different linkage, e.g., phosphoramidate, phosphorothioate, phosphorodithioate, or O-methylphosphoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. A nucleic acid molecule may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, the term polynucleotide encompasses both the double-stranded form and each of two complementary single-stranded forms known or predicted to make up the double-stranded form. A nucleic acid molecule is composed of a specific sequence of four nucleotide bases: adenine (A), cytosine (C), guanine (G), thymine (T), and uracil (U) for thymine when the polynucleotide is RNA. Thus, the term "nucleic acid sequence" is the alphabetical representation of a nucleic acid molecule. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH3 ("OMe" or "O-methyl"), and 2'-O(CH2)2OCH3 ("MOE"). In certain embodiments, sugar substituents at the 2' position is selected from allyl, amino, azido, thio, O-allyl, O—C1-C10 alkyl, O—C1-C10 substituted alkyl; OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF3, OCF3, O, S, or N(Rm)-alkyl; O, S, or N(Rm)-alkenyl; O, S or N(Rm)-alkynyl; O-alkylenyl-O-alkyl, alkynyl, alkaryl, aralkyl, O-alkaryl, O-aralkyl, O(CH2)2SCH3, O(CH2)2-O—N(Rm)(Rn) or O—CH2-C(=O)—N(Rm) (Rn), where each Rm and Rn is, independently, H, an amino protecting group or substituted or unsubstituted C1-C10 alkyl. These 2'-substituent groups can be further substituted with one or more substituent groups independently selected from hydroxyl, amino, alkoxy, carboxy, benzyl, phenyl, nitro (NO2), thiol, thioalkoxy (S-alkyl), halogen, alkyl, aryl, alkenyl and alkynyl.

In some embodiments, a 2'-substituted nucleoside comprises a 2'-substituent group selected from F, NH2, N3, OCF3, O—CH3, O(CH2)3NH2, CH2-CH=CH2, O—CH2-CH=CH2, OCH2CH2OCH3, O(CH2)2SCH3, O—(CH2)2-O—N(Rm)(Rn), O(CH2)2O(CH2)2N(CH3)2, and N-substituted acetamide (O—CH2-C(=O)—N(Rm)

(Rn) where each Rm and Rn is, independently, H, an amino protecting group or substituted or unsubstituted C1-C10 alkyl.

In some embodiments, a 2'-substituted nucleoside comprises a sugar moiety comprising a 2'-substituent group selected from F, OCF3, O—CH3, OCH2CH2OCH3, O(CH2)2SCH3, O(CH2)2-O—N(CH3)2, —OP(CH2)2O (CH2)2N(CH3)2, and O—CH2-C(═O)—N(H)CH3.

In some embodiments, a 2'-substituted nucleoside comprises a sugar moiety comprising a 2'-substituent group selected from F, O—CH3, and OCH2CH2OCH3.

In some embodiments, nucleosides of the present disclosure comprise one or more unmodified nucleobases. In certain embodiments, nucleosides of the present disclosure comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-amino-propyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyl-adenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluori-nated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., 1991; and those disclosed by Sanghvi, Y. S., 1993.

Representative United States Patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, each of which is herein incorporated by reference in its entirety.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligo-nucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., 1989), cholic acid (Manoharan et al., 1994), a thioether, e.g., hexyl-5-tritylthiol (Manoharan et al., 1992; Manoharan et al., 1993), a thio-cholesterol (Oberhauser et al., 1992), an aliphatic chain, e.g., dodecandiol or undecyl residues (Saison-Behmoaras et al., 1991; Kabanov et al., 1990; Svinarchuk et al., 1993), a phospholipid, e.g., di-hexadecyl-rac-glycerol or triethylam-monium 1,2-di-O-hexadecyl-rac-glycero-3-H-phosphonate (Manoharan et al., 1995; Shea et al., 1990), a polyamine or a polyethylene glycol chain (Manoharan et al., 1995), or adamantane acetic acid (Manoharan et al., 1995), a palmityl moiety (Mishra et al., 1995), or an octadecylamine or hexylamino-carbonyl-oxycholesterol moiety (Crooke et al., 1996). In some aspects, a nucleic acid molecule encoding an engineered Coronavirus S protein is a modified RNA, such as, for example, a modified mRNA. Modified (m)RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In some embodiments, the (m)RNA molecules used herein may have the uracils replaced with psuedouracils such as 1-methyl-3'-pseudouridylyl bases. In some embodiments, some of the uracils are replaced, but in other embodiments, all of the uracils have been replaced. The (m)RNA may comprise a 5' cap, a 5' UTR element, an optionally codon optimized open reading frame, a 3' UTR element, and a poly(A) sequence and/or a polyadenylation signal.

The nucleic acid molecule, whether native or modified, may be delivered as a naked nucleic acid molecule or in a delivery vehicle, such as a lipid nanoparticle. A lipid nanoparticle may comprise one or more nucleic acids present in a weight ratio to the lipid nanoparticles from about 5:1 to about 1:100. In some embodiments, the weight ratio of nucleic acid to lipid nanoparticles is from about 5:1, 2.5:1, 1:1, 1:5, 1:10, 1:15, 1:20, 1:25, 1:30, 1:35, 1:40, 1:45, 1:50, 1:60, 1:70, 1:80, 1:90, or 1:100, or any value derivable therein.

In some embodiments, the lipid nanoparticles used herein may contain one, two, three, four, five, six, seven, eight, nine, or ten lipids. These lipids may include triglycerides, phospholipids, steroids or sterols, a PEGylated lipids, or a group with a ionizable group such as an alkyl amine and one or more hydrophobic groups such as C6 or greater alkyl groups.

In some aspects of the present disclosure, the lipid nanoparticles are mixed with one or more steroid or a steroid derivative. In some embodiments, the steroid or steroid derivative comprises any steroid or steroid derivative. As used herein, in some embodiments, the term "steroid" is a class of compounds with a four ring 17 carbon cyclic structure, which can further comprises one or more substitutions including alkyl groups, alkoxy groups, hydroxy groups, oxo groups, acyl groups, or a double bond between two or more carbon atoms.

In some aspects of the present disclosure, the lipid nanoparticles are mixed with one or more PEGylated lipids (or PEG lipid). In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present disclosure are taught by U.S. Pat. No. 5,820,873, WO 2010/141069, or U.S. Pat. No. 8,450,298, which is incorporated herein by reference.

In some aspects of the present disclosure, the lipid nanoparticles are mixed with one or more phospholipids. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some aspects of the present disclosure, lipid nanoparticle containing compounds containing lipophilic and cationic components, wherein the cationic component is ionizable, are provided. In some embodiments, the cationic ionizable lipids contain one or more groups which is protonated at physiological pH but may deprotonated and has no charge at a pH above 8, 9, 10, 11, or 12. The ionizable cationic group may contain one or more protonatable amines which are able to form a cationic group at physiological pH. The cationic ionizable lipid compound may also further comprise one or more lipid components such as two or more fatty acids with C6-C24 alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

In some aspects of the present disclosure, composition containing compounds containing lipophilic and cationic components, wherein the cationic component is ionizable, are provided. In some embodiments, ionizable cationic lipids refer to lipid and lipid-like molecules with nitrogen atoms that can acquire charge (pKa). These lipids may be known in the literature as cationic lipids. These molecules with amino groups typically have between 2 and 6 hydrophobic chains, often alkyl or alkenyl such as C6-C24 alkyl or alkenyl groups, but may have at least 1 or more that 6 tails.

In some embodiments, the amount of the lipid nanoparticle with the nucleic acid molecule encapsulated in the pharmaceutical composition is from about 0.1% w/w to about 50% w/w, from about 0.25% w/w to about 25% w/w, from about 0.5% w/w to about 20% w/w, from about 1% w/w to about 15% w/w, from about 2% w/w to about 10% w/w, from about 2% w/w to about 5% w/w, or from about 6% w/w to about 10% w/w. In some embodiments, the amount of the lipid nanoparticle with the nucleic acid molecule encapsulated in the pharmaceutical composition is from about 0.1% w/w, 0.25% w/w, 0.5% w/w, 1% w/w, 2.5% w/w, 5% w/w, 7.5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, to about 95% w/w, or any range derivable therein.

In some aspects, the present disclosure comprises one or more sugars formulated into pharmaceutical compositions. In some embodiments, the sugars used herein are saccharides. These saccharides may be used to act as a lyoprotectant that protects the pharmaceutical composition from destabilization during the drying process. These water-soluble excipients include carbohydrates or saccharides such as disaccharides such as sucrose, trehalose, or lactose, a trisaccharide such as fructose, glucose, galactose comprising raffinose, polysaccharides such as starches or cellulose, or a sugar alcohol such as xylitol, sorbitol, or mannitol. In some embodiments, these excipients are solid at room temperature. Some non-limiting examples of sugar alcohols include erythritol, threitol, arabitol, xylitol, ribitol, mannitol, sorbitol, galactitol, fucitol, iditol, inositol, volemitol, isomalt, maltitol, lactitol, maltotritol, maltotetraitol, or a polyglycitol.

In some embodiments, the amount of the sugar in the pharmaceutical composition is from about 25% w/w to about 98% w/w, 40% w/w to about 95% w/w, 50% w/w to about 90% w/w, 50% w/w to about 70% w/w, or from about 80% w/w to about 90% w/w. In some embodiments, the amount of the sugar in the pharmaceutical composition is from about 10% w/w, 15% w/w, 20% w/w, 25% w/w, 30% w/w, 35% w/w, 40% w/w, 45% w/w, 50% w/w, 52.5% w/w, 55% w/w, 57.5% w/w, 60% w/w, 62.5% w/w, 65% w/w, 67.5% w/w, 70% w/w, 75% w/w, 80% w/w, 82.5% w/w, 85% w/w, 87.5% w/w, 90% w/w, to about 95% w/w, or any range derivable therein.

In some embodiments, the pharmaceutically acceptable polymer is a copolymer. The pharmaceutically acceptable polymer may further comprise one, two, three, four, five, or six subunits of discrete different types of polymer subunits. These polymer subunits may include polyoxypropylene, polyoxyethylene, or a similar subunit. In particular, the pharmaceutically acceptable polymer may comprise at least one hydrophobic subunit and at least one hydrophilic subunit. In particular, the copolymer may have hydrophilic subunits on each side of a hydrophobic unit. The copolymer may have a hydrophilic subunit that is polyoxyethylene and a hydrophobic subunit that is polyoxypropylene.

In some embodiments, expression cassettes are employed to express an engineered Coronavirus S protein, either for subsequent purification and delivery to a cell/subject, or for use directly in a viral-based delivery approach. Provided herein are expression vectors which contain one or more nucleic acids encoding an engineered Coronavirus S protein.

Expression requires that appropriate signals be provided in the vectors and include various regulatory elements such as enhancers/promoters from both viral and mammalian sources that drive expression of the an engineered coronavirus S protein in cells. Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

The promoter and/or enhancer may be, for example, immunoglobulin light chain, immunoglobulin heavy chain, T-cell receptor, HLA DQ a and/or DQ β, β-interferon, interleukin-2, interleukin-2 receptor, MHC class II 5, MHC class II HLA-Dra, β-Actin, muscle creatine kinase (MCK), prealbumin (transthyretin), elastase I, metallothionein (MTII), collagenase, albumin, α-fetoprotein, t-globin, β-globin, c-fos, c-HA-ras, insulin, neural cell adhesion molecule (NCAM), α1-antitrypain, H2B (TH2B) histone, mouse and/or type I collagen, glucose-regulated proteins (GRP94 and GRP78), rat growth hormone, human serum amyloid A (SAA), troponin I (TN I), platelet-derived growth factor (PDGF), SV40, polyoma, retroviruses, papilloma virus, hepatitis B virus, human immunodeficiency virus, cytomegalovirus (CMV), and gibbon ape leukemia virus.

Where a cDNA insert is employed, one will typically desire to include a polyadenylation signal to effect proper polyadenylation of the gene transcript. Any polyadenylation sequence may be employed such as human growth hormone and SV40 polyadenylation signals. Also contemplated as an element of the expression cassette is a terminator. These elements can serve to enhance message levels and to minimize read through from the cassette into other sequences.

There are a number of ways in which expression vectors may be introduced into cells. In certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells. These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals.

One method for in vivo delivery involves the use of an adenovirus expression vector. "Adenovirus expression vector" is meant to include those constructs containing adenovirus sequences sufficient to (a) support packaging of the construct and (b) to express engineered Coronavirus S protein that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation. In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

The adenoviruses of the disclosure are replication defective, or at least conditionally replication defective. The adenovirus may be of any of the 42 different known serotypes or subgroups A-F. Adenovirus type 5 of subgroup C is one exemplary starting material that may be used to obtain the conditional replication-defective adenovirus vector for use in the present disclosure.

Other viral vectors may be employed as expression constructs in the present disclosure. Vectors derived from viruses such as vaccinia virus, adeno-associated virus (AAV) and herpesviruses may be employed. They offer several attractive features for various mammalian cells.

In embodiments, particular embodiments, the vector is an AAV vector. AAV is a small virus that infects humans and some other primate species. AAV is not currently known to cause disease. The virus causes a very mild immune response, lending further support to its apparent lack of pathogenicity. In many cases, AAV vectors integrate into the host cell genome, which can be important for certain applications, but can also have unwanted consequences. Gene therapy vectors using AAV can infect both dividing and quiescent cells and persist in an extrachromosomal state without integrating into the genome of the host cell, although in the native virus some integration of virally carried genes into the host genome does occur. These features make AAV a very attractive candidate for creating viral vectors for gene therapy, and for the creation of isogenic human disease models. Recent human clinical trials using AAV for gene therapy in the retina have shown promise. AAV belongs to the genus Dependoparvovirus, which in turn belongs to the family Parvoviridae. The virus is a small (20 nm) replication-defective, nonenveloped virus.

Wild-type AAV has attracted considerable interest from gene therapy researchers due to a number of features. Chief amongst these is the virus's apparent lack of pathogenicity. It can also infect non-dividing cells and has the ability to stably integrate into the host cell genome at a specific site (designated AAVS1) in the human chromosome 19. This feature makes it somewhat more predictable than retroviruses, which present the threat of a random insertion and of mutagenesis, which is sometimes followed by development of a cancer. The AAV genome integrates most frequently into the site mentioned, while random incorporations into the genome take place with a negligible frequency. Development of AAVs as gene therapy vectors, however, has eliminated this integrative capacity by removal of the rep and cap from the DNA of the vector. The desired gene together with a promoter to drive transcription of the gene is inserted between the inverted terminal repeats (ITR) that aid in concatemer formation in the nucleus after the single-stranded vector DNA is converted by host cell DNA polymerase complexes into double-stranded DNA. AAV-based gene therapy vectors form episomal concatemers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency. AAVs also present very low immunogenicity, seemingly restricted to generation of neutralizing antibodies, while they induce no clearly defined cytotoxic response. This feature, along with the ability to infect quiescent cells present their dominance over adenoviruses as vectors for human gene therapy.

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry.

The Inverted Terminal Repeat (ITR) sequences comprise 145 bases each. They were named so because of their symmetry, which was shown to be required for efficient multiplication of the AAV genome. The feature of these sequences that gives them this property is their ability to form a hairpin, which contributes to so-called self-priming that allows primase-independent synthesis of the second DNA strand. The ITRs were also shown to be required for both integration of the AAV DNA into the host cell genome (19th chromosome in humans) and rescue from it, as well as for efficient encapsidation of the AAV DNA combined with generation of a fully assembled, deoxyribonuclease-resistant AAV particles.

With regard to gene therapy, ITRs seem to be the only sequences required in cis next to the therapeutic gene: structural (cap) and packaging (rep) proteins can be delivered in trans. With this assumption many methods were established for efficient production of recombinant AAV (rAAV) vectors containing a reporter or therapeutic gene. However, it was also published that the ITRs are not the only elements required in cis for the effective replication and encapsidation. A few research groups have identified a sequence designated cis-acting Rep-dependent element (CARE) inside the coding sequence of the rep gene. CARE was shown to augment the replication and encapsidation when present in cis.

In some aspects, the present disclosure provides pharmaceutical compositions that contain one or more salts. The salts may be an inorganic potassium or sodium salt such as potassium chloride, sodium chloride, potassium phosphate dibasic, potassium phosphate monobasic, sodium phosphate dibasic, or sodium phosphate monobasic. The pharmaceutical composition may comprise one or more phosphate salts such to generate a phosphate buffer solution. The phosphate buffer solution may be comprise each of the phosphates to buffer a solution to a pH from about 6.8, 6.9, 7.0, 7.1, 7.2, 7.3, 7.4, 7.5, 7.6, 7.7, 7.8, 7.9, or 8.0, or any range derivable therein.

In some aspects, the present disclosure comprises one or more excipients formulated into pharmaceutical compositions. An "excipient" refers to pharmaceutically acceptable carriers that are relatively inert substances used to facilitate administration or delivery of an API into a subject or used to facilitate processing of an API into drug formulations that can be used pharmaceutically for delivery to the site of action in a subject. Furthermore, these compounds may be used as diluents in order to obtain a dosage that can be readily measured or administered to a patient. Non-limiting examples of excipients include polymers, stabilizing agents, surfactants, surface modifiers, solubility enhancers, buffers, encapsulating agents, antioxidants, preservatives, nonionic wetting or clarifying agents, viscosity increasing agents, and absorption-enhancing agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and can preferably include an adjuvant. Water is a particular carrier when the pharmaceutical composition is administered by injections, such an intramuscular injection. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Engineered proteins or nucleic acids encoding engineered proteins of the present disclosure, as described herein, can be formulated for parenteral administration, e.g., formulated for injection via the intradermal, intravenous, intramuscular, subcutaneous, intra-tumoral or even intraperitoneal routes. The formulation could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Dosage can be by a single dose schedule or a multiple dose schedule. Multiple doses may be used in a primary immunization schedule and/or in a booster immunization schedule. In a multiple dose schedule the various doses may be given by the same or different routes. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The compositions disclosed herein may be used to treat both children and adults. Thus, a human subject may be less than 1 year old, 1-5 years old, 5-16 years old, 16-55 years old, 55-65 years old, or at least 65 years old.

Preferred routes of administration include, but are not limited to, intramuscular, intraperitoneal, intradermal, subcutaneous, intravenous, intraarterial, and intraoccular injection. Particularly preferred routes of administration include intramuscular, intradermal and subcutaneous injection.

IV. Immunodetection Methods

In still further embodiments, the present disclosure concerns immunodetection methods for binding, purifying, removing, quantifying and otherwise generally detecting Coronavirus S protein. While such methods can be applied in a traditional sense, another use will be in quality control and monitoring of vaccine stocks, where antibodies according to the present disclosure can be used to assess the amount or integrity (i.e., long term stability) of antigens. Alternatively, the methods may be used to screen various antibodies for appropriate/desired reactivity profiles.

Some immunodetection methods include enzyme linked immunosorbent as say (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Coronavirus S protein also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Coronavirus S protein, and contacting the sample with a first antibody in accordance with the present disclosure, as the case may be, under conditions effective to allow the formation of immunocomplexes.

These methods include methods for detecting or purifying Coronavirus S protein or Coronavirus S protein from a sample. The antibody will preferably be linked to a solid support, such as in the form of a column matrix, and the sample suspected of containing the Coronavirus S protein will be applied to the immobilized antibody. The unwanted components will be washed from the column, leaving the Coronavirus S protein-expressing cells immunocomplexed to the immobilized antibody, which is then collected by removing the organism or antigen from the column.

The immunobinding methods also include methods for detecting and quantifying the amount of Coronavirus S protein or related components in a sample and the detection and quantification of any immune complexes formed during the binding process. Here, one would obtain a sample suspected of containing Coronavirus S protein and contact the sample with an antibody that binds Coronavirus S protein or components thereof, followed by detecting and quantifying the amount of immune complexes formed under the specific conditions. In terms of antigen detection, the biological sample analyzed may be any sample that is suspected of containing Coronavirus S protein, such as a tissue section or specimen, a homogenized tissue extract, a biological fluid (e.g., a nasal swab), including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Coronavirus S protein. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Coronavirus S protein is added to the wells. After binding and washing to remove non-specifically bound immune complexes, the bound antigen may be detected. Detection may be achieved by the addition of another anti-Coronavirus S protein antibody that is linked to a detectable label. This type of ELISA is a simple "sandwich ELISA." Detection may also be achieved by the addition of a second anti-Coronavirus S protein antibody, followed by the addition of a third antibody that has binding affinity for the second antibody, with the third antibody being linked to a detectable label.

In another exemplary ELISA, the samples suspected of containing the Coronavirus S protein (e.g., potentially infected cells) are immobilized onto the well surface and then contacted with the anti-Coronavirus S protein antibodies of the disclosure. After binding and washing to remove non-specifically bound immune complexes, the bound anti-Coronavirus S protein antibodies are detected. Where the initial anti-Coronavirus S protein antibodies are linked to a detectable label, the immune complexes may be detected directly. Again, the immune complexes may be detected using a second antibody that has binding affinity for the first anti-Coronavirus S protein antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Coronavirus S protein, the antibodies may be included in the kit. The immunodetection kits will thus comprise, in suitable container means, a first antibody that binds to an Coronavirus S protein, and optionally an immunodetection reagent.

In certain embodiments, the antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of Coronavirus S protein, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis disorders, especially blood cancers, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Engineering of the SARS-CoV-2 Spike Protein

A. Methods

Design scheme for pre fusion stabilized nCoV spike variants. The SARS-CoV-2 S-2P variant was used as the base construct for all subsequent design[20]. The S-2P base construct comprises residues 1-1208 of SARS-CoV-2 S (GenBank: MN908947) with proline substituted at residues 986 and 987, "GSAS" substituted at the furin cleavage site (residues 682-685), the trimerization foldon motif of T4 fibritin, an HRV3C protease recognition site, a Twin-Strep-tag and an octa-histidine tag in the mammalian expression plasmid pαH. Using this plasmid as a template, desired mutations were introduced at selected positions within SARS-CoV-2 S gene. Based on the cryo-EM structure, pairs of residues with beta-carbon atoms less than 4.6 Å apart were considered for disulfide design. Regions that move drastically during the pre- to post-fusion transition were particularly targeted such as the FP, CR and HR1. Salt bridge variants required that the charged groups of the mutated residues were predicted to be within 4.0 Å. For residues in loops, a slightly longer distance than 4.0 Å was allowed. Core-facing residues with sidechains contiguous to a preexisting internal cavity were examined for potential substitutions to a bulkier cavity-filling residues. Proline substitutions were designed in the FP, CR, or HR1 and placed either in a flexible loop or at the N-terminus of a helix. All desired substitutions maximized avoidance of: 1. creating clashes with neighboring residues, 2. creating larger hydrophobic cavities, 3. losing polar interactions with neighboring residues, 4. unfavorable dihedral angles, 5. losing existing or creating new N-glycosylation sites. Combinations were chosen in order to test whether pairs of the same type of design (i.e. disulfide/disulfide) or different types of designs (e.g. disulfide/proline) could result in additive effects on spike expression and stability. Substitutions predicted to potentially interfere with one another, such as a proline that could restrict the flexibility of an adjacent cysteine involved in the formation a disulfide bond, were avoided.

Protein expression and purification. Plasmids encoding S variants were transiently transfected into FreeStyle293F cells (Thermo Fisher) using polyethyleneimine Four days after transfection, cultures were harvested and the medium was separated from the cells by centrifugation. Supernatants were passed through a 0.22 μm filter, then over StrepTactin resin (IBA). S variants were further purified by size exclusion chromatography using a Superose 6 10/300 column (GE Healthcare) in a buffer composed of 2 mM Tris pH 8.0, 200 mM NaCl and 0.02% NaN$_3$. For initial purification and characterization, single-substitution and Combo S variants were purified from 40 mL cultures. The HexaPro variant was purified from a 2 L culture.

Differential scanning fluorimetry. In a 96-well qPCR plate, solutions were prepared with a final concentration of 5×SYPRO Orange Protein Gel Stain (ThermoFisher) and 0.25 mg/mL spike. Continuous fluorescence measurements ($\lambda_{ex}$=465 nm, $\lambda_{em}$=580 nm) were performed using a Roche LightCycler 480 II, using a temperature ramp rate of 4.4°/minute, increasing from 25° C. to 95° C. Data were plotted as the derivative of the melting curve.

Negative stain EM. Purified 2019-nCoV S variants were diluted to a concentration of 0.04 mg/mL in 2 mM Tris pH 8.0, 200 mM NaCl and 0.02% NaN$_3$. Each protein was deposited on a CF-400-CU grid (Electron Microscopy Sciences) that had been plasma cleaned for 30 seconds in a Solarus 950 plasma cleaner (Gatan) with a 4:1 ratio of O$_2$/H$_2$ and stained using methylamine tungstate (Nanoprobes). Grids were imaged at a magnification of 92,000×(corresponding to a calibrated pixel size of 1.63 Å/pix) in a Talos F200C TEM microscope equipped with a Ceta 16M detector (Thermo Fisher Scientific). Stability experiments with S-2P and HexaPro were performed by imaging samples as above after 3 rounds of snap freezing with liquid nitrogen and thawing, after storing samples at room temperature for 1-2 days, or after incubating at 50° C., 55° C., or 60° C. for 30 minutes.

Biolayer interferometry for quantification of protein expression. FreeStyle293F cells (Thermo Fisher) were transfected in 3 mL minimal media and harvested four days after transfection. After centrifugation, supernatant was diluted 5-fold with buffer composed of 10 mM HEPES pH 7.5, 150 mM NaCl, 3 mM EDTA, 0.05% Tween 20 and 1 mg/mL bovine serum albumin. Anti-foldon IgG was immobilized to an anti-human capture (AHC) sensortip (FortéBio) using an Octet RED96e (FortéBio). The sensortip was dipped into wells containing individual spike variants. A standard curve was determined by measuring 2-fold serial dilutions of purified S-2P at concentrations ranging from 10 μg/mL to 0.16 μg/mL. The data were reference-subtracted, aligned to a baseline after IgG capture and quantified based on a linear fit of the initial slope each association curve using Octet Data Analysis software v11.1.

Surface plasmon resonance. His-tagged HexaPro was immobilized to a NiNTA sensorchip (GE Healthcare) to a level of ~800 response units (RUs) using a Biacore X100 (GE Healthcare) and running buffer composed of 10 mM HEPES pH 8.0, 150 mM NaCl and 0.05% Tween 20. Serial dilutions of purified hACE2 were injected at concentrations ranging from 250 to 15.6 nM. Response curves were fit to a 1:1 binding model using Biacore X100 Evaluation Software (GE Healthcare).

Cryo-EM sample preparation and data collection. Purified HexaPro was diluted to a concentration of 0.35 mg/mL in 2 mM Tris pH 8.0, 200 mM NaCl, 0.02% NaN$_3$ and applied to plasma-cleaned CF-400 1.2/1.3 grids before being blotted for 6 seconds in a Vitrobot Mark IV (ThermoFischer) and plunge frozen into liquid ethane. Micrographs were collected from a single grid using a FEI Titan Krios (ThermoFischer) equipped with a K3 direct electron detector (Gatan). Data were collected at a magnification of 46,296×, corresponding to a calibrated pixel size of 1.08 Å/pix. A full description of the data collection parameters can be found in Table S5.

Cryo-EM data processing. Motion correction, CTF-estimation and particle picking were performed in Warp[33]. Particles were then imported into cryoSPARC v2.15.0 for 2D classification, ab initio 3D reconstruction, heterogeneous 3D refinement and non-uniform homogeneous refinement[34]. Iterative model building and refinement were performed Coot, Phenix and ISOLDE[35-37].

B. Results

Figure 1:
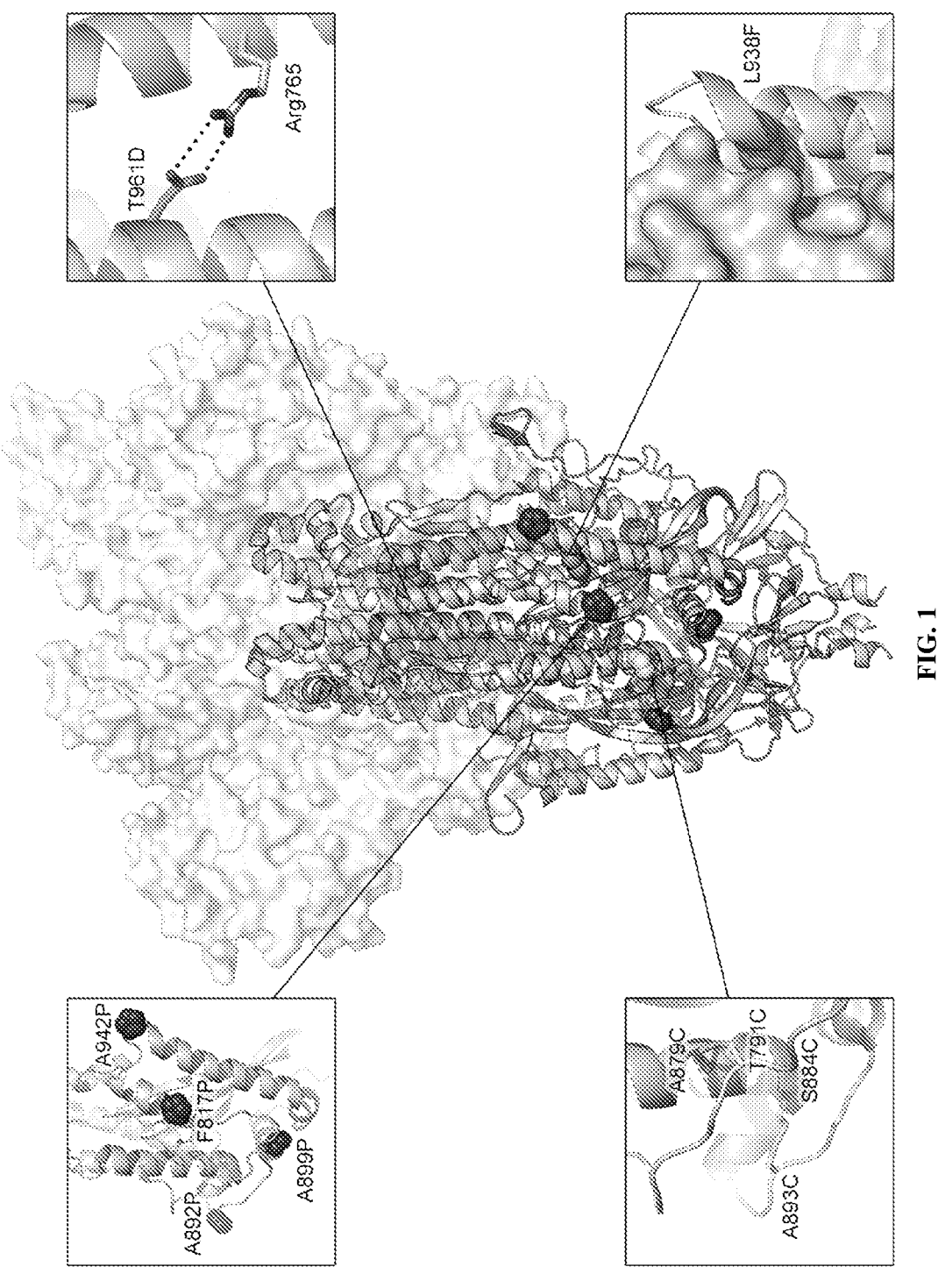
FIG. 1 shows exemplary substitutions for SARS-CoV-2 spike stabilization. Side view of the trimeric SARS-CoV-2 spike ectodomain in a prefusion conformation (PDB ID.

Structure-based design of prefusion-stabilized SARS-CoV-2 spikes. To generate a prefusion-stabilized SARS-CoV-2 spike protein that expresses better and is more stable than the original S-2P variant[20], the SARS-CoV-2 S-2P cryo-EM structure (PDB: 6VSB) was analyzed and substitutions designed based upon knowledge of class I fusion protein function and general protein stability principles. These strategies included the introduction of disulfide bonds to prevent conformational changes during the pre-to-postfusion transition, salt bridges to neutralize charge imbalances, hydrophobic residues to fill internal cavities and prolines to cap helices or stabilize loops in the prefusion state. 100 single S-2P variants were cloned and characterized their relative expression levels, and for those that expressed well, their monodispersity, thermostability, and quaternary structure were characterized (Table 6). Given that the S2 subunit undergoes large-scale refolding during the pre-to-postfusion transition, efforts were concentrated on stabilizing S2. Substitutions of each category were identified that increased expression while maintaining the prefusion conformation (FIGS. 1 & 2A). Overall, 28 out of the 100 variants expressed better than S-2P and retained the prefusion conformation as assessed by negative-stain EM.

TABLE 6

| Mutation(s) | Strategy | Fold change in expression relative to S-2P |
|---|---|---|
| T547C, N978C | Disulfide | 0[b] |
| A570C, V963C | Disulfide | 0[b] |
| S659C, S698C | Disulfide | 0.4[a] |
| Replace (673-686) with GS | Remove flexible region | 0[b] |
| Replace (673-686) with GS + A672C, A694C | Disulfide, Remove flexible region | <0.5[b] |
| N703Q, V705C, A893C | Disulfide | <0.5[b] |
| V705C, A893C | Disulfide | <0.5[b] |
| A713S | H bond | 1.0[a] |
| V722C, A930C | Disulfide | <0.1[b] |
| T724M | Cavity-filling | 1.3[a] |
| L727C, S1021C | Disulfide | <0.5[b] |
| P728C, V951C | Disulfide | 0[b] |
| V729C, A1022C | Disulfide | <0.1[a] |
| S730L | Cavity-filling | 0[b] |
| S730R | Salt bridge | 0.15[a] |
| S735C, T859C | Disulfide | <0.5[b] |
| V736C, L858C | Disulfide | 0[b] |
| T752K | Salt bridge | <0.5[b] |
| A766E | Salt bridge | <0.5[b] |
| G769E | Salt bridge | 3.0[a] |
| I770C, A1015C | Disulfide | <0.5[b] |
| T778Q | Hydrogen bond | 2.6[a] |
| T778L | Cavity-filling | 1.5[a] |
| T791C, A879C | Disulfide | 1.0[b] |
| G799C, A924C | Disulfide | 1.3[a] |
| P807C, S875C | Disulfide | 1.1[a] |
| F817P | Proline | 2.9[a] |
| E819C, S1055C | Disulfide | 0[b] |
| E819C, Q1054C | Disulfide | 0[b] |
| L822C, A1056C | Disulfide | 0[b] |
| V826L | Cavity-filling | 1.0[b] |
| L828K | Salt bridge | 0.8[a] |
| L828R | Salt bridge | 0.4[a] |
| A(829-851) | Remove flexible region | <0.5[b] |
| T859K | Salt bridge | 2.1[a] |
| P862E | Salt bridge | <0.5[b] |
| L865P, Q779M | Proline, cavity-filling | <0.5[b] |
| T866P | Proline | <0.5[b] |
| I870C, S1055C | Disulfide | 0[b] |
| T874C, S1055C | Disulfide | <0.5[b] |
| S875F | Cavity-filling | <0.5[b] |
| S884C, A893C | Disulfide | 2[a] |
| G885C, Q901C | Disulfide | 1.1[a] |
| G889C, L1034C | Disulfide | <0.1[a] |
| A890V | Cavity-filling | 1.0[b] |
| A892P | Proline, cavity-filling | 1.5[a] |
| A893P | Proline | 1.5[b] |
| L894F | Cavity-filling | 0.9[a] |
| Q895P | Proline | 2.1[b] |
| I896C, Q901C | Disulfide | 0[b] |
| A899F | Cavity-filling | 0.3[b] |
| A899P | Proline, Cav | 1.5[a] |
| Q901M | Cavity-filling | 0.9[a] |
| A903C, Q913C | Disulfide | 2.3[b] |
| V911C, N1108C | Disulfide | 0[b] |
| T912R | Salt bridge | <0.5[b] |
| T912P | Proline cavity-filling | 2.5[a] |
| K921P | Proline | 1.1[b] |
| L922P | Proline | 0.8[b] |
| L938F | Cavity-filling | 2.5[a] |
| A942P | Proline | 4.0[a] |
| A944F | Cavity-filling | 1.0[a] |
| A944F, T724I | Cavity-filling | 0.4[a] |
| A944Y | Cavity-filling | 1.9[b] |
| G946P | Proline | 1.0[b] |
| Q957E | Salt bridge | 1.0[a] |
| T961D | Salt bridge | 1.8[a] |
| T961C,S758C | Disulfide | 0[b] |
| T961C, Q762C | Disulfide | 0[b] |

TABLE 6-continued

| Mutation(s) | Strategy | Fold change in expression relative to S-2P |
|---|---|---|
| V963L | Cavity-filling | 1.9[a] |
| Q965C, S1003C | Disulfide | 2[a] |
| A972C, Q992C | Disulfide | 1[a] |
| A972C, I980C | Disulfide | 1.3[a] |
| S974C, D979C | Disulfide | 0.3[b] |
| S975P | Proline | 2.2[b] |
| N978P | Proline | 0.9[b] |
| I980C, Q992C | Disulfide | 2.0[a] |
| R1000Y | Cavity-filling + hydrogen bond | 0.3[a] |
| R1000W | Cavity-filling | 1.0[a] |
| S1003V | Cavity-filling | 1.9[b] |
| I1013F | Cavity-filling | 0.8[a] |
| R1039F | Charge removal, pi-pi stacking | 0.5[b] |
| V1040F | Cavity-filling | <0.5[b] |
| V1040Y | Cavity-filling | 0.3[a] |
| H1058W | Cavity-filling | <0.5[b] |
| H1058F | Cavity-filling | 0[b] |
| H1058Y | Cavity-filling | 0.3[a] |
| A1078C, V1133C | Disulfide | <0.5[b] |
| A1080C, H132C | Disulfide | <0.5[b] |
| I1081C, N1135C | Disulfide | 0.3[a] |
| H1088Y | Cavity-filling | 1.6[a] |
| H1088W | Cavity-filling | 0.6[a] |
| F1103C, P1112C | Disulfide | 0.15[a] |
| VI1041 | Cavity-filling | 0.7[a] |
| T1116C, Y1138C | Disulfide | 0[b] |
| T1117C,D1139C | Disulfide | 1.0[a] |
| D1118F | Charge removal, pi-pi stacking | 0.5[b] |
| I113OY | Hydrogen bond | 0[b] |
| L1141F | Cavity-filling | 0.8[a] |
| AHR2 (A1161-1208) | Remove flexible region | 2.5[a] |

Figures 2E, 2F, 2G:
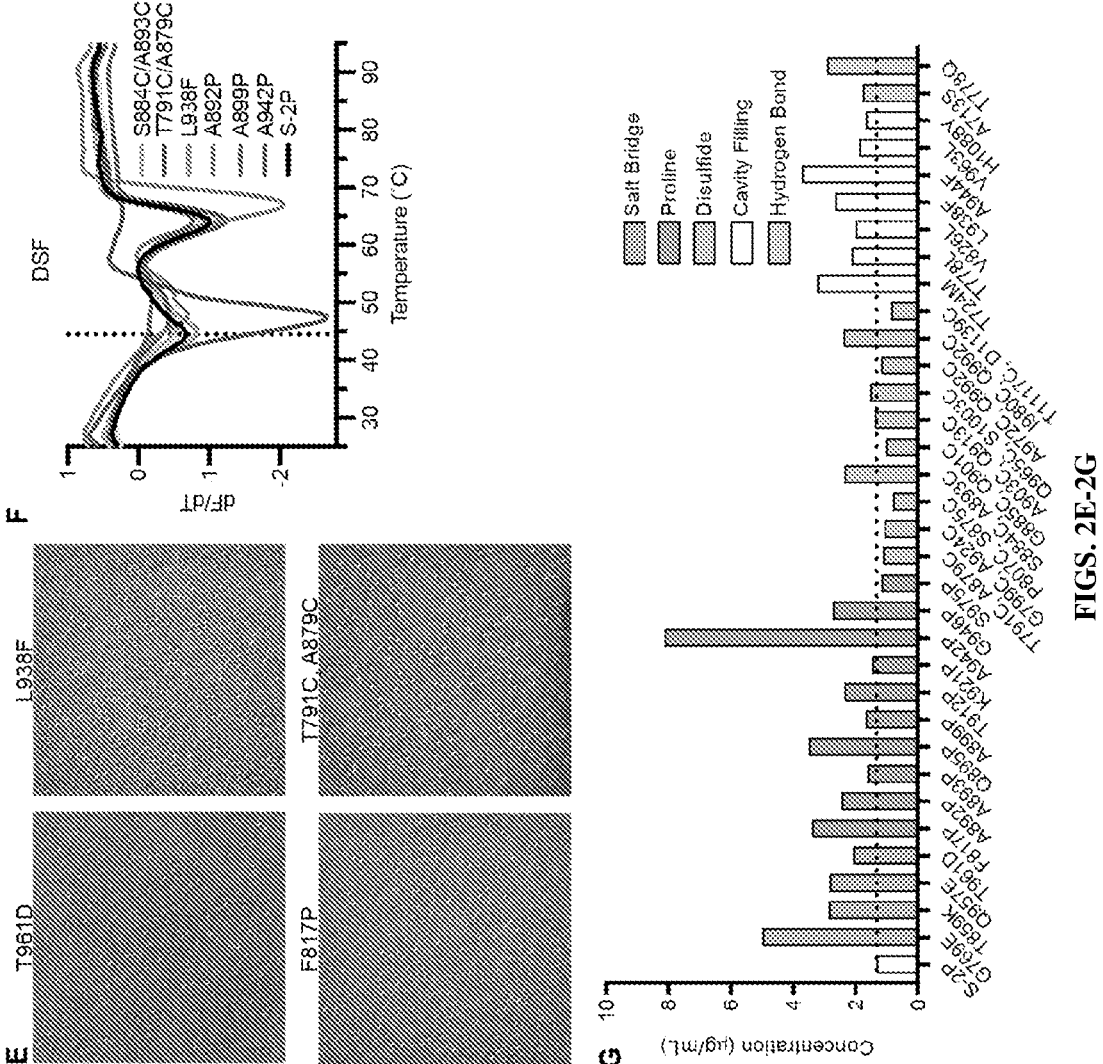

[a]Quantified using the area under the curve of the size-exclusion trimer peak
[b]Quantified using SDS-PAGE band intensity Single-substitution spike variants. Although the introduction of disulfide bonds requires two substitutions, they are considered as single substitutions for these purposes. One common strategy to stabilize class I fusion proteins such as the spike is to covalently link via disulfide bonds a region that undergoes a conformational change to a region that does not. For instance, the Q965C/S1003C substitution attempts to link HR1 to the central helix, whereas G799C/A924C aims to link HR1 to the upstream helix. These two variants boosted protein expression 3-fold and 2-fold, respectively, compared to S-2P (FIG. 2B). However, the size-exclusion chromatography (SEC) traces of both variants showed a leftward shift compared to S-2P, indicating that the proteins are running larger than expected, which agreed well with negative stain electron microscopy (nsEM) results that showed partially misfolded spike particles. By contrast, S884C/A893C and T791C/A879C variants eluted on SEC at a volume similar to S-2P and appeared as well-folded trimeric particles by nsEM (FIG. 2E). These variants link the same α-helix to two different flexible loops that pack against a neighboring protomer (FIG. 1). Notably, S884C/A893C had two-fold higher expression than S-2P and also increased the thermostability (FIG. 2F).

The introduction of select cavity-filling substitutions and salt bridges should improve protein stability without disturbing the overall fold. Cavity filling has been particularly helpful in stabilizing the prefusion conformations of RSV F and HIV-1 Env[15,22] Here, it was found that many cavity-filling and salt bridge designs improved protein expression compared to S-2P (FIG. 2G). For example, L938F and T961D both had ~2-fold increases in protein yields and also maintained the correct quaternary structures of the spikes (FIGS. 2C & 2E), although the thermostability of both variants as assessed by differential scanning fluorimetry (DSF) stayed the same as S-2P (FIG. 2F).

Previous successes using proline substitutions inspired us to try 14 individual variants wherein a proline was substituted into flexible loops or the N-termini of helices in the fusion peptide (FP), the connector region (CR) and HR1 (Table 1 and FIG. 1G). As expected, multiple proline variants boosted the protein expression and increased the thermostability (FIGS. 2D & 2F). Two of the most successful substitutions, F817P and A942P, exhibited 2.3 and 4-fold increases in protein yield, respectively, as opposed to S-2P. The A942P substitution further increased the melting temperature (Tm) by ~3° C., and both variants appeared as well-folded trimers by nsEM (FIG. 2E).

Multiple-substitution spike variants. To examine the potential additive or synergistic effects of beneficial single substitutions, initial combination ("Combo") variants were generated with the following considerations: substitutions should not be in proximity to each other in space and at most two disulfide bonds per construct. The Combo variants containing two disulfide bonds generally had expression levels that were ~50% of the single disulfide variants, suggesting that the two substitutions interfered with each other (Table 2). Adding one disulfide (S884C/A893C) to a single proline variant (F817P) also reduced the expression level, although the quaternary structures of the spikes were well maintained (Table 7). The beneficial effect of a disulfide bond was most prominent when combined with L938F, a cavity-filling variant. Combo23 (S884C, A893C, L938F) had higher protein yields than either of its parental variants, but the Tm of Combo23 did not further increase compared to S884C/A893C. In addition, combining two cavity-filling substitutions (Combo18) or mixing one cavity-filling substitution with one proline substitution (Combo20) increased the expression compared to L938F alone (Table 7).

TABLE 7

| Combo # | Mutation(s) | Strategy | Fold change in expression relative to S-2P |
|---|---|---|---|
| Combo1 | A903C, Q913C, Q965C, S1003C | Disulfide + Disulfide | 3.3 |
| Combo2 | S884C, A893C, A903C, Q913C | Disulfide + Disulfide | N.D. |
| Combo3 | T791C, A879C, A903C, Q913C | Disulfide + Disulfide | N.D. |
| Combo4 | G799C, A924C, A903C, Q913C | Disulfide + Disulfide | N.D. |
| Combo8 | T791C, A879C, S884C, A893C | Disulfide + Disulfide | 0.5 |
| Combo9 | G799C, A924C, S884C, A893C | Disulfide + Disulfide | 0.4 |
| Combo11 | A892P, A899P | Proline + Proline | 1.9 |

TABLE 7-continued

| Combo # | Mutation(s) | Strategy | Fold change in expression relative to S-2P |
|---|---|---|---|
| Combo12 | A892P, T912P | Proline + Proline | 2.7 |
| Combo14 | A892P, A942P | Proline + Proline | 6.2 |
| Combo16 | A899P, A942P | Proline + Proline | 5.1 |
| Combo18 | L938F, V963L | Cavity-filling + Cavity-filling | 1.9 |
| Combo19 | L938F, A892P | Cavity-filling + Proline | 3.0 |
| Combo20 | L938F, A899P | Cavity-filling + Proline | 3.0 |
| Combo21 | F817P, L938F | Proline + Proline | 3.9 |
| Combo22 | L938F, A942P | Cavity-filling + Proline | 6.0 |
| Combo23 | S884C, A893C, L938F | Disulfide + Cavity-filling | 2.9 |
| Combo24 | T791C, A879C, L938F | Disulfide + Cavity-filling | 2.2 |
| Combo26 | L938F, A903C, Q913C | Cavity-filling + Disulfide | 2.0 |
| Combo40 | F817P, S884C, A893C | Proline + Disulfide | 2.0 |
| Combo42 | T791C, A879C, F817P | Disulfide + Proline | 1.4 |
| Combo45 | A892P, A899P, A942P | 3X Proline | 6.2 |
| Combo46 | F817P, A892P, A899P | 3X Proline | 3.8 |
| Combo47 | F817P, A892P, A899P, A942P | 4X Proline | 9.8 |

Figures 3A, 3B, 3C, 3D:
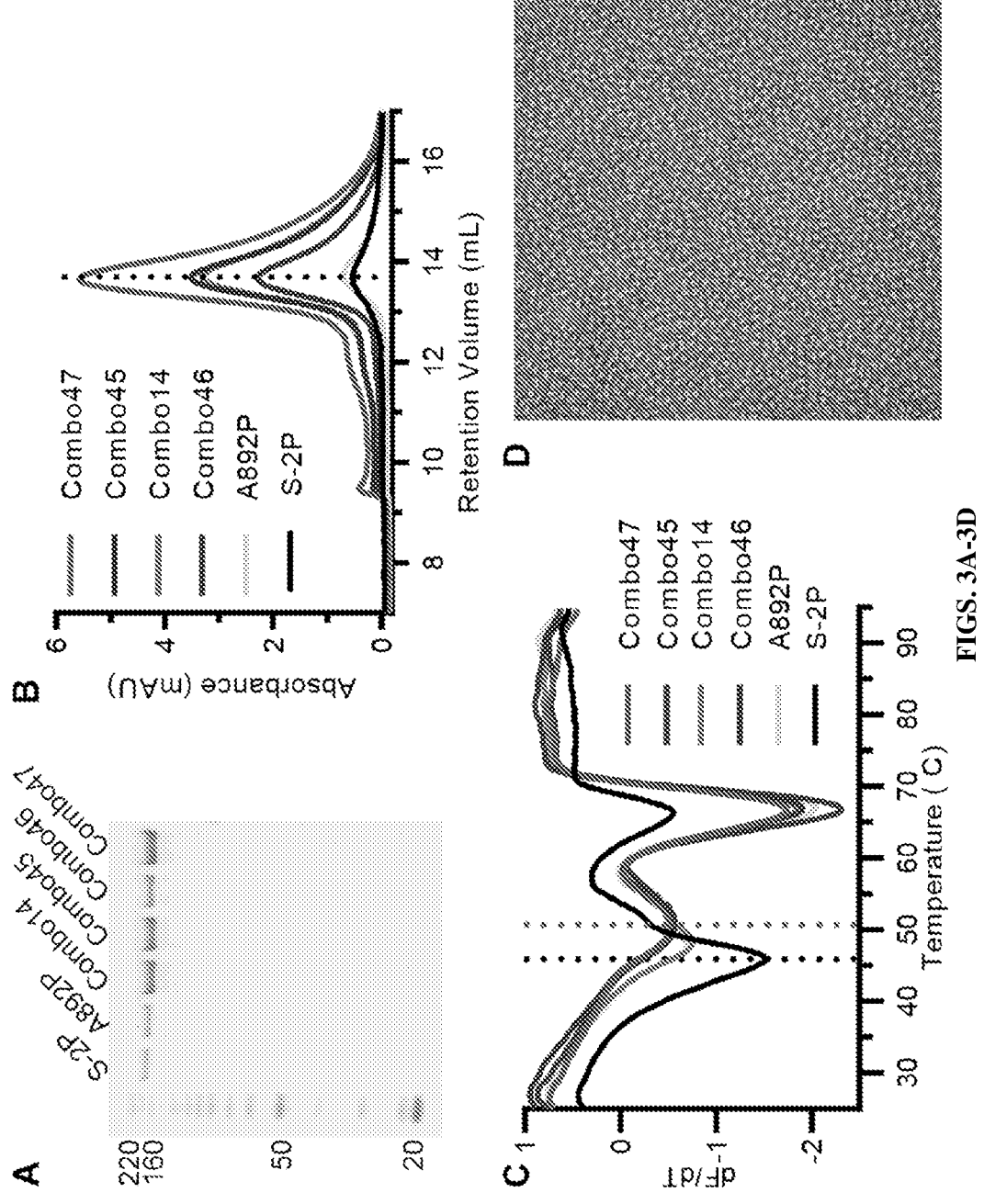

The most striking results came from the combination of multiple proline substitutions (FIG. 3A). Combo14, containing A892P and A942P, had a 6.2-fold increase in protein yield compared to A892P alone (FIGS. 3B and 3C). With A899P added to Combo14, Combo45 appeared to have the same expression level as Combo14 but a +1.2° C. Tm (FIG. 3C). Combo46 is the combination of A892P, A899P and F817P, and it had a 3.4-fold increase in protein yield and a 3.3° C. rise in Tm as compared to A892P. On top of the original S-2P, Combo47 contains all four beneficial proline substitutions, which not only boosts the protein expression 9.8-fold higher than S-2P, but also stabilizes the protein with an ~5° C. increase in Tm. Most importantly, all Combo variants with proline substitutions were well-folded trimers as revealed by nsEM (FIG. 3E). Combo47 was renamed to HexaPro as it contains a total of six proline substitutions and is the best construct to date.

Figures 4A, 4B, 4C, 4D, 4E, 4F:
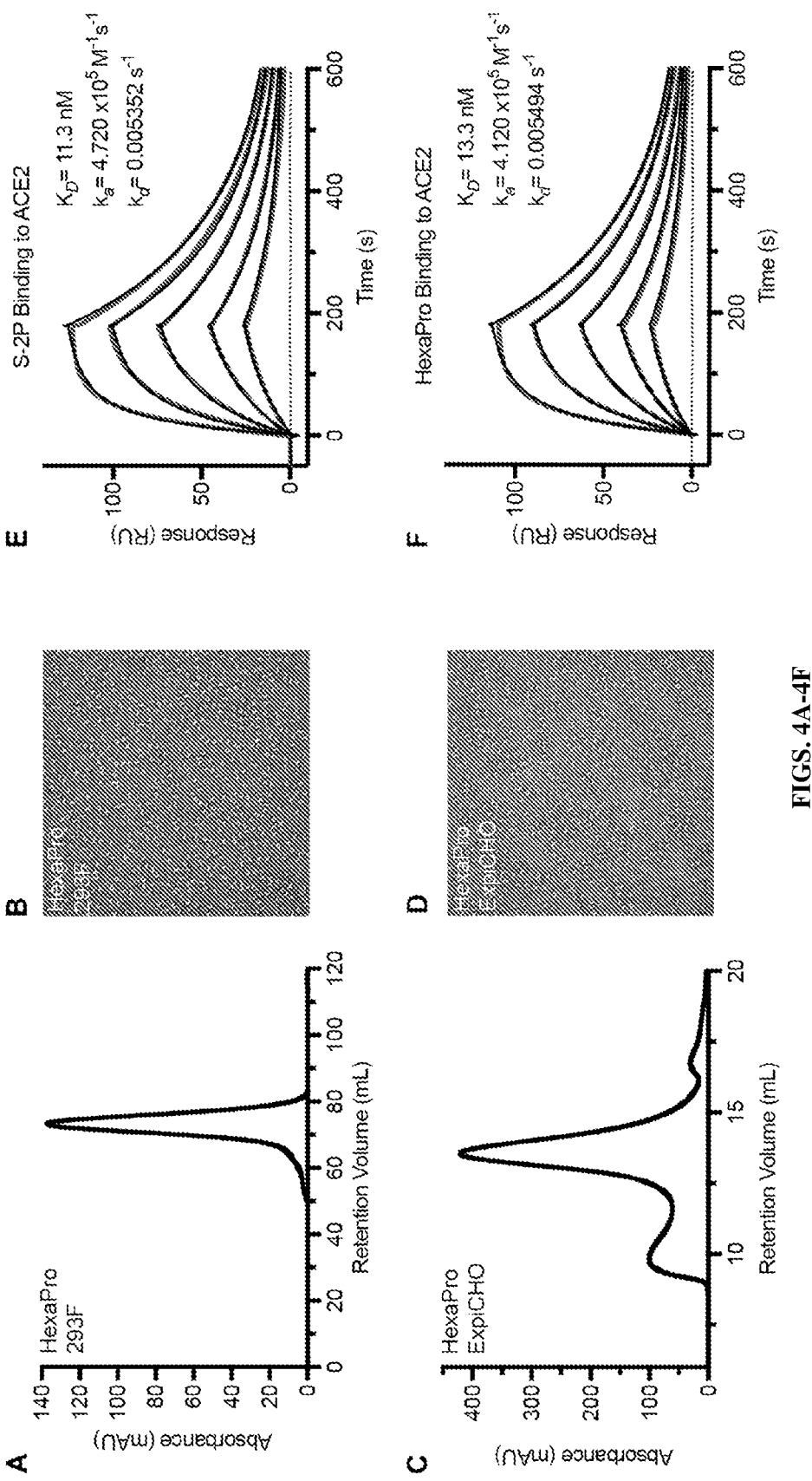
Figures 4G, 4H:
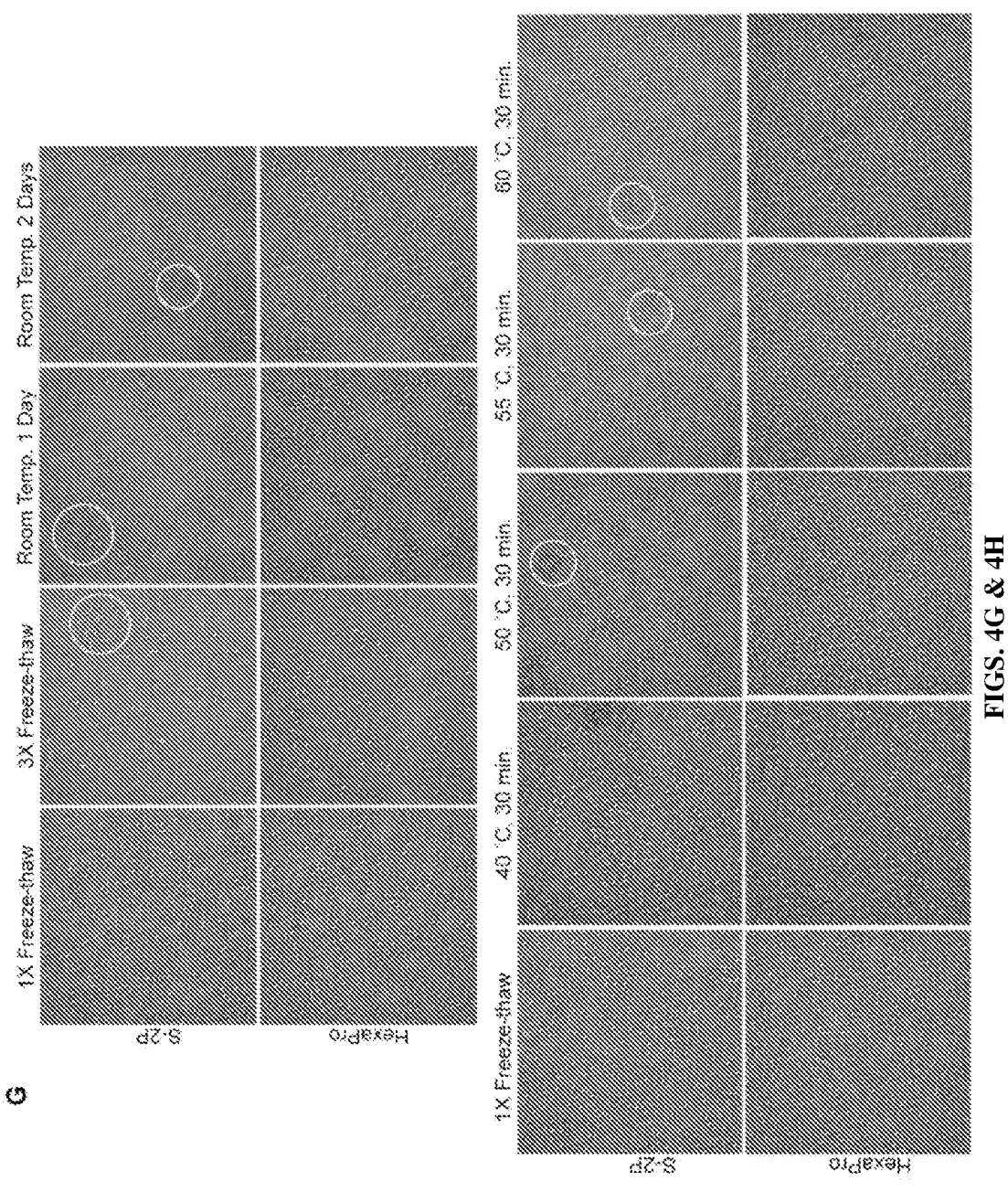

HexaPro Large-scale Expression and Stress Testing. To assess the viability of HexaPro as a potential vaccine antigen or diagnostic reagent, large-scale production in FreeStyle 293 cells, feasibility of protein expression in ExpiCHO cells, epitope integrity and protein stability were comprehensively examined ~12 mg of HexaPro was generated from 2 L of FreeStyle 293 cells, or 6 mg/L, which represents a greater than 10-fold improvement over S-2P. The SEC profile of the large-scale HexaPro preparation was a monodisperse peak, corresponding to the size of a trimer (FIG. 4A). The quaternary structure of HexaPro was also well maintained, indistinguishable from S-2P based on nsEM (FIG. 4B). Conventionally, industrial production of recombinant proteins relies on CHO cells rather than HEK293 cells, and thus the expression of HexaPro in ExpiCHO cells was investigated via transient transfection. ExpiCHO cells produced 1.3 mg of HexaPro per 40 mL of culture, or 32.5 mg/L, and the protein was well folded (FIGS. 4C & 4D). The binding kinetics of HexaPro to its natural receptor human ACE2 were also comparable to that of S-2P (FIGS. 4F & 4E), with affinities of 13.3 nM and 11.3 nM, respectively. Importantly, HexaPro remained folded in the prefusion conformation after 3 cycles of freeze-thaw, 2 days incubation at room temperature or 30 minutes at 55° C. (FIGS. 4G & 4H). In contrast, S-2P showed signs of aggregation after 3 cycles of freeze-thaw, and began unfolding after 30 min at 50° C. Collectively, these data indicate that HexaPro possesses optimal characteristics and suggest it could be a promising candidate for SARS-CoV-2 vaccine development.

Cryo-EM Structure of SARS-CoV-2 S HexaPro. To confirm that stabilizing substitutions did not lead to any unintended conformational changes, it was determined the cryo-EM structure of SARS-CoV-2 S HexaPro. From a single grid, high-resolution 3D reconstructions for two distinct conformations of S were obtained: one with a single RBD in the up conformation and the other with two RBDs in the up conformation. This two-RBD-up conformation was not observed during previous structural characterization of SARS-CoV-2 S-2P and while it is tempting to speculate that the enhanced stability of S2 in HexaPro allowed for the observation of this less stable intermediate, validating this hypothesis will require further investigation. Roughly a third (30.6%) of the particles observed were in the two RBD up conformation, leading to a 3.20 Å reconstruction. The remaining particles were captured in the one-RBD-up conformation, although some flexibility in the position of the receptor-accessible RBD prompted us to remove a subset of one-RBD-up particles that lacked clear density for this domain, resulting in a final set of 85,675 particles that led to a 3.21 Å reconstruction (FIG. 5A). Comparison of the one-RBD-up HexaPro structure with the previously determined 3.46 Å S-2P structure is illustrated in FIG. 5B. The relatively high resolution of this reconstruction also allowed us to observe density at all four of the positions containing the stabilizing proline substitutions, confirming that each of the substitutions was properly introduced into the spike protein and that these substitutions did not have any deleterious effects on the conformation of the S2 subunit (FIG. 5C).

C. Discussion

Prefusion-stabilized class I viral fusion proteins, in general, induce more potent neutralizing antibodies and function as better vaccine antigens than their unstabilized counterparts[15,23]. To respond to the urgent needs for preventative countermeasures against the COVID-19 pandemic, a prefusion-stabilized SARS-CoV-2 S-2P structure[20] was used as a guide to design 100 single substitution variants intended to have increased expression or stability. Given that the S2 subunit, like HIV-1 gp41 or RSV F, undergoes large-scale refolding to facilitate membrane fusion, efforts were specifically focused on this portion of the spike. One of the strategies employed was the introduction of disulfide bonds wherein at least one cysteine is in a region that changes conformation between the pre- and postfusion states. Although this method has been successful in the case of HIV-1 Env (SOSIP) and RSV F (DS-Cav1)[23,24], the disulfides introduced into S2 generally had detrimental effects. For example, inter-subunit disulfides (e.g. S659C/S698C) decreased the protein expression by 60%, and the Q965C/S1003C substitution led to partially mis-folded spikes (FIG. 2). Inter-protomer disulfides have been shown to improve the trimer integrity of HIV-1 Env and the stability of RSV F[25,26], but the interprotomeric T961C/S758C substitution ablated expression relative to S-2P. In contrast, it was not found that stabilizing the flexible loops located in the protomer interfaces was beneficial. Both S884C/A893C and T791C/A879C increased thermostability and expression, and resulted in native trimer structures. It is possible that anchoring flexible loops to a relatively rigid α-helix favors protomer assembly.

Introducing a salt bridge at the HIV-1 gp120-gp41 interface not only boosted the protein expression but also enhanced the binding of trimer-specific antibodies, suggesting improved retention of the native quaternary structure[22]. Based on a similar principle, the T961D substitution was introduced to form an electrostatic interaction with Arg765 from a neighboring protomer (FIG. 1). Likewise, the G769E substitution was intended to form an inter-protomeric salt bridge with Arg1014. Both variants increased the expression and also resembled well-folded trimeric spikes (FIG. 2). In addition to salt bridges, filling loosely packed hydrophobic cores that allows the protein to refold can help stabilize the prefusion state, as shown by previous cavity-filling substitutions in RSV F and HIV-1 Env[23,24,27]. Here, the L983F substitution was designed to fill a cavity formed in part by HR1, the FP and a β-hairpin. This variant had a 2-fold increase in expression (FIG. 2) and appeared to have additive effects when pairing with disulfide or proline substitutions.

Among the best single-substitution variants discovered were F817P and A942P, which both substantially improved the quality and quantity of the spikes (FIG. 2). By further combining them with A892P and A899P substitutions, the best construct to date was generated, HexaPro. These results are reminiscent of previous successful applications of proline substitutions to HIV-1 Env, RSV F, hMPV F, MERS-CoV S and Ebola GP[23,24,28-30]. In addition, the solvent accessibility of hydrophobic residues near the fusion peptide was a concern for influenza HA stem-only designs[31], and similarly this issue was addressed here by replacing the exposed Phe817 with Pro (FIG. 5C). The A942P substitution imposes rigidity to the flexible loop between the connector region and HRX, and is similar to that of the T577P substitution found to be helpful for stabilizing Ebola GP[28].

In the HexaPro cryo-EM dataset it was observed that a third of the particles in a two-RBD-up conformation, which had not been previously observed for SARS-CoV-2 spikes until a recent structure was determined of a modified spike containing four hydrophobic substitutions that brought SD1 closer to S2 and thus rendered RBD in up position[32]. It is hypothesized that the more stable S2 in HexaPro allowed us to capture this relatively unstable conformation that may transiently exist prior to triggering and dissociation of 51. This is similar to what was observed in the structures of the stable MERS-CoV S-2P spikes, where even the 3-RBD-up conformation could be observed[30]. HexaPro spikes were also able to retain the prefusion state after freeze-thaws, room temperature storage, and heat stress, which should enable the development of HexaPro spikes as subunit vaccine antigens. Furthermore, industrial production of recombinant proteins is often carried out by large scale expression in CHO cells. 32.5 mg of well-folded HexaPro was obtained from 1 L of Expi-CHO cells, providing feasibility for industrial production. HexaPro spikes could also improve DNA or mRNA-based vaccines by producing more antigen per nucleic acid molecule, thus improving efficacy at the same dose or maintaining efficacy at lower doses.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Peiris, J. S. M. et al. Coronavirus as a possible cause of severe acute respiratory syndrome. *Lancet* 361, 1319-1325 (2003).
2. Zaki, A. M., Van Boheemen, S., Bestebroer, T. M., Osterhaus, A. D. M. E. & Fouchier, R. A. M. Isolation of a novel coronavirus from a man with pneumonia in Saudi Arabia. *N. Engl. J. Med.* 367, 1814-1820 (2012).
3. Chan, J. F. W. et al. A familial cluster of pneumonia associated with the 2019 novel coronavirus indicating person-to-person transmission: a study of a family cluster. *Lancet* 395, 514-523 (2020).
4. Huang, C. et al. Clinical features of patients infected with 2019 novel coronavirus in Wuhan, China. *Lancet* 395, 497-506 (2020).
5. Li, F. Structure, Function, and Evolution of Coronavirus Spike Proteins. *Annu. Rev. Virol.* 3, 237-261 (2016).
6. Siebert, D. N., Bosch, B. J., van der Zee, R., de Haan, C. A. M. & Rottier, P. J. M. The Coronavirus Spike Protein Is a Class I Virus Fusion Protein: Structural and Functional Characterization of the Fusion Core Complex. *J. Virol.* 77, 8801-8811 (2003).
7. Mille, J. K. & Whittaker, G. R. Host cell entry of Middle East respiratory syndrome coronavirus after two-step, furin-mediated activation of the spike protein. *Proc. Natl. Acad. Sci. U.S.A.* 111, 15214-15219 (2014).
8. Hoffmann, M. et al. SARS-CoV-2 Cell Entry Depends on ACE2 and TMPRSS2 and Is Blocked by a Clinically Proven Protease Inhibitor. *Cell* 181, 271-280.e8 (2020).
9. Wan, Y., Shang, J., Graham, R., Baric, R. S. & Li, F. Receptor Recognition by the Novel Coronavirus from Wuhan: an Analysis Based on Decade-Long Structural Studies of SARS Coronavirus. *J. Virol.* 94, 1-9 (2020).
10. Zhou, P. et al. A pneumonia outbreak associated with a new coronavirus of probable bat origin. *Nature* 579, 270-273 (2020).

11. Walls, A. C. et al. Tectonic conformational changes of a coronavirus spike glycoprotein promote membrane fusion. *Proc. Natl. Acad. Sci. U.S.A.* 114, 11157-11162 (2017).

12. Wang, C. et al. A human monoclonal antibody blocking SARS-CoV-2 infection. *Nat. Commun.* 11, 1-6 (2020).

13. Buchholz, U. J. et al. Contributions of the structural proteins of severe respiratory syndrome coronavirus to protective immunity. *Proc. Natl. Acad. Sci. U.S.A.* 101, 9804-9809 (2004).

14. Hofmann, H. et al. S Protein of Severe Acute Respiratory Syndrome-Associated Coronavirus Mediates Entry into Hepatoma Cell Lines and Is Targeted by Neutralizing Antibodies in Infected Patients. *J. Virol.* 78, 6134-6142 (2004).

15. McLellan, J. S. et al. Structure-based design of a fusion glycoprotein vaccine for respiratory syncytial virus. *Science* 342, 592-598 (2013).

16. Pallesen, J. et al. Immunogenicity and structures of a rationally designed prefusion MERS-CoV spike antigen. *Proc. Natl. Acad. Sci. U.S.A.* 114, E7348-E7357 (2017).

17. Park, Y. J. et al. Structures of MERS-CoV spike glycoprotein in complex with sialoside attachment receptors. *Nat. Struct. Mol. Biol.* 26, 1151-1157 (2019).

18. Li, Z. et al. The human coronavirus HCoV-229E S-protein structure and receptor binding. *Elife* 8, 1-22 (2019).

19. Wang, N. et al. Structural Definition of a Neutralization-Sensitive Epitope on the MERS-CoV S1-NTD. *Cell Rep.* 28, 3395-3405.e6 (2019).

20. Wrapp, D. et al. Cryo-EM structure of the 2019-nCoV spike in the prefusion conformation. *Science* (80-.). 367, 1260-1263 (2020).

21. Walls, A. C. et al. Structure, Function, and Antigenicity of the SARS-CoV-2 Spike Glycoprotein. *Cell* 181, 281-292.e6 (2020).

22. Rutten, L. et al. A Universal Approach to Optimize the Folding and Stability of Prefusion-Closed HIV-1 Envelope Trimers. *Cell Rep.* 23, 584-595 (2018).

23. Sanders, R. W. et al. A next-generation cleaved, soluble HIV-1 Env trimer, BG505 SOSIP.664 gp140, expresses multiple epitopes for broadly neutralizing but not non-neutralizing antibodies. *PLoS Pathog.* 9, e1003618 (2013).

24. Mclellan, J. S. et al. Structure-Based Design of a Fusion Glycoprotein Vaccine for Respiratory Syncytial Virus. *Science* (80-.). 342, 592-598 (2013).

25. Yang, L. et al. Structure-Guided Redesign Improves NFL HIV Env Trimer Integrity and Identifies an Inter-Protomer Disulfide Permitting Post-Expression Cleavage. *Front. Immunol.* 9, 1631 (2018).

26. Joyce, M. G. et al. Iterative structure-based improvement of a fusion-glycoprotein vaccine against RSV. *Nat. Struct. Mol. Biol.* 23, 811-820 (2016).

27. Krarup, A. et al. A highly stable prefusion RSV F vaccine derived from structural analysis of the fusion mechanism. *Nat. Commun.* 6, 8143 (2015).

28. Rutten, L. et al. Structure-Based Design of Prefusion-Stabilized Filovirus Glycoprotein Trimers. *Cell Rep.* 30, 4540-4550.e3 (2020).

29. Battles, M. B. et al. Structure and immunogenicity of pre-fusion-stabilized human metapneumovirus F glycoprotein. *Nat. Commun.* 8, 1528 (2017).

30. Pallesen, J. et al. Immunogenicity and structures of a rationally designed prefusion MERS-CoV spike antigen. *Proc. Natl. Acad. Sci. U.S.A.* 114, E7348-E7357 (2017).

31. Impagliazzo, A. et al. A stable trimeric influenza hemagglutinin stem as a broadly protective immunogen. *Science* 349, 1301-1306 (2015).

32. Henderson, R. et al. Controlling the SARS-CoV-2 Spike Glycoprotein Conformation. *bioRxiv* 2020.05.18.102087 (2020). doi:10.1101/2020.05.18.102087

33. Tegunov, D. & Cramer, P. Real-time cryo-electron microscopy data preprocessing with Warp. *Nat. Methods* 16, 1146-1152 (2019).

34. Punjani, A., Rubinstein, J. L., Fleet, D. J. & Brubaker, M. A. CryoSPARC: Algorithms for rapid unsupervised cryo-EM structure determination. *Nat. Methods* 14, 290-296 (2017).

35. Emsley, P., Lohkamp, B., Scott, W. G. & Cowtan, K. Features and development of Coot. *Acta Crystallogr. D. Biol. Crystallogr.* 66, 486-501 (2010).

36. Liebschner, D. et al. Macromolecular structure determination using X-rays, neutrons and electrons: Recent developments in Phenix. *Acta Crystallogr. Sect. D Struct. Biol.* 75, 861-877 (2019).

37. Croll, T. I. ISOLDE: a physically realistic environment for model building into low-resolution electron-density maps. *Acta Crystallogr. Sect. D, Struct. Biol.* 74, 519-530 (2018).

What is claimed is:

1. An engineered protein, comprising an engineered coronavirus S protein ectodomain having at least 90% identity to: (a) positions 14-1208 of SEQ ID NO: 1 or 2; (b) positions 14-1160 of SEQ ID NO: 1 or 2; or (c) positions 319-1208 of SEQ ID NO: 1 or 2, said engineered protein comprising at least one mutation relative to the sequence of SEQ ID NO: 1 or 2, said at least one mutation comprising:

(i) a substitution at a position corresponding to: T724, T752, T778, T961, I1013, H1058, S735, T859, I770, A1015, L727, S1021, Q901, S875, T912, H1088, L1141, V1040, L966, A766, T778, L938, V963, V911, N1108, V705, A893, N703, A672, A694, A1080, I1132, P862, T859, T547, N978, T961, S758, Q762, D1118, S659, S698, R1039, V722, A930, A903, Q913, S974, D979, P728, V951, V736, L858, S884, P807, S875, T791, A879, G799, A924, V826, A899, Q779, F817, L865, T866, A892, T912, A570, V963, T874, S1055, V729, A1022, L894, A713, L828, L822, A1056, Q965, S1003, A972, Q992, I980, A1078, V1133, T1120, I870, S1055, T1117, D1139, T1116, Y1138, I896, G885, Q901, F1103, P1112, G889, L1034, E819, S1055, I1081, N1135, Q1054, Q957, I1130, V1104, R1000, A944, T724, S730, G769, Q895, K921, L922, N978, A942, G946, S975, A890, or S1003; and/or (ii) a deletion corresponding to positions 829-851, 675-686, 673-684, 1161-1208, or 1142-1208; and/or (iii) a substitution of two amino acids for amino acid positions 673-686.

2. The engineered protein of claim 1, comprising an engineered disulfide bond comprising paired cysteine substitutions at positions corresponding to: S735C and T859C; I770C and A1015C; L727C and S1021C; V911C and N1108C; A672C and A694C; A1080C and I1132C; S659C and S698C; V722C and A930C; A903C and Q913C; S974C and D979C; P728C and V951C; V736C and L858C; S884C and A893C; P807C and S875C; T791C and A879C; G799C and A924C; A570C and V963C; T874C and S1055C; V729C and A1022C; L822C and A1056C; Q965C and S1003C; A972C and Q992C; I980C and Q992C; A1078C and V1133C; H1088C and T1120C; I870C and S1055C; T1117C and D1139C; T1116C and Y1138C; I896C and Q901C; G885C and Q901C; F1103C and P1112C; G889C and L1034C; E819C and S1055C; A972C and I980C; I1081C and N1135C; or E819C and Q1054C.

3. The engineered protein of claim 1, comprising a cavity filling substitution selected from: T724M, I1013F, H1058W, Q901M, S875F, H1088W, L1141F, V1040F, T778L, L938F,

US 12,617,820 B2

101

V963L, R1039F, V826L, A899F, Q779M, L894F, H1058F, H1058Y, V1040Y, H1088Y, V1104I, R1000Y, R1000W, A944F, T724I, A944Y, S730L, A890V, D1118F, or S1003V.

4. The engineered protein of claim 1, comprising a proline substitution selected from: F817P, L865P, T866P, A892P, A899P, T912P, A893P, Q895P, K921P, L922P, N978P, A942P, G946P, or S975P.

5. The engineered protein of claim 1, comprising proline substitutions at A892P; A942P; A899P; and F817P.

6. The engineered protein of claim 1, comprising an electrostatic interaction substitution selected from: T752K, T912R, L828K, L828R, S730R, T961D, A766E, P862E, T859K, Q957E, G769E, T778Q, A713S, or I1130Y.

7. The engineered protein of claim 1, further comprising K986P and V987P substitutions.

8. The engineered protein of claim 1, comprising a combination of at least one engineered disulfide bond, at least one cavity filling substitution, at least one proline substitution, and at least one electrostatic interaction substitution.

9. The engineered protein of claim 1, wherein the engineered coronavirus S protein ectodomain comprises a mutation that eliminates the furin cleavage site.

10. The engineered protein of claim 1, wherein the protein is fused or conjugated to a trimerization domain.

11. The engineered protein of claim 10, wherein the trimerization domain comprises a T4 fibritin trimerization domain.

12. The engineered protein of claim 1, wherein the protein is fused or conjugated to a transmembrane domain.

13. The engineered protein of claim 12, wherein the transmembrane domain comprises a SARS-COV-2 transmembrane domain.

14. An engineered coronavirus trimer comprising at least one subunit comprising the engineered protein according to claim 1.

15. The engineered trimer of claim 14, wherein the trimer comprises at least one engineered disulfide bond between subunits, wherein the at least one engineered disulfide bond between subunits is selected from: V705C and A893C; T547C and N978C; T961C and S758C; and/or T961C and Q762C.

16. A pharmaceutical composition comprising a pharmaceutically acceptable carrier; and an engineered protein of claim 1.

17. A nucleic acid molecule comprising a nucleotide sequence that encodes an amino acid sequence of an engineered protein of claim 1.

18. A method of preventing coronavirus infection in a subject, comprising administering to the subject an effective amount of the pharmaceutical composition according to claim 16.

19. A composition comprising an engineered protein of claim 1 bound to an antibody.

20. The engineered protein of claim 1, further comprising proline substitutions at F817P; A892P; A899P; A942P; K986P; and V987P.

* * * * *

SEQUENCE LISTING

```
<160> NUMBER OF SEQ ID NOS: 80

<210> SEQ ID NO 1
<211> LENGTH: 1288
<212> TYPE: PRT
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (1)..(1208)
<223> OTHER INFORMATION: SARS-CoV-2 Ectodomain
<220> FEATURE:
<221> NAME/KEY: MISC_FEATURE
<222> LOCATION: (1209)..(1288)
<223> OTHER INFORMATION: Trimerization domain and tags

<400> SEQUENCE: 1
```

-continued

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415
```

-continued

```
Lys Ile Ala Asp Tyr Asn Tyr Lys Leu Pro Asp Asp Phe Thr Gly Cys
            420               425               430

Val Ile Ala Trp Asn Ser Asn Asn Leu Asp Ser Lys Val Gly Gly Asn
            435               440               445

Tyr Asn Tyr Leu Tyr Arg Leu Phe Arg Lys Ser Asn Leu Lys Pro Phe
    450               455               460

Glu Arg Asp Ile Ser Thr Glu Ile Tyr Gln Ala Gly Ser Thr Pro Cys
465               470               475               480

Asn Gly Val Glu Gly Phe Asn Cys Tyr Phe Pro Leu Gln Ser Tyr Gly
                485               490               495

Phe Gln Pro Thr Asn Gly Val Gly Tyr Gln Pro Tyr Arg Val Val Val
            500               505               510

Leu Ser Phe Glu Leu Leu His Ala Pro Ala Thr Val Cys Gly Pro Lys
            515               520               525

Lys Ser Thr Asn Leu Val Lys Asn Lys Cys Val Asn Phe Asn Phe Asn
    530               535               540

Gly Leu Thr Gly Thr Gly Val Leu Thr Glu Ser Asn Lys Lys Phe Leu
545               550               555               560

Pro Phe Gln Gln Phe Gly Arg Asp Ile Ala Asp Thr Thr Asp Ala Val
            565               570               575

Arg Asp Pro Gln Thr Leu Glu Ile Leu Asp Ile Thr Pro Cys Ser Phe
            580               585               590

Gly Gly Val Ser Val Ile Thr Pro Gly Thr Asn Thr Ser Asn Gln Val
            595               600               605

Ala Val Leu Tyr Gln Asp Val Asn Cys Thr Glu Val Pro Val Ala Ile
    610               615               620

His Ala Asp Gln Leu Thr Pro Thr Trp Arg Val Tyr Ser Thr Gly Ser
625               630               635               640

Asn Val Phe Gln Thr Arg Ala Gly Cys Leu Ile Gly Ala Glu His Val
            645               650               655

Asn Asn Ser Tyr Glu Cys Asp Ile Pro Ile Gly Ala Gly Ile Cys Ala
            660               665               670

Ser Tyr Gln Thr Gln Thr Asn Ser Pro Arg Arg Ala Arg Ser Val Ala
    675               680               685

Ser Gln Ser Ile Ile Ala Tyr Thr Met Ser Leu Gly Ala Glu Asn Ser
    690               695               700

Val Ala Tyr Ser Asn Asn Ser Ile Ala Ile Pro Thr Asn Phe Thr Ile
705               710               715               720

Ser Val Thr Thr Glu Ile Leu Pro Val Ser Met Thr Lys Thr Ser Val
            725               730               735

Asp Cys Thr Met Tyr Ile Cys Gly Asp Ser Thr Glu Cys Ser Asn Leu
            740               745               750

Leu Leu Gln Tyr Gly Ser Phe Cys Thr Gln Leu Asn Arg Ala Leu Thr
            755               760               765

Gly Ile Ala Val Glu Gln Asp Lys Asn Thr Gln Glu Val Phe Ala Gln
    770               775               780

Val Lys Gln Ile Tyr Lys Thr Pro Pro Ile Lys Asp Phe Gly Gly Phe
785               790               795               800

Asn Phe Ser Gln Ile Leu Pro Asp Pro Ser Lys Pro Ser Lys Arg Ser
                805               810               815

Phe Ile Glu Asp Leu Leu Phe Asn Lys Val Thr Leu Ala Asp Ala Gly
            820               825               830

Phe Ile Lys Gln Tyr Gly Asp Cys Leu Gly Asp Ile Ala Ala Arg Asp
```

-continued

```
          835              840              845

Leu Ile Cys Ala Gln Lys Phe Asn Gly Leu Thr Val Leu Pro Pro Leu
    850              855              860

Leu Thr Asp Glu Met Ile Ala Gln Tyr Thr Ser Ala Leu Leu Ala Gly
865              870              875              880

Thr Ile Thr Ser Gly Trp Thr Phe Gly Ala Gly Ala Ala Leu Gln Ile
                 885              890              895

Pro Phe Ala Met Gln Met Ala Tyr Arg Phe Asn Gly Ile Gly Val Thr
                 900              905              910

Gln Asn Val Leu Tyr Glu Asn Gln Lys Leu Ile Ala Asn Gln Phe Asn
                 915              920              925

Ser Ala Ile Gly Lys Ile Gln Asp Ser Leu Ser Ser Thr Ala Ser Ala
    930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
                 965              970              975

Leu Asn Asp Ile Leu Ser Arg Leu Asp Lys Val Glu Ala Glu Val Gln
                 980              985              990

Ile Asp Arg Leu Ile Thr Gly Arg  Leu Gln Ser Leu Gln  Thr Tyr Val
                 995              1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080

Asp Gly  Lys Ala His Phe Pro  Arg Glu Gly Val Phe  Val Ser Asn
    1085             1090             1095

Gly Thr  His Trp Phe Val Thr  Gln Arg Asn Phe Tyr  Glu Pro Gln
    1100             1105             1110

Ile Ile  Thr Thr Asp Asn Thr  Phe Val Ser Gly Asn  Cys Asp Val
    1115             1120             1125

Val Ile  Gly Ile Val Asn Asn  Thr Val Tyr Asp Pro  Leu Gln Pro
    1130             1135             1140

Glu Leu  Asp Ser Phe Lys Glu  Glu Leu Asp Lys Tyr  Phe Lys Asn
    1145             1150             1155

His Thr  Ser Pro Asp Val Asp  Leu Gly Asp Ile Ser  Gly Ile Asn
    1160             1165             1170

Ala Ser  Val Val Asn Ile Gln  Lys Glu Ile Asp Arg  Leu Asn Glu
    1175             1180             1185

Val Ala  Lys Asn Leu Asn Glu  Ser Leu Ile Asp Leu  Gln Glu Leu
    1190             1195             1200

Gly Lys  Tyr Glu Gln Gly Ser  Gly Tyr Ile Pro Glu  Ala Pro Arg
    1205             1210             1215

Asp Gly  Gln Ala Tyr Val Arg  Lys Asp Gly Glu Trp  Val Leu Leu
    1220             1225             1230

Ser Thr  Phe Leu Gly Arg Ser  Leu Glu Val Leu Phe  Gln Gly Pro
    1235             1240             1245
```

-continued

```
Gly His  His His His His His  His His Ser Ala Trp  Ser His Pro
    1250              1255              1260

Gln Phe  Glu Lys Gly Gly Gly  Ser Gly Gly Gly Gly  Ser Gly Gly
    1265              1270              1275

Ser Ala  Trp Ser His Pro Gln  Phe Glu Lys
    1280              1285

<210> SEQ ID NO 2
<211> LENGTH: 1208
<212> TYPE: PRT
<213> ORGANISM: Artificial Sequence
<220> FEATURE:
<223> OTHER INFORMATION: Synthetic oligonucleotide
<220> FEATURE:
<221> NAME/KEY: MISC_FEATURE
<222> LOCATION: (5)..(5)
<223> OTHER INFORMATION: Xaa is Leu or Phe
<220> FEATURE:
<221> NAME/KEY: MISC_FEATURE
<222> LOCATION: (13)..(13)
<223> OTHER INFORMATION: Xaa is Ser or Ile
<220> FEATURE:
<221> NAME/KEY: MISC_FEATURE
<222> LOCATION: (18)..(18)
<223> OTHER INFORMATION: Xaa is Leu or Phe
<220> FEATURE:
<221> NAME/KEY: MISC_FEATURE
<222> LOCATION: (19)..(19)
<223> OTHER INFORMATION: Xaa is Thr or Arg
<220> FEATURE:
<221> NAME/KEY: MISC_FEATURE
<222> LOCATION: (20)..(20)
<223> OTHER INFORMATION: Xaa is Thr or Asn
<220> FEATURE:
<221> NAME/KEY: MISC_FEATURE
<222> LOCATION: (26)..(26)
<223> OTHER INFORMATION: Xaa is Pro or Ser
<220> FEATURE:
<221> NAME/KEY: MISC_FEATURE
<222> LOCATION: (67)..(67)
<223> OTHER INFORMATION: Xaa is Ala or Val
<220> FEATURE:
<221> NAME/KEY: MISC_FEATURE
<222> LOCATION: (69)..(69)
<223> OTHER INFORMATION: Xaa is His or absent
<220> FEATURE:
<221> NAME/KEY: MISC_FEATURE
<222> LOCATION: (70)..(70)
<223> OTHER INFORMATION: Xaa is Val or absent
<220> FEATURE:
<221> NAME/KEY: MISC_FEATURE
<222> LOCATION: (80)..(80)
<223> OTHER INFORMATION: Xaa is Asp, Gly, or Ala
<220> FEATURE:
<221> NAME/KEY: MISC_FEATURE
<222> LOCATION: (95)..(95)
<223> OTHER INFORMATION: Xaa is Thr or Ile
<220> FEATURE:
<221> NAME/KEY: MISC_FEATURE
<222> LOCATION: (138)..(138)
<223> OTHER INFORMATION: Xaa is Asp or Tyr
<220> FEATURE:
<221> NAME/KEY: MISC_FEATURE
<222> LOCATION: (142)..(142)
<223> OTHER INFORMATION: Xaa is Gly or Asp
<220> FEATURE:
<221> NAME/KEY: MISC_FEATURE
<222> LOCATION: (144)..(144)
<223> OTHER INFORMATION: Xaa is Tyr or absent
<220> FEATURE:
<221> NAME/KEY: MISC_FEATURE
<222> LOCATION: (152)..(152)
<223> OTHER INFORMATION: Xaa is Trp or Cys
<220> FEATURE:
<221> NAME/KEY: MISC_FEATURE
```

-continued

```
<222> LOCATION: (154)..(154)
<223> OTHER INFORMATION: Xaa is Glu or Lys
<220> FEATURE:
<221> NAME/KEY: MISC_FEATURE
<222> LOCATION: (156)..(156)
<223> OTHER INFORMATION: Xaa is Glu or absent
<220> FEATURE:
<221> NAME/KEY: MISC_FEATURE
<222> LOCATION: (157)..(157)
<223> OTHER INFORMATION: Xaa is Phe, Ser, or absent
<220> FEATURE:
<221> NAME/KEY: MISC_FEATURE
<222> LOCATION: (158)..(158)
<223> OTHER INFORMATION: Xaa is Arg or Gly
<220> FEATURE:
<221> NAME/KEY: MISC_FEATURE
<222> LOCATION: (190)..(190)
<223> OTHER INFORMATION: Xaa is Arg or Ser
<220> FEATURE:
<221> NAME/KEY: MISC_FEATURE
<222> LOCATION: (215)..(215)
<223> OTHER INFORMATION: Xaa is Asp or Gly
<220> FEATURE:
<221> NAME/KEY: MISC_FEATURE
<222> LOCATION: (241)..(241)
<223> OTHER INFORMATION: Xaa is Leu or absent
<220> FEATURE:
<221> NAME/KEY: MISC_FEATURE
<222> LOCATION: (242)..(242)
<223> OTHER INFORMATION: Xaa is Leu or absent
<220> FEATURE:
<221> NAME/KEY: MISC_FEATURE
<222> LOCATION: (243)..(243)
<223> OTHER INFORMATION: Xaa is Ala or absent
<220> FEATURE:
<221> NAME/KEY: MISC_FEATURE
<222> LOCATION: (253)..(253)
<223> OTHER INFORMATION: Xaa is Asp or Gly
<220> FEATURE:
<221> NAME/KEY: MISC_FEATURE
<222> LOCATION: (417)..(417)
<223> OTHER INFORMATION: Xaa is Lys, Asn, or Thr
<220> FEATURE:
<221> NAME/KEY: MISC_FEATURE
<222> LOCATION: (452)..(452)
<223> OTHER INFORMATION: Xaa is Leu or Arg
<220> FEATURE:
<221> NAME/KEY: MISC_FEATURE
<222> LOCATION: (477)..(477)
<223> OTHER INFORMATION: Xaa is Ser or Asn
<220> FEATURE:
<221> NAME/KEY: MISC_FEATURE
<222> LOCATION: (478)..(478)
<223> OTHER INFORMATION: Xaa is Thr or Lys
<220> FEATURE:
<221> NAME/KEY: MISC_FEATURE
<222> LOCATION: (484)..(484)
<223> OTHER INFORMATION: Xaa is Glu, Lys, or Gln
<220> FEATURE:
<221> NAME/KEY: MISC_FEATURE
<222> LOCATION: (494)..(494)
<223> OTHER INFORMATION: Xaa is Ser or Pro
<220> FEATURE:
<221> NAME/KEY: MISC_FEATURE
<222> LOCATION: (501)..(501)
<223> OTHER INFORMATION: Xaa is Asn or Tyr
<220> FEATURE:
<221> NAME/KEY: MISC_FEATURE
<222> LOCATION: (565)..(565)
<223> OTHER INFORMATION: Xaa is Phe or Leu
<220> FEATURE:
<221> NAME/KEY: MISC_FEATURE
<222> LOCATION: (570)..(570)
<223> OTHER INFORMATION: Xaa is Ala or Asp
<220> FEATURE:
<221> NAME/KEY: MISC_FEATURE
<222> LOCATION: (614)..(614)
<223> OTHER INFORMATION: Xaa is Asp or Gly
<220> FEATURE:
```

```
<221> NAME/KEY: MISC_FEATURE
<222> LOCATION: (655)..(655)
<223> OTHER INFORMATION: Xaa is His or Tyr
<220> FEATURE:
<221> NAME/KEY: MISC_FEATURE
<222> LOCATION: (677)..(677)
<223> OTHER INFORMATION: Xaa is Gln or His
<220> FEATURE:
<221> NAME/KEY: MISC_FEATURE
<222> LOCATION: (681)..(681)
<223> OTHER INFORMATION: Xaa is Pro, His, or Arg
<220> FEATURE:
<221> NAME/KEY: MISC_FEATURE
<222> LOCATION: (701)..(701)
<223> OTHER INFORMATION: Xaa is Ala or Val
<220> FEATURE:
<221> NAME/KEY: MISC_FEATURE
<222> LOCATION: (716)..(716)
<223> OTHER INFORMATION: Xaa is Thr or Ile
<220> FEATURE:
<221> NAME/KEY: MISC_FEATURE
<222> LOCATION: (791)..(791)
<223> OTHER INFORMATION: Xaa is Thr or Ile
<220> FEATURE:
<221> NAME/KEY: MISC_FEATURE
<222> LOCATION: (859)..(859)
<223> OTHER INFORMATION: Xaa is Thr or Asn
<220> FEATURE:
<221> NAME/KEY: MISC_FEATURE
<222> LOCATION: (888)..(888)
<223> OTHER INFORMATION: Xaa is Phe or Leu
<220> FEATURE:
<221> NAME/KEY: MISC_FEATURE
<222> LOCATION: (950)..(950)
<223> OTHER INFORMATION: Xaa is Asp, His, or Asn
<220> FEATURE:
<221> NAME/KEY: MISC_FEATURE
<222> LOCATION: (982)..(982)
<223> OTHER INFORMATION: Xaa is Ser or Ala
<220> FEATURE:
<221> NAME/KEY: MISC_FEATURE
<222> LOCATION: (1027)..(1027)
<223> OTHER INFORMATION: Xaa is Thr or Ile
<220> FEATURE:
<221> NAME/KEY: MISC_FEATURE
<222> LOCATION: (1071)..(1071)
<223> OTHER INFORMATION: Xaa is Gln or His
<220> FEATURE:
<221> NAME/KEY: MISC_FEATURE
<222> LOCATION: (1118)..(1118)
<223> OTHER INFORMATION: Xaa is Asp or His
<220> FEATURE:
<221> NAME/KEY: MISC_FEATURE
<222> LOCATION: (1176)..(1176)
<223> OTHER INFORMATION: Xaa is Val or Phe
<220> FEATURE:
<221> NAME/KEY: MISC_FEATURE
<222> LOCATION: (1191)..(1191)
<223> OTHER INFORMATION: Xaa is Lys or Asn

<400> SEQUENCE: 2

Met Phe Val Phe Xaa Val Leu Leu Pro Leu Val Ser Xaa Gln Cys Val
1               5                   10                  15

Asn Xaa Xaa Xaa Arg Thr Gln Leu Pro Xaa Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Xaa Ile Xaa Xaa Ser Gly Thr Asn Gly Thr Lys Arg Phe Xaa
65                  70                  75                  80

Asn Pro Val Leu Pro Phe Asn Asp Gly Val Tyr Phe Ala Ser Xaa Glu
            85                  90                  95
```

```
Lys Ser Asn Ile Ile Arg Gly Trp Ile Phe Gly Thr Thr Leu Asp Ser
        100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Xaa Pro Phe Leu Xaa Val Xaa
        130                 135                 140

Tyr His Lys Asn Asn Lys Ser Xaa Met Xaa Ser Xaa Xaa Xaa Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Xaa Glu Phe
        180                 185                 190

Val Phe Lys Asn Ile Asp Gly Tyr Phe Lys Ile Tyr Ser Lys His Thr
        195                 200                 205

Pro Ile Asn Leu Val Arg Xaa Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Xaa Xaa Xaa Leu His Arg Ser Tyr Leu Thr Pro Gly Xaa Ser Ser Ser
                245                 250                 255

Gly Trp Thr Ala Gly Ala Ala Ala Tyr Tyr Val Gly Tyr Leu Gln Pro
        260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
        340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Xaa Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
        435                 440                 445

Tyr Asn Tyr Xaa Tyr Arg Leu Phe Arg Lys Ser Asn Leu Lys Pro Phe
        450                 455                 460

Glu Arg Asp Ile Ser Thr Glu Ile Tyr Gln Ala Gly Xaa Xaa Pro Cys
465                 470                 475                 480

Asn Gly Val Xaa Gly Phe Asn Cys Tyr Phe Pro Leu Gln Xaa Tyr Gly
                485                 490                 495

Phe Gln Pro Thr Xaa Gly Val Gly Tyr Gln Pro Tyr Arg Val Val Val
        500                 505                 510
```

-continued

```
Leu Ser Phe Glu Leu Leu His Ala Pro Ala Thr Val Cys Gly Pro Lys
    515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Xaa Gly Arg Asp Ile Xaa Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Xaa Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu Xaa Val
                645                 650                 655

Asn Asn Ser Tyr Glu Cys Asp Ile Pro Ile Gly Ala Gly Ile Cys Ala
            660                 665                 670

Ser Tyr Gln Thr Xaa Thr Asn Ser Xaa Arg Arg Ala Arg Ser Val Ala
            675                 680                 685

Ser Gln Ser Ile Ile Ala Tyr Thr Met Ser Leu Gly Xaa Glu Asn Ser
    690                 695                 700

Val Ala Tyr Ser Asn Asn Ser Ile Ala Ile Pro Xaa Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
    770                 775                 780

Val Lys Gln Ile Tyr Lys Xaa Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Xaa Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Xaa Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
```

```
            930              935              940
Leu Gly Lys Leu Gln Xaa Val Val Asn Gln Asn Ala Gln Ala Leu Asn
945                 950              955              960

Thr Leu Val Lys Gln Leu Ser Ser Asn Phe Gly Ala Ile Ser Ser Val
                965              970              975

Leu Asn Asp Ile Leu Xaa Arg Leu Asp Lys Val Glu Ala Glu Val Gln
                980              985              990

Ile Asp Arg Leu Ile Thr Gly Arg  Leu Gln Ser Leu Gln  Thr Tyr Val
        995          1000               1005

Thr Gln  Gln Leu Ile Arg Ala  Ala Glu Ile Arg Ala  Ser Ala Asn
    1010             1015              1020

Leu Ala  Ala Xaa Lys Met Ser  Glu Cys Val Leu Gly  Gln Ser Lys
    1025             1030              1035

Arg Val  Asp Phe Cys Gly Lys  Gly Tyr His Leu Met  Ser Phe Pro
    1040             1045              1050

Gln Ser  Ala Pro His Gly Val  Val Phe Leu His Val  Thr Tyr Val
    1055             1060              1065

Pro Ala  Xaa Glu Lys Asn Phe  Thr Thr Ala Pro Ala  Ile Cys His
    1070             1075              1080

Asp Gly  Lys Ala His Phe Pro  Arg Glu Gly Val Phe  Val Ser Asn
    1085             1090              1095

Gly Thr  His Trp Phe Val Thr  Gln Arg Asn Phe Tyr  Glu Pro Gln
    1100             1105              1110

Ile Ile  Thr Thr Xaa Asn Thr  Phe Val Ser Gly Asn  Cys Asp Val
    1115             1120              1125

Val Ile  Gly Ile Val Asn Asn  Thr Val Tyr Asp Pro  Leu Gln Pro
    1130             1135              1140

Glu Leu  Asp Ser Phe Lys Glu  Glu Leu Asp Lys Tyr  Phe Lys Asn
    1145             1150              1155

His Thr  Ser Pro Asp Val Asp  Leu Gly Asp Ile Ser  Gly Ile Asn
    1160             1165              1170

Ala Ser  Xaa Val Asn Ile Gln  Lys Glu Ile Asp Arg  Leu Asn Glu
    1175             1180              1185

Val Ala  Xaa Asn Leu Asn Glu  Ser Leu Ile Asp Leu  Gln Glu Leu
    1190             1195              1200

Gly Lys  Tyr Glu Gln
    1205
```

<210> SEQ ID NO 3
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 3 ggtaccaga                                                        9

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
ccgtctcagg ccgagttcgg tacc                                       24

-continued

```
<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 5
ggaaacaagg caacttcaag aacctgagag aattc                               35

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 6
gccgtcgatg ttcttgaaca cgaattc                                        27

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
gggtctgctt cctctgtagc tagc                                           24

<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 8
ggtgtaggcg atgatgctct ggctagc                                        27

<210> SEQ ID NO 9
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 9
cagctctgtg ctgaacgata tcctgtctag a                                   31

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
ggcttctgga gggtccagtc taga                                           24

<210> SEQ ID NO 11
<211> LENGTH: 23
<212> TYPE: DNA
<213> ORGANISM: Artificial Sequence
<220> FEATURE:
```

<223> OTHER INFORMATION: Synthetic oligonucleotide

<400> SEQUENCE: 11
ggcctcgggg atgtatccgg atc                                                       23

<210> SEQ ID NO 12
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 12
gggcaggatc tctgttgtgc agctaattgt aaag                                           34

<210> SEQ ID NO 13
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 13
ctttacaatt agctgcacaa cagagatcct gccc                                           34

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 14
ggatcttgcc gatgcaagaa ttgaactgg                                                 29

<210> SEQ ID NO 15
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 15
ccagttcaat tcttgcatcg gcaagatcc                                                 29

<210> SEQ ID NO 16
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 16
gccatgcaga tgtgctatag attcaacgga atcggcgtga cctgcaacgt gctgtatg               58

<210> SEQ ID NO 17
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 17
catacagcac gttgcaggtc acgccgattc cgttgaatct atagcacatc tgcatggc               58

-continued

```
<210> SEQ ID NO 18
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 18
cttctggagg gtccagtcta gacaggatac agttcagcac agagcagatg gcgccaaaat      60

<210> SEQ ID NO 19
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 19
cagagatcct gtgcgtgagc atgacc                                          26

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 20
ggtcatgctc acgcacagga tctctg                                          26

<210> SEQ ID NO 21
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 21
caaactgcag gactgcgtga atcagaacgc                                      30

<210> SEQ ID NO 22
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 22
gcgttctgat tcacgcagtc ctgcagtttg                                      30

<210> SEQ ID NO 23
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 23
gaccaagacc agctgtgact gtacaatgt                                       29

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide
```

-continued

```
<400> SEQUENCE: 24
acattgtaca gtcacagctg gtcttggtc                                29

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
ttcaacggct gcacagttct cccac                                    25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
gtgggagaac tgtgcagccg ttgaa                                    25

<210> SEQ ID NO 27
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 27
tcacatgtgg gtggacattt ggcgccggcg cctgcctgca                    40

<210> SEQ ID NO 28
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 28
tgcaggcagg cgccggcgcc aaatgtccac ccacatgtga                    40

<210> SEQ ID NO 29
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 29
aggcttagaa ggatcacaga gaatctggct                               30

<210> SEQ ID NO 30
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 30
agccagattc tctgtgatcc ttctaagcct                               30

<210> SEQ ID NO 31
<211> LENGTH: 25
```

```
<212> TYPE: DNA
<213> ORGANISM: Artificial Sequence
<220> FEATURE:
<223> OTHER INFORMATION: Synthetic oligonucleotide

<400> SEQUENCE: 31
tcagtacacc tgtgccctgc tggct                                        25

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 32
agccagcagg gcacaggtgt actga                                        25

<210> SEQ ID NO 33
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 33
aagcagatct acaagtgccc acctatcaag                                   30

<210> SEQ ID NO 34
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 34
cttgataggt gggcacttgt agatctgctt                                   30

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
tctgccctgc tgtgtggcac catca                                        25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
tgatggtgcc acacagcagg gcaga                                        25

<210> SEQ ID NO 37
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 37
```

-continued

```
ctggctaaag ttaaagcagc cgaagtcctt                                    30

<210> SEQ ID NO 38
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 38
aaggacttcg gctgctttaa ctttagccag                                    30

<210> SEQ ID NO 39
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 39
aaccagaagc tgatctgtaa ccagttcaat tct                                33

<210> SEQ ID NO 40
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 40
agaattgaac tggttacaga tcagcttctg gtt                                33

<210> SEQ ID NO 41
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 41
cggccagggt gagcttgttg aac                                           23

<210> SEQ ID NO 42
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 42
gttcaacaag ctcaccctgg ccg                                           23

<210> SEQ ID NO 43
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 43
aggccatctg catgaaaaag gggatctg                                      28

<210> SEQ ID NO 44
<211> LENGTH: 28
<212> TYPE: DNA
<213> ORGANISM: Artificial Sequence
```

-continued

```
<220> FEATURE:
<223> OTHER INFORMATION: Synthetic oligonucleotide

<400> SEQUENCE: 44
cagatcccct ttttcatgca gatggcct                                        28

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
gatcctcgat agggctccgc ttgc                                            24

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
gcaagcggag ccctatcgag gatc                                            24

<210> SEQ ID NO 47
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 47
gacaaaaata ccatggaggt gttcgccc                                        28

<210> SEQ ID NO 48
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 48
gggcgaacac ctccatggta tttttgtc                                        28

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
tcgtcggtcg gcagaggtgg                                                 20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
ccacctctgc cgaccgacga                                                 20
```

-continued

<210> SEQ ID NO 51
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 51
gccgcagaag tcaacgaatt tagactgtcc cagc                                    34

<210> SEQ ID NO 52
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 52
gctgggacag tctaaattcg ttgacttctg cggc                                    34

<210> SEQ ID NO 53
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 53
ggcttctgga gggtccagtg gagacaggat atcgttc                                 37

<210> SEQ ID NO 54
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 54
gaacgatatc ctgtctccac tggaccctcc agaagcc                                 37

<210> SEQ ID NO 55
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 55
cttcggcttc tggagggtcc ggtctagaca ggatatcg                                38

<210> SEQ ID NO 56
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 56
cgatatcctg tctagaccgg accctccaga agccgaag                                38

<210> SEQ ID NO 57
<211> LENGTH: 35
<212> TYPE: DNA
<213> ORGANISM: Artificial Sequence
<220> FEATURE:
<223> OTHER INFORMATION: Synthetic oligonucleotide

```
<400> SEQUENCE: 57
ggacttcggc ttctggaggg ggcagtctag acagg                                    35

<210> SEQ ID NO 58
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 58
cctgtctaga ctgcccccctc cagaagccga agtcc                                   35

<210> SEQ ID NO 59
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 59
ggtcttggtc atgctcacgc acaggatctc tgttgtg                                  37

<210> SEQ ID NO 60
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 60
cacaacagag atcctgtgcg tgagcatgac caagacc                                  37

<210> SEQ ID NO 61
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 61
gggcgttctg attcacgcag tcctgcagtt tgccc                                    35

<210> SEQ ID NO 62
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 62
gggcaaactg caggactgcg tgaatcagaa cgccc                                    35

<210> SEQ ID NO 63
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 63
cagttacgag tgcgacatcc ctatcggc                                            28

<210> SEQ ID NO 64
```

-continued

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 64
ccctgaacac cctggtgaag cagc                                          24

<210> SEQ ID NO 65
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 65
ccctgatcag ctgttgggtc acg                                           23

<210> SEQ ID NO 66
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 66
cagcacctcc agggatctgc cc                                            22

<210> SEQ ID NO 67
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 67
ctggttttca tacagcacgt tgcaggtcac gccgattccg ttgaatctat agcacatctg   60
catggcaaag gggatc                                                   76

<210> SEQ ID NO 68
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 68
gatccccttt gccatgcaga tgtgctatag attcaacgga atcggcgtga cctgcaacgt   60
gctgtatgaa aaccag                                                   76

<210> SEQ ID NO 69
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 69
gcaggagctc ggcaaatacg agcagggatc                                    30

<210> SEQ ID NO 70
<211> LENGTH: 25
<212> TYPE: DNA
<213> ORGANISM: Artificial Sequence
```

-continued

<220> FEATURE:
<223> OTHER INFORMATION: Synthetic oligonucleotide

<400> SEQUENCE: 70
gccagaagtc agatgctcaa ggggc                                            25

<210> SEQ ID NO 71
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 71
cttctcgaac tgggggtggg accaggcgct atgatggtgg tgatg                      45

<210> SEQ ID NO 72
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 72
tgataatgac tcgagcgata attcactcct caggtgcagg ctgcc                      45

<210> SEQ ID NO 73
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 73
atgatggtgg tgatggtggt gatggcctgg gc                                    32

<210> SEQ ID NO 74
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 74
cacaggaaac agctatgacc atgattacgc caagct                                36

<210> SEQ ID NO 75
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 75
gatccgcccc ctccactacc tcatcacttc tcgaactggg ggtggg                     46

<210> SEQ ID NO 76
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 76 cccacccccca gttcgagaag tgatgaggta gtggagggggg cggatc                   46

-continued

```
<210> SEQ ID NO 77
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 77
ctcgaactgg gggtgggacc atcatcaatg atggtggtga tggtggtg                    48

<210> SEQ ID NO 78
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 78
caccaccatc accaccatca ttgatgatgg tcccaccccc agttcgag                    48

<210> SEQ ID NO 79
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 79
cagggcgctg ggggtagagg agagggagtc ctggatcttg                            40

<210> SEQ ID NO 80
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 80
tcctctaccc ccagcgccct gggcaaac                                          28
```